US009175261B2

(12) United States Patent
Harmon et al.

(10) Patent No.: US 9,175,261 B2
(45) Date of Patent: Nov. 3, 2015

(54) HUMAN UMBILICAL CORD TISSUE CELLS FOR INHIBITING ADVERSE IMMUNE RESPONSE IN HISTOCOMPATIBILITY-MISMATCHED TRANSPLANTATION

(75) Inventors: Alexander M. Harmon, Clinton, NJ (US); Janet E. Davis, Branchburg, NJ (US)

(73) Assignee: DePuy Synthes Products, Inc., Raynham, MA (US)

( * ) Notice: Subject to any disclaimer, the term of this patent is extended or adjusted under 35 U.S.C. 154(b) by 640 days.

(21) Appl. No.: 11/611,602

(22) Filed: Dec. 15, 2006

(65) Prior Publication Data

US 2007/0264269 A1   Nov. 15, 2007

Related U.S. Application Data

(60) Provisional application No. 60/751,395, filed on Dec. 16, 2005.

(51) Int. Cl.
| | | |
|---|---|---|
| A61K 48/00 | (2006.01) | |
| C12N 5/073 | (2010.01) | |
| A61K 35/51 | (2015.01) | |
| A61K 35/12 | (2015.01) | |

(52) U.S. Cl.
CPC .............. *C12N 5/0605* (2013.01); *A61K 35/51* (2013.01); *A61K 2035/122* (2013.01)

(58) Field of Classification Search
CPC ...................... C07K 2317/55; C07K 2317/624; C07K 2317/77; C07K 2319/00; C07K 2319/70; A61K 35/51
See application file for complete search history.

(56) References Cited

U.S. PATENT DOCUMENTS

| 3,393,054 | A | 7/1968 | Irie |
| 3,665,061 | A | 5/1972 | Eberly, Jr. |
| 3,930,954 | A | 1/1976 | Irie |
| 4,216,144 | A | 8/1980 | Ashmead |
| 4,290,962 | A | 9/1981 | Tachi et al. |
| 4,352,883 | A | 10/1982 | Lim .............................. 435/178 |
| 4,487,865 | A | 12/1984 | Balazs et al. |
| 4,882,162 | A | 11/1989 | Ikada et al. .................... 424/444 |
| 4,925,677 | A | 5/1990 | Feijen |
| 4,963,489 | A | 10/1990 | Naughton et al. .......... 435/240.1 |
| 5,004,681 | A | 4/1991 | Boyse et al. ....................... 435/2 |
| 5,192,553 | A | 3/1993 | Boyse et al. .................... 424/529 |
| 5,248,608 | A | 9/1993 | Van Dooren et al. |
| 5,286,632 | A | 2/1994 | Jones .......................... 435/91.2 |
| 5,320,962 | A | 6/1994 | Stiles et al. .................. 435/91.2 |
| 5,342,761 | A | 8/1994 | MacLeod ...................... 435/69.1 |
| 5,437,994 | A | 8/1995 | Emerson et al. ............... 435/373 |
| 5,443,950 | A | 8/1995 | Naughton et al. |
| 5,466,233 | A | 11/1995 | Weiner et al. .............. 604/890.1 |
| 5,486,359 | A | 1/1996 | Caplan et al. ................. 424/93.7 |
| 5,580,777 | A | 12/1996 | Bernard et al. |
| 5,589,376 | A | 12/1996 | Anderson et al. ........... 435/240.2 |
| 5,670,483 | A | 9/1997 | Zhang et al. ..................... 514/14 |
| 5,677,181 | A | 10/1997 | Parish ........................... 435/332 |
| 5,693,332 | A | 12/1997 | Hansbrough |
| 5,698,518 | A | 12/1997 | Carson et al. .................... 514/12 |
| 5,707,643 | A | 1/1998 | Ogura et al. ................... 424/428 |
| 5,718,922 | A | 2/1998 | Herrero-Vanrell et al. |
| 5,736,516 | A | 4/1998 | Louis .............................. 514/12 |
| 5,811,094 | A | 9/1998 | Caplan et al. ................. 424/93.7 |
| 5,827,735 | A | 10/1998 | Young et al. .................. 435/325 |
| 5,834,308 | A | 11/1998 | Peck et al. ..................... 435/325 |
| 5,840,580 | A | 11/1998 | Terstappen et al. ........... 435/372 |
| 5,842,477 | A | 12/1998 | Naughton et al. |
| 5,843,780 | A | 12/1998 | Thomson ...................... 435/363 |
| 5,843,781 | A | 12/1998 | Ballermann et al. |
| 5,855,619 | A | 1/1999 | Caplan et al. |
| 5,869,079 | A | 2/1999 | Wong et al. ................... 424/426 |
| 5,902,598 | A | 5/1999 | Chen et al. .................... 424/423 |
| 5,902,741 | A | 5/1999 | Purchio et al. |
| 5,906,934 | A | 5/1999 | Grande et al. ................ 435/325 |
| 5,919,702 | A | 7/1999 | Purchio et al. ................ 435/378 |
| 5,942,225 | A | 8/1999 | Bruder et al. ................. 424/93.7 |
| 5,955,343 | A | 9/1999 | Holmes et al. ............. 435/240.1 |
| 5,962,325 | A | 10/1999 | Naughton et al. |
| 5,994,094 | A | 11/1999 | Hötten et al. ................. 435/69.1 |
| 6,001,647 | A | 12/1999 | Peck et al. .................... 435/325 |
| 6,022,743 | A | 2/2000 | Naughton et al. ............ 435/395 |
| 6,140,039 | A | 10/2000 | Naughton et al. ............. 435/1.1 |

(Continued)

FOREIGN PATENT DOCUMENTS

| EP | 1 216 718 | 6/2002 |
| EP | 1 316 322 | 6/2003 |

(Continued)

OTHER PUBLICATIONS

Hofmeister, et al (Bone Marrow, Transplantation, 39: 11-23, 2007.*
Nehlin et al (p. 1-42, 2011).*
Mattsson et al (Biol Blood Marrow Transplant. Jan. 2008 ; 14(Supplement 1): 165-170, 2008).*
Mineo et al (American Journal of Transplantation, 8: 1262-1274, 2008).*
U.S. Appl. No. 08/430,768, filed Apr. 27, 1995, Peterson.
U.S. Appl. No. 11/617,346, filed Dec. 28, 2006, Kihm.
Abbas, A.K., Lichtman, A.H., *Cellular and Molecular Immunology*, 5th Ed. (2003) Saunders, Philadelphia, p. 171.
Aboody, K.S., et al., "Neural stem cells display extensive tropism for pathology in adult brain: evidence from intracranial gliomase," *PNAS*, 2000, 97(23), 12846-12851.

(Continued)

*Primary Examiner* — Deborah Crouch
*Assistant Examiner* — Magdalene Sgagias
(74) *Attorney, Agent, or Firm* — Bernard F. Plantz; Johnson & Johnson

(57) ABSTRACT

Cell-based compositions and methods of their use to inhibit an adverse immune response such as graft versus host disease or rejection of transplanted tissue in a transplant recipient that is histocompatibility mismatched to the transplant donor are disclosed. The compositions and methods utilize postpartum-derived cells, such as cells derived from the placenta or umbilicus.

27 Claims, 4 Drawing Sheets

(56) References Cited

U.S. PATENT DOCUMENTS

| | | |
|---|---|---|
| 6,171,610 B1 | 1/2001 | Vacanti et al. |
| 6,200,606 B1 | 3/2001 | Peterson ............... 424/574 |
| 6,200,806 B1 | 3/2001 | Thomson ............... 435/366 |
| 6,214,369 B1 | 4/2001 | Grande et al. ........... 424/423 |
| 6,221,904 B1 | 4/2001 | Agus et al. |
| 6,251,090 B1 | 6/2001 | Avery et al. ............... 604/9 |
| 6,291,240 B1 | 9/2001 | Mansbridge et al. |
| 6,323,188 B1 | 11/2001 | Weissman ............... 514/52 |
| 6,326,201 B1 | 12/2001 | Fung et al. ............ 435/377 |
| 6,331,313 B1 | 12/2001 | Wong et al. ............ 424/427 |
| 6,333,029 B1 | 12/2001 | Vyakarnam et al. |
| 6,355,239 B1 | 3/2002 | Bruder et al. ........... 424/93.1 |
| 6,355,699 B1 | 3/2002 | Vyakarnam et al. ....... 521/61 |
| 6,358,737 B1 | 3/2002 | Bonewald et al. |
| 6,372,494 B1 | 4/2002 | Naughton et al. |
| 6,375,972 B1 | 4/2002 | Guo et al. ............... 424/423 |
| 6,387,367 B1 | 5/2002 | Davis-Sproul et al. ..... 424/93.1 |
| 6,391,297 B1 | 5/2002 | Halvorsen ............ 424/93.7 |
| 6,429,013 B1 | 8/2002 | Halvorsen et al. ........ 435/377 |
| 6,436,704 B1 | 8/2002 | Roberts et al. ........... 435/366 |
| 6,497,875 B1 | 12/2002 | Sorrell et al. ........... 424/93.7 |
| 6,528,245 B2 | 3/2003 | Sanchez-Ramos et al. ... 435/1.1 |
| 6,534,084 B1 | 3/2003 | Vyakarnam et al. |
| 6,541,028 B1 | 4/2003 | Kuri-Harcuch et al. |
| 6,555,374 B1 | 4/2003 | Gimble et al. ........... 435/371 |
| 6,599,323 B2 | 7/2003 | Melican et al. .......... 623/23.72 |
| 6,610,535 B1 | 8/2003 | Lu et al. ................ 435/325 |
| 6,638,765 B1 | 10/2003 | Rosenberg ............ 435/377 |
| 6,673,606 B1 | 1/2004 | Tennekoon et al. ....... 435/372 |
| 6,680,198 B1 | 1/2004 | Snyder et al. ........... 435/368 |
| 6,686,198 B1 | 2/2004 | Melton et al. ........... 435/377 |
| 6,703,017 B1 | 3/2004 | Peck et al. ............. 424/93.7 |
| 6,916,655 B2 | 7/2005 | Yasumoto et al. ......... 435/371 |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,318,483 B2 | 11/2012 | Mistry et al. |
| 8,658,152 B2 | 2/2014 | Messina et al. |
| 8,703,121 B2 | 4/2014 | Harris et al. |
| 2001/0024824 A1 | 9/2001 | Moss et al. ............ 435/366 |
| 2001/0031256 A1 | 10/2001 | Edge ................. 424/93.7 |
| 2001/0046489 A1 | 11/2001 | Habener et al. ......... 424/93.21 |
| 2001/0053362 A1 | 12/2001 | Walters |
| 2002/0022676 A1 | 2/2002 | He et al. ............... 523/113 |
| 2002/0028510 A1 | 3/2002 | Sanberg et al. ......... 435/368 |
| 2002/0062151 A1 | 5/2002 | Altman et al. ........... 623/13.7 |
| 2002/0081725 A1 | 6/2002 | Tsang et al. ........... 435/366 |
| 2002/0098584 A1 | 7/2002 | Palmer et al. ........... 435/366 |
| 2002/0119565 A1 | 8/2002 | Clarke et al. ........... 435/366 |
| 2002/0123141 A1 | 9/2002 | Hariri .................. 435/366 |
| 2002/0150986 A1 | 10/2002 | Lau |
| 2002/0151056 A1 | 10/2002 | Sasai et al. ............ 435/368 |
| 2002/0160471 A1 | 10/2002 | Kisiday et al. .......... 435/177 |
| 2002/0160510 A1 | 10/2002 | Hariri .................. 435/368 |
| 2002/0164307 A1 | 11/2002 | Habener et al. ........ 424/93.7 |
| 2002/0164791 A1 | 11/2002 | Van Der Kooy et al. .... 435/366 |
| 2002/0168763 A1 | 11/2002 | Yan et al. ............. 435/325 |
| 2002/0182728 A1 | 12/2002 | Ramiya et al. ......... 435/366 |
| 2002/0187550 A1 | 12/2002 | Dinsmore et al. ....... 435/377 |
| 2002/0192816 A1 | 12/2002 | Roberts et al. ......... 435/366 |
| 2003/0003574 A1 | 1/2003 | Toma et al. ........... 435/368 |
| 2003/0007954 A1 | 1/2003 | Naughton et al. |
| 2003/0022369 A1 | 1/2003 | Fillmore et al. ......... 435/371 |
| 2003/0031657 A1 | 2/2003 | Habener et al. ........ 424/93.21 |
| 2003/0032178 A1 | 2/2003 | Williams et al. ........ 435/366 |
| 2003/0032179 A1 | 2/2003 | Hariri |
| 2003/0032183 A1 | 2/2003 | Sheridan ............. 435/370 |
| 2003/0049837 A1 | 3/2003 | Weiss et al. .......... 435/368 |
| 2003/0059939 A1 | 3/2003 | Page et al. .......... 435/366 |
| 2003/0082155 A1 | 5/2003 | Habener et al. ...... 424/93.21 |
| 2003/0082160 A1 | 5/2003 | Yu et al. ........... 424/93.21 |
| 2003/0096409 A1 | 5/2003 | Yasumoto et al. ........... 435/371 |
| 2003/0104997 A1 | 6/2003 | Black et al. ............... 514/12 |
| 2003/0109036 A1 | 6/2003 | Wu ...................... 435/366 |
| 2003/0113910 A1 | 6/2003 | Levanduski ............. 435/325 |
| 2003/0118566 A1 | 6/2003 | Neuman et al. .......... 424/93.21 |
| 2003/0124721 A1 | 7/2003 | Cheatham et al. ......... 435/366 |
| 2003/0138948 A1 | 7/2003 | Fisk et al. ............. 435/366 |
| 2003/0138951 A1 | 7/2003 | Yin ..................... 435/370 |
| 2003/0148513 A1 | 8/2003 | Sugaya et al. ........... 435/368 |
| 2003/0161818 A1 | 8/2003 | Weiss et al. ........... 424/93.21 |
| 2003/0162290 A1 | 8/2003 | Inoue et al. ............ 435/366 |
| 2003/0170215 A1 | 9/2003 | Tsang et al. ........... 424/93.21 |
| 2003/0175963 A1 | 9/2003 | Rosenberg ............. 435/375 |
| 2003/0180269 A1 | 9/2003 | Hariri ................. 424/93.21 |
| 2003/0186439 A1 | 10/2003 | Nakauchi et al. ........ 435/370 |
| 2003/0199447 A1 | 10/2003 | Goldman et al. ......... 514/12 |
| 2003/0203483 A1 | 10/2003 | Seshi .................. 435/366 |
| 2003/0203484 A1 | 10/2003 | Black et al. ........... 435/368 |
| 2003/0207450 A1 | 11/2003 | Young et al. ........... 435/368 |
| 2003/0211087 A1 | 11/2003 | Goldman ............. 424/93.21 |
| 2003/0211603 A1 | 11/2003 | Earp et al. ........... 435/366 |
| 2003/0211605 A1 | 11/2003 | Lee et al. ............ 435/368 |
| 2003/0212024 A1 | 11/2003 | Keating et al. ......... 514/44 |
| 2003/0219894 A1 | 11/2003 | Seino et al. ........... 435/370 |
| 2003/0228295 A1 | 12/2003 | Svendsen ............. 424/93.21 |
| 2003/0235563 A1 | 12/2003 | Strom et al. .......... 424/93.21 |
| 2003/0235909 A1 | 12/2003 | Hariri et al. .......... 435/372 |
| 2004/0005704 A1 | 1/2004 | Csete et al. .......... 435/368 |
| 2004/0009593 A1 | 1/2004 | Keirstead et al. ....... 435/368 |
| 2004/0014206 A1 | 1/2004 | Robl et al. ........... 435/325 |
| 2004/0014210 A1 | 1/2004 | Jessell et al. ......... 435/368 |
| 2004/0014211 A1 | 1/2004 | Ogle et al. .......... 435/368 |
| 2004/0014662 A1 | 1/2004 | Lindquist et al. ....... 514/12 |
| 2004/0028660 A1 | 2/2004 | Hariri et al. |
| 2004/0029269 A1 | 2/2004 | Goldman et al. ....... 435/368 |
| 2004/0033597 A1 | 2/2004 | Toma et al. .......... 435/368 |
| 2004/0037818 A1 | 2/2004 | Brand et al. ......... 424/93.21 |
| 2004/0048372 A1 | 3/2004 | Hariri ............... 435/366 |
| 2004/0058412 A1 | 3/2004 | Ho et al. ............ 435/69.1 |
| 2004/0063202 A1 | 4/2004 | Petersen et al. ....... 435/368 |
| 2004/0072344 A1 | 4/2004 | Inoue et al. ......... 435/366 |
| 2004/0136967 A1 | 7/2004 | Weiss et al. ......... 424/93.7 |
| 2005/0019865 A1 | 1/2005 | Kihm et al. .......... 435/69.1 |
| 2005/0032209 A1 | 2/2005 | Messina et al. ....... 435/366 |
| 2005/0037491 A1 | 2/2005 | Mistry et al. ........ 435/366 |
| 2005/0054098 A1 | 3/2005 | Mistry et al. ........ 435/372 |
| 2005/0058629 A1 | 3/2005 | Harmon et al. ....... 424/93.7 |
| 2005/0058630 A1 | 3/2005 | Harris et al. ........ 424/93.7 |
| 2005/0058631 A1 | 3/2005 | Kihm et al. ......... 424/93.7 |
| 2005/0074435 A1 | 4/2005 | Casper et al. ........ 424/93.7 |
| 2005/0148074 A1 | 7/2005 | Davies et al. ........ 435/372 |
| 2005/0249731 A1 | 11/2005 | Aslan et al. |
| 2006/0128014 A1 | 6/2006 | Haggblad et al. |
| 2006/0153815 A1 | 7/2006 | Seyda et al. |
| 2006/0153816 A1 | 7/2006 | Brown et al. ........ 424/93.7 |
| 2006/0153817 A1 | 7/2006 | Kihm et al. ......... 424/93.7 |
| 2006/0153818 A1 | 7/2006 | Dhanaraj et al. ..... 424/93.7 |
| 2006/0154366 A1 | 7/2006 | Brown et al. ........ 435/366 |
| 2006/0154367 A1 | 7/2006 | Kihm et al. ......... 435/366 |
| 2006/0166361 A1 | 7/2006 | Seyda et al. |
| 2006/0171930 A1 | 8/2006 | Seyda et al. |
| 2006/0188983 A1 | 8/2006 | Harris et al. ........ 435/366 |
| 2006/0223177 A1 | 10/2006 | Harris et al. ........ 435/325 |
| 2006/0233765 A1* | 10/2006 | Messina et al. ....... 424/93.7 |
| 2006/0233766 A1 | 10/2006 | Messina et al. ....... 424/93.7 |
| 2006/0234376 A1 | 10/2006 | Mistry et al. ........ 435/366 |
| 2006/0281793 A1 | 12/2006 | Gupta et al. |
| 2007/0009494 A1 | 1/2007 | Mistry et al. ........ 424/93.7 |
| 2007/0014771 A1 | 1/2007 | Mistry et al. ........ 424/93.7 |
| 2007/0036767 A1 | 2/2007 | Mistry et al. ........ 424/93.7 |
| 2007/0141700 A1 | 6/2007 | Harmon |
| 2007/0264713 A1 | 11/2007 | Terstegge et al. |
| 2007/0275362 A1 | 11/2007 | Edinger et al. |
| 2008/0112939 A1 | 5/2008 | Colter et al. |
| 2008/0145934 A1 | 6/2008 | Harris et al. |
| 2008/0159994 A1 | 7/2008 | Mantalaris et al. |
| 2008/0166328 A1 | 7/2008 | Harmon et al. |
| 2008/0226595 A1 | 9/2008 | Edinger et al. |
| 2010/0210013 A1 | 8/2010 | Mistry et al. |

(56) References Cited

U.S. PATENT DOCUMENTS

| | | |
|---|---|---|
| 2010/0215714 A1 | 8/2010 | Messina et al. |
| 2010/0260843 A1 | 10/2010 | Messina et al. |
| 2010/0272803 A1 | 10/2010 | Mistry et al. |
| 2012/0315251 A1 | 12/2012 | Harris et al. |
| 2013/0022585 A1 | 1/2013 | Messina et al. |
| 2014/0045263 A1 | 2/2014 | Mistry et al. |
| 2014/0154226 A1 | 6/2014 | Messina et al. |

FOREIGN PATENT DOCUMENTS

| | | |
|---|---|---|
| EP | 0 333 328 B1 | 12/2003 |
| EP | 1 405 649 | 4/2004 |
| JP | 2002-506831 | 9/1999 |
| JP | 2003-235549 | 8/2003 |
| JP | 2004-210713 | 7/2004 |
| WO | 90/11354 A1 | 10/1990 |
| WO | 92/03917 A1 | 3/1992 |
| WO | 93/04169 A1 | 3/1993 |
| WO | 94/25584 A1 | 11/1994 |
| WO | 95/17911 A1 | 7/1995 |
| WO | WO 95/23216 | 8/1995 |
| WO | 96/01316 A1 | 1/1996 |
| WO | 96/05309 A2 | 2/1996 |
| WO | 98/17791 A1 | 4/1998 |
| WO | 98/51317 A1 | 11/1998 |
| WO | WO 99/03973 | 1/1999 |
| WO | WO 99/28444 | 6/1999 |
| WO | WO 99/47163 | 9/1999 |
| WO | 00/09666 A2 | 2/2000 |
| WO | WO 00/38762 | 7/2000 |
| WO | WO 00/46351 | 8/2000 |
| WO | WO-00/53795 A1 | 9/2000 |
| WO | 00/73421 A3 | 12/2000 |
| WO | 01/11011 A2 | 2/2001 |
| WO | 01/19379 A3 | 3/2001 |
| WO | 01/34775 A1 | 5/2001 |
| WO | 02/29971 A1 | 4/2002 |
| WO | WO 02/36751 | 5/2002 |
| WO | 02/46373 A1 | 6/2002 |
| WO | 02/059278 A2 | 8/2002 |
| WO | 02/062969 A2 | 8/2002 |
| WO | 02/063962 A1 | 8/2002 |
| WO | 02/064748 A2 | 8/2002 |
| WO | 02/064755 A2 | 8/2002 |
| WO | WO 02/061053 | 8/2002 |
| WO | 02/086107 A2 | 10/2002 |
| WO | 03/023020 A1 | 3/2003 |
| WO | 03/025149 A2 | 3/2003 |
| WO | 03/029443 A1 | 4/2003 |
| WO | 03/029445 A1 | 4/2003 |
| WO | 03/039489 A3 | 5/2003 |
| WO | 03/042405 A2 | 5/2003 |
| WO | 03/048336 A2 | 6/2003 |
| WO | 03/055992 A2 | 7/2003 |
| WO | 03/064601 A2 | 8/2003 |
| WO | 03/066832 A2 | 8/2003 |
| WO | 03/068937 A2 | 8/2003 |
| WO | 03/070922 A1 | 8/2003 |
| WO | 03/072728 A2 | 9/2003 |
| WO | 03/080822 A1 | 10/2003 |
| WO | 03/087333 A2 | 10/2003 |
| WO | 03/087392 A2 | 10/2003 |
| WO | 03/089619 A2 | 10/2003 |
| WO | 03/010038 A1 | 12/2003 |
| WO | 03/102134 A2 | 12/2003 |
| WO | 03/102151 A2 | 12/2003 |
| WO | 03/104442 A1 | 12/2003 |
| WO | 2004/011012 A2 | 2/2004 |
| WO | 2004/011621 A2 | 2/2004 |
| WO | 2004/016747 A2 | 2/2004 |
| WO | 2004/023100 A2 | 3/2004 |
| WO | 2004/072273 A1 | 8/2004 |
| WO | 2005/001076 A2 | 1/2005 |
| WO | 2005/001077 A2 | 1/2005 |
| WO | 2005/001078 A2 | 1/2005 |
| WO | 2005/001079 A2 | 1/2005 |
| WO | 2005/001080 A2 | 1/2005 |
| WO | 2005/003334 A2 | 1/2005 |
| WO | WO 2005/007176 | 1/2005 |
| WO | WO 2005/021738 | 3/2005 |
| WO | 2005/038012 A2 | 4/2005 |
| WO | WO 2005/042703 | 5/2005 |
| WO | WO 2006/027229 | 3/2006 |
| WO | WO 2006/036826 | 4/2006 |
| WO | 2006/071773 A2 | 7/2006 |
| WO | 2006/071777 A2 | 7/2006 |
| WO | 2006/071778 A2 | 7/2006 |
| WO | 2006/071794 A2 | 7/2006 |
| WO | 2006/071802 A2 | 7/2006 |
| WO | WO 2006/083394 | 8/2006 |
| WO | WO 2006/105152 | 10/2006 |
| WO | WO 2007/047468 | 4/2007 |
| WO | WO 2007/070870 A1 | 6/2007 |
| WO | WO 2007/073552 | 6/2007 |
| WO | WO 2007/108003 | 9/2007 |
| WO | WO 2008/045498 | 4/2008 |
| WO | WO 2008/060541 | 5/2008 |
| WO | WO 2007/070870 R | 6/2008 |

OTHER PUBLICATIONS

Age-Related Eye Disease Study Research Group, "A randomized, placebo-controlled, clinical trial of high-dose supplementation with vitamins C and E, beta carotene, and zinc for age-related macular degeneration and vision loss," AREDS Report No. 8, *Arch. Ophthalmal*, 2001, 119, 1417-1436.

Aggarwal, S. et al., "Human mesenchymal stem cells modulate allogeneic immune cell responses," *Blood*, Feb. 15, 2005, 105(4), 1815-1822 (Prepublished online as a Blood First Edition Paper on Oct. 19, 2004).

Allcock, H.R., et al., "Synthesis of poly[amino acid alkyl ester)phosphazenes]$^{1-3}$," *Macromolecule*, 1977, 10(4), 824-830.

Altman, G.H., et al., "Advanced bioreactor with controlled application of multi-dimensional strain for tissue engineering," *J. Biomech. Eng.*, 2002, 124, 742-749.

Altman, R.D., et al., "Radiographic assessment of progression in osteoarthritis," *Arthritis & Rheum.*, 1987, 30(11), 1214-1225.

Anseth, K.S., et al., "In situ forming degradable networks and their application in tissue engineering and drug delivery," *J. of Control Release*, 2002, 78, 199-209.

Auda-Boucher, G., et al., "Staging of the commitment of murine cardiac cell progenitors," *Dev. Bio.*, 2000, 225(1), 214-225 (Abstract 2 pages).

Avital, I., et al., "Isolation, characterization, and transplantation of bone marrow-derived hepatocyte stem cells," *Biochem. & Biophys. Res. Comm.*, 2001, 288, 156-164.

Azizi, S.A., et al., "Engraftment and migration of human bone marrow stromal cells implanted in the brains of albino rats—similarities to astrocyte grafts," *Proc. Natl. Acad. Sci. USA*, 1998, 95, 3908-3913.

Baker, K.A., et al., "Intrastriatal and intranigral grafting of hNT neurons in the 6-OHDA rat model of Parkinson's Disease," *Exper. Neurol.*, 2000, 162, 350-360.

Balis, F., et al., "Central nervous system pharmacology of antileukemic drugs," *Am. J. of Pediatric. Hematol. Oncol.*, 1989, 11(1), 74-86.

Balkema, G.W., et al., "Impaired visual thresholds in hypopigmented animals," *Visual Neuroscience*, 1991, 6, 577-585.

Bao, Z.Z.., et al., "Regulation of chamber-specific gene expression in the developing heart by Irx4," *Science*, 1999, 283(5405), 1161-1164 (Abstract 1 page).

Barberi, T., et al., "Neural subtype specification of fertilization and nuclear transfer embryonic stem cells and application in parkinsonian mice," *Nature Biotechnology*, 2003, 21(10), 1200-1207.

Beck, R.W., et al., "A clinical comparison of visual field testing with a new automated perimeter, the Humphrey field analyzer, and the Goldmann perimeter," *Ophthalmology*, 1985, 92(1), 77-82.

(56) References Cited

OTHER PUBLICATIONS

Björklund, L.M., et al., "Embryonic stem cells develop into functional dopaminergic neurons after transplantation in a Parkinson rat model," *PNAS*, 2002, 99(4), 2344-2349.
Bradley, B. A., "The role of HLA matching in transplantation," *Immunol Lett*, 1991, 29(1-2), 55-59.
Brodsky, S.V., et al., "Coagulation, fibrinolysis and angiogenesis: new insights from knockout mice," *Exp. Nephrol.*, 2002, 10, 299-306.
Brooks, P., "Inflammation as an important feature of osteoarthritis," *Bull. rld Health Org.*, 2003, 81(9), 689-690.
Brown, J. A., et al., "Blockade of programmed death-1 ligands on dendritic cells enhances T cell activation and cytokine production," *The J. of Immunology*, 2003, 170, 1257-1266.
Burnstein, R.M., et al., "Differentiation and migration of long term expanded human neural progenitors in a partial lesion model of Parkinson's disease," *Intern. J. of Biochem. & Cell Biology*, 2004, 36, 702-713.
Caballero, S., et al., "The many possible roles of stem cells in age-related macular degeneration," *Graefe's Arch Clin. Exp. Ophthalmol*, 2004, 242, 85-90.
Campbell, I.K., et al., "Human articular cartilage and chondrocytes produce hemopoietic colony-stimulating factors in culture in response to IL-$1^1$," *J. of Immun.*, 1991, 147, 1238-1246.
Cao, Q., et al., "Stem cell repair of central nervous system injury," *J. of Neuroscience Res.*, 2002, 68, 501-510.
Caplan, A.I., et al., "Mesenchymal stem cells: building blocks for molecular medicine in the $21^{st}$ century," *Trends in Molecular Med.*, 2001, 7(6), 259-264.
Chagraoui, J., et al., "Fetal liver stroma consists of cells in epithelial-to-mesenchymal transition," *Blood*, 2003, 101, 2973-2982.
Chen, D., et al., "Differential roles for bone morphogenic protein (BMP) receptor type IB and IA in differentiation and specification of mesenchymal precursor cells to osteoblast and adipocyte lineages," *J. Cell Biol.*, 1998, 142(1), 295-305.
Cheng, A., et al., "Nitric oxide acts in a positive feedback loop with BDNF to regulate neural progenitor cell proliferation and differentiation in the mammalian brain," *Dev. Biol.*, 2003, 258, 319-333.
Constantini, S., et al., "The effects of methylprednisolone and the ganglioside GM1 on acute spinal cord injury in rats," *J. Neurosurg.*, 1994, 80(1), 97-111 (Abstract 2 pages.
Coumans, B., et al., "Lymphoid cell apoptosis induced by trophoblastic cells: a model of active foeto-placental tolerance," *J. of Immunological Methods*, 1999, 224, 185-196.
D'Cruz, P.M., et al., "Mutation of the receptor tyrosine kinase gene Mertk in the retinal dystrophic RCS rat," *Hum. Mol. Genet.*, 2000, 9(4), 645-651.
Danon, D., et al., "Macrophage treatment of pressure sores in paraplegia," *J. of und Care*, 1998, 7(6), 281-283.
Danon, D., et al., "Treatment of human ulcers by application of macrophages prepared from a blood unit," *Exp. Gerontol.*, 1997, 32(6), 633-641.
Davies, S. M. et al., "Engraftment and survival after unrelated-donor bone marrow transplantation: a report from the national marrow donor program," *Blood*, 2000, 96(13), 4096-41002.
Dawson, T.M., et al., "Neuroprotective and neurorestorative strategies for Parkinson's disease," *Nat. Neurosci.*, 2002, 5 Suppl., 1058-1061 (Abstract 1 page).
Dickinson, A. M et al., "Non-HLA immunogenetics in hematopoietic stem cell transplantation," *Curr. Opin. Immunol.*, 2005, 17(5), 517-525.
Dimri, G.P., et al., "A biomarker that identifies senescent human cells in culture and in aging skin in vivo," *Proc. Natl. Acad. Sci. USA*, 1995, 92, 9363-9367.
Domb, A., et al., "Degradable polymers for site-specific drug delivery," *Polymers for Advanced Technologies*, 1992, 3, 279-292.
Doshi, S.N., et al., "Evolving role of tissue factor and its pathway inhibitor," *Critical Care Med.*, 2002, 30(5), S241-S250.
Doyle, J., "Spiraling complexity, robustness, and fragility in biology," http://www.cds.caltech.edu/~doyle/CmplxNets/Bio1.pdf, available online Feb. 28, 2004.

Du, Y., et al., "Functional reconstruction of rabbit corneal epithelium by human limbal cells cultured on amniotic membrane," *Molecular Vision*, 2003, 9, 635-643.
Eagle, H., "The specific amino acid requirements of a mammalian cell (strain L) in tissue culture," *J. Biol. Chem.*, Jun. 1955, 214(2), 839-852.
Eblenkamp, M. et al., "Umbilical cord stromal cells (UCSC). Cells featuring osteogenic differentiation potential," *Der Orthopade*, Dec. 2004, 33(12), 1338-1345 (English abstract on p. 1339).
Edelstein, M. L. et al., "Gene therapy clinical trials worldwide 1989-2004—an overview," *J. Gene Med.*, Jun. 2004, 6(6), 597-602.
Edlund, H., "Pancreatic organogenesis—developmental mechanisms and implications for therapy," *Nat. Rev. Genet.*, 2002, 3, 524-532.
Efrat, S., et al., "Cell replacement therapy for type 1 diabetes," *TRENDS in Molecular Medicine*, 2002, 8(7), 334-339.
Ehtesham, M., et al., "Induction of glioblastoma apoptosis using neural stem cell-mediated delivery of tumor necrosis factor-related apoptosis-inducing ligand," *Cancer Res.*, 2002, 62, 7170-7174.
Ehtesham, M., et al., "The use of interleukin 12-secreting neural stem cells for the treatment of intracranial glioma," *Cancer Res.*, 2002, 5657-5663.
Eisenhofer, G., E., et al., "Tyrosinase: a developmentally specific major determinant of peripheral dopamine," *FASEB J.*, 2003, 1248-1255.
Ende, N., et al., "Parkinson's disease mice and human umbilical cord blood," *J. Med.*, 2002, 33(1-4), 173-180, 1 page (Abstract).
Engstad, C.S., et al., "The effect of soluble β-1,3-glucan and lipopolysaccharide on cytokine production and coagulation activation in whole blood," *Int. Immunopharmacol.*, 2002, 2, 1585-1597.
Enzmann, V., et al., "Enhanced induction of RPE lineage markers in pluripotent neural stem cells engrafted into the adult rat subretinal space," *Investig. Ophthalmol. Visual Sci.*, 2003, 44, 5417-5422.
Fazleabas, A.T., et al., "Endometrial function: cell specific changes in the uterine environment," *Mol. & Cellular. Endo.*, 2002, 186, 143-147.
Fiegel, H.C., et al., "Liver-specific gene expression in cultured human hematopoietic stem cells," *Stem Cells*, 2003, 21, 98-104.
Fischer, D., et al., "Lens-injury-stimulated axonal regeneration throughout the optic pathway of adult rats," *Exp. Neurol.*, 2001, 172, 257-272.
Foley, A. et al., "Heart induction: embryology to cardiomyocyte regeneration," *Trends Cardiovasc Med.*, Apr. 2004, 14(3), 121-125.
Freed, C.R., et al., "Transplantation of embryonic dopamine neurons for severe Parkinson's disease," *N. Engl. J. Med.*, 2001, 344(10), 710-719.
Frenkel, O., et al., "Activated macrophages for treating skin ulceration: gene expression in human monocytes after hypo-osmotic shock," *Clin. Exp. Immunol.*, 2002, 128, 59-66.
Friedman, J.A., et al., "Biodegradable polymer grafts for surgical repair of the injured spinal cord," *Neurosurgery*, 2002, 51(3), 742-751.
Fukuchi, Y. et al., "Human Placenta-Derived Cells Have Mesenchymal Stem/Progenitor Cell Potential," *Stem Cells*, Alphamed Press, Dayton Ohio, 2004, 22(5), 649-658.
Fukuda, K., et al., "Reprogramming of bone marrow mesenchymal stem cells into cardiomyocytes," *C.R. Biol.*, 2002, 325, 1027-1038.
Gellersen, B., et al., "Cyclic AMP and progesterone receptor cross-talk in human endometrium: a decidualizing affair," *J. of Endocrinol.*, 2003, 178, 357-372.
Gerdes, D., et al., "Cloning and tissue expression of t putative steroid membrane receptors," *Biol. Chem.*, 1998, 379, 907-911.
Gökhan, S., et al., "Basic and clinical neuroscience applications of embryonic stem cells," *Anat. Rec. (New Anat)*, 2001, 265, 142-156.
Goodwin, H. S. et al., "Multilineage differentiation activity by cells isolated from umbilical cord blood: Expression of bone, fat and neural markers," *Biology of Blood and Marrow Transplantation*, 2001, 7, 581-588.
Gosiewska, A., et al., "Development of a three-dimensional transmigration assay for testing cell-polymer interactions for tissue engineering applications," *Tissue Eng.*, 2001, 7(3), 267-277.
Gottleib, D.I., "Large-scale sources of neural stem cells," *Ann. Rev. Neurosci.*, 2002, 25, 381-407.

(56) References Cited

OTHER PUBLICATIONS

Halvorsen, Y.D., et al., "Extracellular matrix mineralization and osteoblast gene expression by human adipose tissue-derived stromal cells," *Tissue Eng.*, 2001, 7, 729-741.
Hanahan, D., "Heritable formation of pancreatic β-cell tumours in transgenic mice expressing recombinant insulin/simian virus 40 oncogenes," *Nature*, 1985, 315, 115-122.
Haruta, M., et al., "In vitro and in vivo characterization of pigment epithelial cells differentiated from primate embryonic stem cells," *Investig. Ophthalmol. & Visual Sci.*, 2004, 45(3), 1020-1025.
Hayflick, L., "The longevity of cultured human cells," *J. Am. Geriatr. Soc.*, 1974, 22(1), 1-12.
Hayflick, L., "The strategy of senescence," *Gerontologist*, 1974, 14(1), 37-45.
Hill, M. et al., "Treatment for swallowing difficulties (dysphagia) in chronic muscle disease," *Cochrane Database Syst Rev.*, 2004, (2):CD004303.
Holz, F. G. et al., "Intraocular microablation of choroidal tissue by a 308 nm AIDA excimer laser for RPE-transplantation in patients with age-related macular degeneration," *Biomed Tech (Berlin)*, Apr. 2003, 48(4), 82-85.
Hongpaisan, J., "Inhibition of proliferation of contaminating fibroblasts by D-valine in cultures of smooth muscle cells from human myometrium," *Cell Biol. Int.*, 2000, 24, 1-7.
Hu, A., et al., "Hepatic differentiation from embryonic stem cells in vitro," *Chin. Med. J.*, 2003, 116(12), 1893-1897.
Hughes, G.C., et al., "Therapeutic angiogenesis in chronically ischemic porcine myocardium: comparative effects of bFGF and VEGF," *Ann. Thorac. Surg.*, 2004, 77, 812-818.
Hutmacher, D.W., "Scaffold design and fabrication technologies for engineering tissues—state of the art and future perspectives," *J. Biomater. Sci. Polymer Edn.*, 2001, 12(1), 107-124.
Isacson, O., "The production and use of cells as therapeutic agents in neurodegenerative diseases," *The Lancet (Neurology)*, 2003, 2, 417-424.
Isacson, O., et al., "Specific axon guidance factors persist in the adult brain as demonstrated by pig neuroblasts transplanted to the rat," *Neurosci.*, 1996, 75(3), 827-837.
Ishii, M. et al., "Molecular markers distinguish bone marrow mesenchymal stem cells from fibroblasts," *Biochemical and Biophysical Research Communications*, Jun. 24, 2005, 332(1), 297-303.
Ito, Y., et al., "A quantitative assay using basement membrane extracts to study tumor angiogenesis in vivo," *Int. J. Cancer*, 1996, 67, 148-152.
Iwasaki, T., "Recent advances in the treatment of graft-versus-host disease," *Clin. Med. Res.*, 2004, 2(4), 243-252.
Jackson, K.A., et al., "Regeneration of ischemic cardiac muscle and vascular endothelium by adult stem cells," *J. Clin. Invest.*, 2001, 107, 1395-1402.
Jaffe, E. A. et al., "Culture of human endothelial cells derived from umbilical veins," *J Clin Invest*, 1973, 52, 2745-2756.
Janderova, L., et al., "Human mesenchymal stem cells as an in vitro model for human adipogenesis," *Obes. Res.*, 2003, 11(1), 65-74.
Jang, Y.K., et al., "Retinoic acid-mediated induction of neurons and glial cells from human umbilical cord-derived hematopoietic stem cells," *J. of Neurosci. Res.*, 2004, 75, 573-584.
Jeras, M., "The role of in vitro alloreactive T-cell functional tests in the selection of HLA matched and mismatched haematopoietic stem cell donors," *Transpl. Immunol.*, 2002, 10(2-3), 205-14.
Jikuhara, T. et al., "Left atrial function as a reliable predictor of exercise capacity in patients with recent myocardial infarction," *Chest*, Apr. 1997, 111(4), 922-928.
Johe, K.K., et al., "Single factors direct the differentiation of stem cells from the fetal and adult central nervous system," *Genes & Devel.*, 1996, 10, 3129-3140.
Johnstone, B., et al., "In vitro chondrogenesis of bone-marrow-derived mesenchymal stem cells," *Exp. Cell Res.*, 1998, 238, 265-272.
Jomura, S., et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.
Jones-Villeneuve, E.M., et al., "Retinoic acid-induced neural differentiation of embryonal carcinoma cells," *Mol. & Cellu. Biol.*, 1983, 3(12), 2271-2279.
Joussen, A. M., "Cell transplantation in age related macular degeneration: current concepts and future hopes," *Graefe's Arch. Clin. Exp. Ophthalmol.*, 2004, 242, 1-2.
Kadiyala, S., et al., "Culture expanded canine mesenchymal stem cells possess osteochondrogenic potential in vivo and in vitro," *Cell Transplant*, 1997, 6(2), 125-134.
Kicic, A., et al., "Differentiation of marrow stromal cells into photoreceptors in the rat eye," *J. of Neurosci.*, 2003, 23(21), 7742-7749.
Kim, J.-H., et al., "Dopamine neurons derived from embryonic stem cells function in an animal model of Parkinson's disease," *Nature*, 2002, 418, 50-56.
Kim, J.Y., et al., "Ocular surface reconstruction: limbal stem cell transplantation," *Ophthal. Clin. N Am.*, 2003, 16, 67-77.
Kim, S.K., et al., "Intercellular signals regulating pancreas development and function," *Genes Dev.*, 2001, 15, 111-127.
Klassen, H. et al., "Stem cells and retinal repair," *Prog. Retin. Eye Res.*, 2004, 23(2), 149-181 (Abstract 1 page).
Klein, Jan Immunology: The Science of Self-Nonself Discrimination John Wiley & Sons, New York p. 453-8.
Laface, D., et al., "Genetransfer into hematopoietic progenitor cells mediated by an adeno-associated virus vector," *Virology*, 1998, 162, 483-486.
Lang, K.J.D., et al., "Differentiation of embryonic stem cells to a neural fate: a route to re-building the nervous system," *J. of Neurosci. Res.*, 2004, 76, 184-192.
Langeggen, H. et al., "HUVEC take up opsonized zymosan particles and secrete cytokines IL-6 and IL-8 in vitro," *FEMS Immunol. Med. Microbiol.*, 2003, 36, 55-61.
Le Belle, J.E., et al., "Stem cells for neurodegenerative disorders: where can we go from here?," *BioDrugs*, 2002, 16, 389-401.
Le Bouteiller, P., et al., "Soluble HLA-G1 at the materno-foetal interface-a review," *Placenta*, 2003, 24 (Suppl. A), S10-S15.
Li, A., et al., "IL-8 directly enhanced endothelial cell survival, proliferation, and matrix metalloproteinases production and regulated angiogenesis," *J. Immunol.*, 2003, 170(6), 3369-3376.
Li, L.X., et al., "Inherited retinal dystrophy in the RCS rat: prevention of photoreceptor degeneration by pigment epithelial cell transplantation," *Exp. Eye Res.*, 1988, 47, 911-917.
Li, Y., et al., "Intracerebral transplantation of bone marrow stromal cells in a 1-methyl-4-phenyl-1,2,3,6-tetrahydropyridine mouse model of Parkinson's disease," *Neuroscience Letts.*, 2001, 315, 67-70.
Li, Y., et al., "Transplanted olfactory ensheathing cells promote regeneration of cut adult rat optic nerve axons," *J. of Neuro.*, 2003, 23(21), 7783-7788.
Liu, Y.-J., et al., "Molecular and genetic mechanisms of obesity: implications for future management," *Curr. Mol. Med.*, 2003, 3, 325-340.
Lockhart, D. J. et al., "Expression monitoring by hybridization to high-density oligonucleotide arrays," *Nat. Biotechnol.*, 1996, 14(13), 1675-1680.
Lodie, T. A. et al., "Systematic Analysis of Reportedly Distinct Populations of Mulitpotent Bone Marrow-Derived Stem Cells Reveals a Lack of Distinction," *Tissue Engineering*, Oct. 2002, 8(5), 739-751.
Lund, R.D., et al., "Cell transplantation as a treatment for retinal disease," *Progress in Retinal and Eye Research*, 2001, 20(4), 415-449.
Lund, R.D., et al., "Subretinal transplantation of genetically modified human cell lines attenuates loss of visual function in dystrophic rats," *Proc. Natl. Acad. Sci. USA*, 2001, 98(17), 9942-9947.
Lund, R.L., et al., "Retinal transplantation: progress and problems in clinical application," *J. Leukocyte Biol.*, 2003, 74, 151-160.
Luo, D. et al., "Synthetic DNA delivery systems," *Nat. Biotechnol.*, Jan. 2000, 18(1), 33-36.
Luyten, F. P. et al., "Skeletal tissue engineering: opportunities and challenges," *Best Pract. Res. Clin. Rheumatol.*, Dec. 2001, 15(5), 759-769.

(56) References Cited

OTHER PUBLICATIONS

MacDonald, R.J., "Expression of the pancreatic elastase I gene in transgenic mice," *Hepatology*, 1987, 7(1), 42S-51S.

Marx, W.F., et al., "Endovascular treatment of experimental aneurysms by use of biologically modified embolic devices: coil-mediated intraaneurysamal delivery of fibroblast tissue allografts," *Am. J. Neuroradiol.*, 2001, 22, 323-333.

Mason, A.J., et al., "The hypogonadal mouse: reproductive functions restored by gene therapy," *Science*, 1986, 234, 1372-1378.

Mayer-Proschel, M., et al., "Isolation of lineage-restricted neuronal precursors from multipotent neuroepithelial stem cells," *Neuron.*, 1997, 19, 773-785.

McDonald, J.A., et al., "Diminished responsiveness of male homosexual chronic hepatitis B virus carriers with HTLV-III antibodies to recombinant α-interferon," *Hepatology*, 1987, 7(4), 719-723.

Medicetty, S. et al., "Transplantation of Human Umbilical Cord Matrix Stem Cells Alleviates Apomorphine-Induced Rotations in Parkinsonian Rats", 2003, XP-002383776, 1 page.

Medline Plus Online Medical Dictionary, definitions of "undifferentiated," and "differentiate," and "differentiation." Retrieved online Mar. 6, 2007. URL:www.nlm.nih.gov/medlineplus/mplusdictionary.html.

Merx, M. W. et al., "Transplantation of human umbilical vein endothelial cells improves left ventricular function in a rat model of myocardial infarction," *Basic Res. Cardiol.*, 2005, 100, 208-216.

Messina, D. J., et al., "Comparison of pure and mixed populations of human fetal-derived neural progenitors transplanted into intact and adult rat brain," *Exper. Neurol.*, 2003, 184, 816-829.

Messina, D.J., et al., "Comparison of pure and mixed populations of human fetal-derived neural progenitors transplanted into intact and adult rat brain," *Exper. Neurol.*, 2003, 184, 816-829.

Mitchell,, K. E. et al., "Matrix cells from Wharton's jelly form neurons and glia," *Stem Cells*, 2003, 21, 50-60.

Moll, S., et al., "Monitoring warfarin therapy in patients with lupus anticoagulants," *Ann. Intern. Med.*, 1997, 127(3), 177-185.

Mombaerts, P. et al., "Creation of a large genomic deletion at the T-cell antigen receptor β-subunit locus in mouse embryonic stem cells by gene targeting," *Proc. Nat. Acad. Sci. USA*, 1991, 88, 3084-3087.

Morgenstern, J. P., et al., "Advanced mammalian gene transfer: high titre retroviral vectors with multiple drug selection markers and a complementary helper-free packaging cell line," *Nucleic Acids Res.*, 1990, 18(12), 3587-3596.

Morishima, Y. et al., "The clinical significance of human leukocyte antigen (HLA) allele compatibility in patients receiving a marrow transplant from serologically HLA-A, HLA-B, and HLA-DR matched unrelated donors," *Blood*, 2002, 99(11), 4200-4206.

Moulder, J. E., "Pharmacological intervention to prevent or ameliorate chronic radiation injuries," *Semin. Radiat. Oncol.*, 2003, 13, 73-84.

Nakamura, T., et al., "Ocuar surface reconstruction using cultivated mucosal epithelial stem cells," *Cornea*, 2003, 22(Supp. 1), S75-S80.

Nicosia, R.F., et al., "Modulation of microvascular growth and morphogenesis by reconstituted basement membrane gel in three-dimensional cultures of rat aorta: a comparative study of angiogenesis in matrigal, collagen, fibrin, and plasma clot," in *Vitro Cell Dev. Biol.*, 1990, 26, 119-128.

Nishida K., et al., "Functional bioengineered corneal epithelial sheet grafts from corneal stem cells expanded ex vivo on a temperature-responsive cell culture surface," *Transplantation*, 2004, 77(3), 379-385.

Nixon, P.J., et al., "The contribution of cone responses to rat electroretinograms," *Clin. Experiment Ophthalmol.*, 2001, 29(3), 193-196.

Nork, T. M. et al., "Swelling and Loss of Photoreceptors in Chronic and Experimental Glaucomas," *Arch. Ophthalmol.*, 2000, 118, 235-245.

Nusinowitz, S., et al., "Rod multifocal electroretinograms in mice," *Invest Ophthalmol Vis. Sci.*, 1999, 40(12), 2848-2858.

Oh, S.-H., et al., "Hepatocyte growth factor induces differentiation of adult rat bone marrow cells into a hepatocyte lineage in vitro," *Biochem. & Biophys. Res. Comm.*, 2000, 279, 500-504.

Okumoto, K., et al., "Differentiation of bone marrow cells into cells that express liver-specific genes in vitro: implication of the notch signals in differentiation," *Biochem. & Biophys. Res. Commun.*, 2003, 304, 691-695.

Orlic, D., et al., "Stem cells for myocardial regeneration," *Circ. Res.*, 2002, 91, 1092-1102.

Ornitz, D.M., et al., "Elastase I promoter directs expression of human growth hormone and SV40 T antigen genes to pancreatic acinar cells in transgenic mice," *Cold Spring Harbor Symp. Quant. Biol.*, 1985, vol. L, 399-409.

Osborne, N.N., et al., "Some current ideas on the pathogenesis and the role of neuroprotection in glaucomatous optic neuropathy," *Eur. J. Ophthalmol.*, 2003, 13(Supp. 3), S19-S26.

Palu, G. et al., "In pursuit of new developments for gene therapy of human disease," *J. Biotechnol.*, Feb. 1999, 68(1), 1-13.

Petersdorf, E. W., "HLA matching in allogeneic stem cell transplantation," *Curr. Op. Hematol.*, 11(6), 386-391.

Phipps, J. A. et al., "Paired-flash identification of rod and cone dysfunction in the diabetic rat," *Investigative Ophthalmology & Visual Science*, 2004, 45(12), 45924600.

Pittenger, M. F. et al., "Multilineage potential of adult human mesenchymal stem cells," *Science*, 1999, 284, 143-147 and seven pages of online supplementary material.

Rabbany, S.Y., et al., "Molecular pathways regulating mobilization of marrow-derived stem cells for tissue revascularization," *TRENDS in Molecular Med.*, 2003, 9(3), 109-117.

Rafii, S., et al., "Therapeutic stem and progenitor cell transplantation for organ vascularization and regeneration," *Nature Med.*, 2003, 9(6), 702-712.

Raman-Cueto, A., et al., "Functional recovery of paraplegic rats and motor axon regeneration in their spinal cords by olfactory ensheathing glia," *Neuron*, 2000, 25, 425-435.

Readhead, C., et al., "Expression of a myelin basic protein gene in transgenic shiverer mice: correction of the dysmyelinating phenotype," *Cell*, 1987, 48, 703-712.

Refaie, A., et al., "Experimental islet cell transplantation in rats: optimization of the transplantation site," *Trans. Proc.*, 1998, 30, 400-403.

Reubinoff, B.E., et al., "Neural progenitors from human embryonic stem cells," *Nature Biotechnology*, 2001, 19, 1134-1140.

Reyes, M., et al., "Purification and ex vivo expansionof postnatal human marrow mesodermal progenitor cells," *Blood*, 2001, 98(9), 2615-2625.

Rezai, KA., et al., "Iris pigment epithelium transplantation," *Graefes Arch. Clin. Ophthalmol.*, 1997, 235, 558-562.

Rickard, D.J., et al., "Induction of rapid osteoblast differentiation in rat bone marrow stromal cell cultures by dexamethasone and BMP-2," *Dev. Biol.*, 1994, 161, 218-288.

Rios, M., et al., "Catecholamine Synthesis is Mediated by Tyrosinase in the Absence of Tyrosine Hydroxylase," *J. Neurosci.*, 1999, 3519-3526.

Romanov, Y.A., et al., "Searching for alternative sources of postnatal human mesenchymal stem cells," *Stem Cells*, 2003, 21, 105-110.

Rosen, E.M., et al., "HGF/SF in angiogenesis," *Ciba Found. Symp.*, 1997, 212, 215-229.

Rutherford, A., et al., "Eyeing-up stem cell transplantation," *Trends in Molecular Medicine*, 2003, 7(1), p. 11.

Sahn, D.J., et al., "Recommendations regarding quantitation in M-Mode echocardiography: results of a survey of echocardiographic measurements," *Circulation*, 1978, 58, 1072-1083.

Sakariassen, K.S., et al., "Methods and models to evaluate shear-dependent and surface reactivity-dependent antithrombotic efficacy," *Thromb. Res.*, 2001, 104, 149-174.

Salcedo, R. et al., "Human endothelial cells express CCR2 and respond to MCP-1: direct role of MCP-1 in angiogenesis and tumor progression," *Blood*, 2000, 96(1), 34-40.

Salgado, A. J. et al., "Bone Tissue Engineering: State of the Art and Future Trends," *Macromol. Biosci.*, Aug. 2004, 4, 743-765.

(56) References Cited

OTHER PUBLICATIONS

Sauve, Y., et al., "The relationship between full field electroretinogram and perimetry-like visual thresholds in RCS rats during photoreceptor degeneration and rescue by cell transplants," *Vision Res.*, 2004, 44(1), 9-18.

Schraermeyer, U., et al., "Subretinally transplanted embryonic stem cells rescue photoreceptor cells from degeneration in the RCS rats," *Cell Transplantation*, 2001, 10, 673-680.

Schreuder, G. M. et al., "The HLA dictionary 1999: a summary of HLA-A, -B, -C, -DRB1/3/4/5, -DQB1 alleles and their association with serologically defined HLA-A, -B, -C, -DR and -DQ antigens," *Tissue Antigens*, 1999, 54(4), 490-437.

Schwartz, R.E., et al., "Multipotent adult progenitor cells from bone marrow differentiate into functional hepatocyte-like cells," *J. of Clin. Invest.*, 2002, 109(10), 1291-1302.

Sebire, G., et al., "In vitro production of IL-6,IL-1 β, and tumor necrosis factor-alpha by human embryonic microglial and neural cells," *J. Immunol.*, 1993, 150, 1517-1523.

Sethe, S. et al., "Aging of mesenchymal stem cells," *Ageing Research Reviews*, 2006, 5, 91-116.

Shani, M., "Tissue-specific expression of rat myosin light-chain 2 gene in transgenic mice," *Nature*, 1985, 314, 283-286.

Shimizu, T., et al., "Cell sheet engineering for myocardial tissue reconstruction," *Biomaterials*, 2003, 24, 2309-2316.

Siminoff, R., et al., "Properties of reptilian cutaneous mechanoreceptors," *Exp. Neurol.*, 1968, 20(3), 403-414.

Sordillo, L.M., et al., "Culture of bovine mammary epithelial cells in D-valine modified medium: selective removal of contaminating fibroblasts," *Cell Biol. Int. Rep.*, 1988, 12, 355-364.

Storch, T.G., "Oxygen concentration regulates 5-azacytidine-induced myogenesis in $C_3H/10T1/2$ cultures," *Biochim. Biophys. Acta*, 1990, 1055, 126-129.

Street, C.N., et al., "Stem cells: a promising source of pancreatic islets for transplantation in type 1 diabetes," *Curr. Top Dev. Biol.*, 2003, 58, 111-136.

Svendsen, C.N., "The amazing astrocyte," *Nature*, 2002, 417, 29-32.

Svendsen, C.N., et al., "Long-term survival of human central nervous system progenitor cells transplanted into a rat model of Parkinson's disease," *Experim. Neurol.*, 1997, 148, 135-146.

Swift, G.H., et al., "Tissue-specific expression of the rat pancreatic elastase I gene in transgenic mice," *Cell*, 1984, 38, 639-646.

Taylor, D. A. et al., "Cardiac chimerism as a mechanism for self-repair: does it happen and if so to what degree?" *Circulation*, Jul. 2002, 106(1), 2-4.

Taylor, D. A. et al., "Regenerating functional myocardium: Improved performance after skeletal myoblast transplantation," *Nature Medicine*, Aug. 1998, 4(8), 929-933. Erratum in *Nature Medicine*, 4(10), 1200.

Thorsby, E. et al., "Role of HLA molecules in the induction of alloimmune responses: clinical significance in the cyclosporine era," *Transplant Proc.*, 2004, 36(2Suppl), 16S-21S.

Timmermans et al., "Stem cells for the heart, are we there yet?" *Cardiology*, 2003, 100(4), 176-185.

Tomita, M., et al., "Bone marrow-derived stem cells can differentiate into retinal cells in injured rat retina," *Stem Cells*, 2002, 20, 279-283.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001, 19, 408-418.

Tresco, P.A., et al., "Cellular transplants as sources for therapeutic agents," *Advanced Drug Delivery Reviews*, 2000, 42, 3-27.

Tsonis, P.A., et al., "Lens and retina regeneration: transdifferentiation, stem cells and clinical applications," *Experim. Eye Res.*, 2004, 78, 161-172.

Turner D, "The human leucocyte antigen (HLA) system," *Vox Sang.*, 2004, 87(Suppl1), 87-90.

Turner, J.F., "Inherited retinal dystrophy in the RCS rat: prevention of photoreceptor degeneration by pigment epithelial cell transplantation," *Exp. Eye Res.*, 1988, 47, 911-917.

Tusher, V.G., et al., "Significance analysis of microarrays applied to the ionizing radiation response," *Proc. Natl. Acad. Sci. USA*, 2001, 98(9), 5116-5121.

Unigene entry for Hs.522632, Homo sapiens TMP metallopeptidase inhibitor 1 (TIMP1), printed from http://www.ncbi.nlm.nih.gov/UniGene on Oct. 12, 2006.

Vajsar, J. et al., "Walker-Warburg syndrome," *Orphanet Journal of Rare Diseases*, 2006, 1, 29.

Van Hoffelen, S.J., et al., "Incorporation of murine brain progenitor cells into the developing mammalian retina," *Invest. Ophthalmol. Vis. Sci.*, 2003, 44, 426-434.

Vassliopoulos, G., et al., "Transplanted bone marrow regenerates liver by cell fusion," *Nature*, 2003, 422, 901-904.

Verma, I. M. et al., "Gene therapy—promises, problems and prospects," *Nature*, Sep. 1997, 389(6648), 239-242.

Vermot-Desroches, C. et al., "Heterogeneity of antigen expression among human umbilical cord vascular endothelial cells: identification of cell subsets by co-expression of haemopoietic antigens," *Immunol. Lett.*, 1995, 48, 1-9.

Villegas-Perez, M.P., et al., "Influences of peripheral nerve grafts on the survival and regrowth of axotomized retinal ganglion cells in adult rats," *J. of Neurosci.*, 1988, 8(1), 265-280.

Von Koskull, H., et al., "Induction of cytokeratin expression in human mesenchymal cells," *J. Cell Physiol.*, 1987, 133, 321-329.

Walboomers, X.F., et al., "Cell and tissue behavior on micro-grooved surfaces," *Odontology*, 2001, 89, 2-11.

Wang, D., et'al., "Synthesis and characterization of a novel degradable phosphate-containing hydrogel," *Biomaterials*, 2003, 24, 3969-3980.

Wang, X., et al., "Cell fusion is the principal source of bone-marrow-derived hepatocytes," *Nature*, 2003, 422, 897-900.

Wegman, A., et al., "Nonsteroidal anti-inflammatory drugs or acetaminophen for osteoarthritis of the hip or knee? A synstematic review of evidence and guidelines," *J. Rheumatol.*, 2004, 31, 344-354.

Weiss, M. L. et al., "Human umbilical cord matrix stem cells: preliminary characterization and effect of transplantation in a rodent model of Parkinson's disease," *Stem Cells*, 2006, 24, 781-792.

Weiss, M.L., et al., "Transplantation of porcine umbilical cord matrix cells into the rat brain," *Exp. Neur.*, 2003, 182, 288-299.

Wobus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539.

Woodbury, D., et al., "Adult rat and human bone marrow stromal cells differentiate into neurons," *J. of Neurosci. Res.*, 2000, 61, 364-370.

Wulf, G. G. et al., "Mesengenic Progenitor Cells Derived From Human Placenta," *Tissue Engineering*, Larchmont, NY, Jul. 2004, 10(7/8), 1136-1147.

Xu, C., et al., "Characterization and enrichment of cardiomyocytes derived from human embryonic stem cells," *Circ. Res.*, 2002, 91, 501-508.

Xu, Y., et al., "Dopamine, in the presence of tyrosinase, covalently modifies and inactivates tyrosine hydroxylase," *J. Neurosci. Res.*, 1998, 54(5), 691-697 (Abstract, 3 pages).

Yang, H., et al., "Region-specific differentiation of neural tube-derived neuronal restricted progenitor cells after heterotopic transplantation," *PNAS*, 2000, 97(24), 13366-13371.

Ye, Q. et al., "Recovery of Placental-Derived Adherent Cells with Mesenchymal Stem Cell Characteristics", 2001, 98(11), 147B, XP-009026843.

Yip, H.K., et al., "Axonal regeneration of retinal ganglion cells: effect of trophic factors," *Prog. Retin Eye Res.*, 2000, 19(5), 559-575.

Yokoo, T. et al., "Stem cell gene therapy for chronic renal failure," *Curr Gene Ther.*, 2003, 3, 387-394.

Yu, M., et al., "Mid-trimester fetal blood-derived adherent cells share characteristics similar to mesenchymal stem cells but full-term umbilical cord blood does not," *British J. of Haematology*, 2004, 124, 666-675.

Zangani, D., et al., "Multiple differentiation pathways of rat mammary stromal cells in vitro: acquisition of a fibroblast, adipocyte or endothelial phenotype in dependent on hormonal and extracellular matrix stimulation," *Differentiation*, 1999, 64, 91-101.

(56) References Cited

OTHER PUBLICATIONS

Zeng, B.Y., et al., "Regenerative and other responses to injury in the retinal stump of the optic nerve in adult albino rats: transaction of the intracranial optic nerve," *J. Anat.*, 1995, 186, 495-508.

Zhang, S.-C., et al., "In vitro differentiation of transplantable neural precursors from human embryonic stem cells," *Nature Biotechnology*, 2001, 19, 1129-1133.

Zimmermann, S. et al., "Lack of telomerase activity in human mesenchymal stem cells," *Leukemia*, 2003, 17, 1146-1149.

Zuloff-Shani, A. et al., "Macrophage suspensions prepared from a blood unit for treatment of refractory human ulcers," *Transfus Apheresis Sci.* 2004, 30(2), 163-167.

Le Blanc, K. et al., "Treatment of Severe Acute Graft-Versus-Host Disease With Third Party Haploidentical Mesenchymal Stem Cells," *Lancet*, May 1, 2004, 363(9419), 1439-1441.

Carter, D. et al., "Characterization of MSC Potential to Treat GVHD Using Molecular Markers Linked to MSC-Mediated Immunosuppression in Vitro," *Blood*, Nov. 2005, 106(11) part 2, Abstract No. 4322, p. 160B.

Li Chang Dong et al., "Mesenchymal Stem Cells Derived From Human Placenta Suppress Allogeneic Umbilical Cord Blood Lymphocyte Proliferation," *Cell Research*, Jul. 2005, 15(7), 539-547.

Zhang, Y. et al., "Comparison of Mesenchymal Stem Cells from Human Placenta and Bona Marrow," *Chinese Medical Journal*, 2004, 117(6), 882-887.

Panepucci, R.A. et al., "Comparison of Gene Expression of Umbilical Cord Vein and Bone Marrow-Derived Mesenchymal Stem Cells," *Stem Cells*, 2004, 22(7), 1263-1278.

Bartholomew, A. et al., "Mesenchymal stem cells suppress lymphocyte proliferation in vitro and prolong skin graft survival in vivo," *Exp Hematol*, 2002, 30:42-48.

Frassoni, F. et al., "Expanded mesenchymal stem cells (MSC), co-infused with HLA identical hematopoietic stem cell transplants, reduce acute and chronic graft-versus-host disease: a matched pair analysis", *Bone Marrow Transplantation*, 2002, 29 (suppl. 2) S2.

Liu, F. et al., "Purification of placenta-eluted gamma globulins and their strong effect against graft-versus host reactions in vitro and in vivo," *Int. J Hematol*, 2005; 82:162-8.

Menu, E. et al., "Immunoactive products of human placenta IV. Immunoregulatory factors obtained from cultures of human placenta inhibit in vivo local and systemic allogeneic and graft versus-host reactions in mice," *J Reprod Immunol*, 1991;20:195-204.

Stein, K. et al., "Umbilical cord blood (UCB) serum from caesarean, as compared to vaginal deliveries exerts a potent immunosuppressive effect on adult lymphocyte proliferation," *Blood*, 2000; 96: 45b (Abstract 3859).

Zhang, Y. et al., "Human placenta-derived mesenchymal progenitor cells support culture expansion of long-term culture initiating cells from cord blood $CD34^+$ cells," *Exp Hematol*, 2004;32: 657-64.

In the U. S. Patent and Trademark Office, Non-Final Office Action in re: U.S. Appl. No. 11/481,456 dated Feb. 3, 2011, 10 pages.

In the U. S. Patent and Trademark Office, Non-Final Office Action in re: U.S. Appl. No. 11/481,481 dated Feb. 3, 2011, 10 pages.

In the U. S. Patent and Trademark Office, Non-Final Office Action in re: U.S. Appl. No. 12/389,305 dated Feb. 8, 2011, 14 pages.

In the U. S. Patent and Trademark Office, Non-Final Office Action in re: U.S. Appl. No. 11/481,480 dated Feb. 3, 2011, 10 pages.

In the U.S. Patent and Trademark Office, Final Office Action in re: U.S. Appl. No. 10/877,446 dated Nov. 2, 2011, 12 pages.

In the U.S. Patent and Trademark Office, Final Office Action in re: U.S. Appl. No. 12/389,305 dated Oct. 12, 2011, 12 pages.

In the U.S. Patent and Trademark Office, Final Office Action in re: U.S. Appl. No. 12/429,849 dated Mar. 20, 2012, 9 pages.

Draper et al., "Surface Antigens of Human Embryonic Stem Cells: Changes Upon Differentiation in Culture," *J. Anat.*, 2002; 200:249-258.

Kusama et al., "Growth and morphogenesis of mouse prostate epithelial cells in collagen gel matrix culture" *Cell Biol Int Rep*, 1989; 13:569-575.

Makino, S. et al.,"Cardiomyocytes can be generated from marrow stromal cells in vitro," *J. Clin. Invest.*, 1999; 103:697-705.

Seaver et al. "The chick oviduct in tissue culture. I. Initial characterization of growing primary oviduct tissue cultures," *Exp. Cell Res.*, 1984; 55: 241-251.

Wang, Y. et al., "Enhanced Recovery of Hematopoietic Progenitor and Stem Cells from Cultivated, Postpartum Human Placenta," *Blood*, 2001; 98(11): 183a (Abstract 769).

In the U. S. Patent and Trademark Office, Final Office Action in re: U.S. Appl. No. 11/315,969, dated Dec. 23, 2008, 11 pages.

In the U. S. Patent and Trademark Office, Final Office Action in re: U.S. Appl. No. 11/321,864, dated Jan. 8, 2009, 10 pages.

In the U. S. Patent and Trademark Office, Final Office Action in re: U.S. Appl. No. 11/321,863, dated Feb. 12, 2009, 14 pages.

In the U. S. Patent and Trademark Office, Non-Final Office Action in re: U.S. Appl. No. 11/481,481, dated Mar. 20, 2009, 12 pages.

In the U. S. Patent and Trademark Office, Advisory Action in re: U.S. Appl. No. 11/315,969 dated Sep. 29, 2009, 9 pages.

In the U. S. Patent and Trademark Office, Advisory Action in re: U.S. Appl. No. 11/322,372 dated May 12, 2009, 10 pages.

In the U. S. Patent and Trademark Office, Final Office Action in re: U.S. Appl. No. 10/877,445 dated Aug. 25, 2009, 18 pages.

In the U. S. Patent and Trademark Office, Final Office Action in re: U.S. Appl. No. 11/321,863 dated Aug. 7, 2009, 11 pages.

In the U. S. Patent and Trademark Office, Final Office Action in re: U.S. Appl. No. 11/321,864 dated Aug. 17, 2009, 13 pages.

In the U. S. Patent and Trademark Office, Non-Final Office Action in re: U.S. Appl. No. 11/317,574 dated Dec. 28, 2009, 26 pages.

In the U. S. Patent and Trademark Office, Non-Final Office Action in re: U.S. Appl. No. 11/321,863 dated Jan. 7, 2010, 13 pages.

In the U. S. Patent and Trademark Office, Non-Final Office Action in re: U.S. Appl. No. 11/321,864 dated Jan. 27, 2010, 12 pages.

In the U. S. Patent and Trademark Office, Non-Final Office Action in re: U.S. Appl. No. 11/315,969 dated Jan. 27, 2010, 12 pages.

In the U. S. Patent and Trademark Office, Non-Final Office Action in re: U.S. Appl. No. 11/315,943 dated Feb. 19, 2010, 13 pages.

In the U. S. Patent and Trademark Office, Final Office Action in re: U.S. Appl. No. 11/316,104 dated Mar. 24, 2010, 12 pages.

In the U. S. Patent and Trademark Office, Non-Final Office Action in re: U.S. Appl. No. 11/481,456 dated May 14, 2010, 9 pages.

In the U. S. Patent and Trademark Office, Non-Final Office Action in re: U.S. Appl. No. 11/481,481 dated May 13, 2010, 9 pages.

In the U. S. Patent and Trademark Office, Final Office Action in re: U.S. Appl. No. 11/315,897 dated May 14, 2010, 13 pages.

In the U. S. Patent and Trademark Office, Non-Final Office Action in re: U.S. Appl. No. 11/481,480 dated May 17, 2010, 10 pages.

In the U. S. Patent and Trademark Office, Final Office Action in re: U.S. Appl. No. 10/877,445 dated Jul. 8, 2010, 20 pages.

In the U. S. Patent and Trademark Office, Non-Final Office Action in re: U.S. Appl. No. 10/876,998 dated Aug. 3, 2010, 14 pages.

In the U. S. Patent and Trademark Office, Final Office Action in re: U.S. Appl. No. 11/321,863 dated Aug. 17, 2010, 15 pages.

In the U. S. Patent and Trademark Office, Final Office Action in re: U.S. Appl. No. 11/321,864 dated Aug. 31, 2010, 7 pages.

In the U. S. Patent and Trademark Office, Final Office Action in re: U.S. Appl. No. 11/315,969 dated Aug. 31, 2010, 6 pages.

In the U. S. Patent and Trademark Office, Final Office Action in re: U.S. Appl. No. 11/322,372 dated Aug. 31, 2010, 11 pages.

In the U. S. Patent and Trademark Office, Non-Final Office Action in re: U.S. Appl. No. 11/316,104 dated Sep. 21, 2010, 13 pages.

In the U. S. Patent and Trademark Office, Final Office Action in re: U.S. Appl. No. 11/317,574 dated Oct. 6, 2010, 16 pages.

In the U. S. Patent and Trademark Office, Non-Final Office Action in re: U.S. Appl. No. 12/054,718 dated Sep. 29, 2010, 18 pages.

In the U. S. Patent and Trademark Office, Non-Final Office Action in re: U.S. Appl. No. 11/322,372 dated Jan. 21, 2010, 10 pages.

In the U. S. Patent and Trademark Office, Final Office Action in re: U.S. Appl. No. 11/481,481 dated Sep. 18, 2009, 11 pages.

In the U. S. Patent and Trademark Office, Advisory Action in re: U.S. Appl. No. 11/315,897 dated Jun. 30, 2009, 3 pages.

In the U. S. Patent and Trademark Office, Non-Final Action in re: U.S. Appl. No. 11/315,897 dated Sep. 2, 2009, 12 pages.

(56) References Cited

OTHER PUBLICATIONS

In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
Bain et al., "The Development of Large Immature Mononuclear Cells in Mixed Leukocyte Cultures," *Blood*, 1964, 23(1):106-116.
Bishara et al., "Cytokine Production in Human Mixed Leukocyte Reactions Performed in Serum-Free Media," *Journal of Immunological Methods*, 1998; 215:187-190.
Cho et al, "Immunogenicity of Umbilical Cord Tissue-Derived Cells," *Blood*, 2008; 111(1):430-438.
Diao et al, "Human Umbilical Cord Mesenchymal Stem Cells: Osteogenesis In Vivo as Seed Cells for Bone Tissue Engineering," *J. BioMed Mater Res.*, 2009; 91A:123-131.
Engleman et al., "Autologous Mixed Lymphocyte Reaction in Patients with Hodgkin's Disease," *J. Clin. Invest.*, 1980; 66:149-158.
Gould et al., "Direct and Indirect Recognition: The Role of MHC Antigens in Graft Rejection," *Immunology Today*, 1999; 20(2):77-82.
In the U.S. Patent and Trademark Office, Non-Final Office Action in re: U.S. Appl. No. 11/317,574 dated Jul. 22, 2013, 29 pages.
Baksh, D. et al., "Comparison of proliferative and multilineage differentiation potential of human mesenchymal stem cells derived from umbilical cord and bone marrow." Stem Cells, 2007; 25: 1384-1392.
Covas, D.T. et al., "Isolation and culture of umbilical vein mesenchymal stem cells." Brazilian Journal of Medical and Biological Research, 2003; 36: 1179-1183.
Kestendjieva, S. et al., "Characterization of mesenchymal stem cells isolated from the human umbilical cord." Cell Biology International, 2008; 32: 724-732.
Nehlin et al., "Immunogenicity and Immune-Modulating Properties of Human Stem Cells", Stem Cells in Clinical Research, 2011.
In the U. S. Patent and Trademark Office, Non-Final Office Action in re: U.S. Appl. No. 10/876,998 dated Feb. 11, 2014, 14 pages.
In the U. S. Patent and Trademark Office, Non-Final Office Action in re: U.S. Appl. No. 11/316,104 dated Mar. 14, 2014, 11 pages.
In the U.S. Patent and Trademark Office, Final Office Action in re: U.S. Appl. No. 11/317,574 dated Feb. 3, 2014, 16 pages.
In the U.S. Patent and Trademark Office, Final Office Action in re: U.S. Appl. No. 11/317,574 dated Feb. 3, 2014, 12 pages.
In the U.S. Patent and Trademark Office, Final Office Action in re: U.S. Appl. No. 11/321,864 dated Nov. 3, 2014, 10 pages.
In the U.S. Patent and Trademark Office, Final Office Action in re: U.S. Appl. No. 10/876,998 dated Dec. 16, 2014, 19 pages.
In the U.S. Patent and Trademark Office, Final Office Action in re: U.S. Appl. No. 11/315,969 dated Dec. 18, 2014, 30 pages.
In the U.S. Patent and Trademark Office, Final Office Action in re: U.S. Appl. No. 11/321,863 dated Jan. 31, 2014, 17 pages.
In the U.S. Patent and Trademark Office, Final Office Action in re: U.S. Appl. No. 12/389,305 dated Aug. 6, 2014, 57 pages.
In the U.S. Patent and Trademark Office, Non-Final Office Action in re: U.S. Appl. No. 11/317,574 dated Jul. 11, 2013, 29 pages.
In the U.S. Patent and Trademark Office, Non-Final Office Action in re: U.S. Appl. No. 11/322,372 dated Jan. 16, 2014, 17 pages.
In the U.S. Patent and Trademark Office, Non-Final Office Action in re: U.S. Appl. No. 11/321,864 dated Jan. 29, 2014, 9 pages.
In the U.S. Patent and Trademark Office, Non-Final Office Action in re: U.S. Appl. No. 11/321,863 dated Jan. 31, 2014, 17 pages.
In the U.S. Patent and Trademark Office, Non-Final Office Action in re: U.S. Appl. No. 12/389,305 dated Mar. 6, 2014, 37 pages.
In the U.S. Patent and Trademark Office, Non-Final Office Action in re: U.S. Appl. No. 12/389,305 dated Mar. 21, 2014, 47 pages.
In the U.S. Patent and Trademark Office, Non-Final Office Action in re: U.S. Appl. No. 10/877,446 dated Mar. 21, 2014, 21 pages.
In the U.S. Patent and Trademark Office, Non-Final Office Action in re: U.S. Appl. No. 11/316,104 dated Mar. 21, 2014, 20 pages.
In the U.S. Patent and Trademark Office, Non-Final Office Action in re: U.S. Appl. No. 11/315,969 dated Mar. 21, 2014, 15 pages.
In the U.S. Patent and Trademark Office, Non-Final Office Action in re: U.S. Appl. No. 11/322,372 dated Nov. 25, 2014, 24 pages.
Bhatia, R. et al., "A clinically suitable ex vivo expansion culture system for LTC-IC and CFC using stroma-conditioned medium," *Exp Hematol.*, 1997; 25(9):980-91 (Abstract only).
Ciavarella, S. et al., "Umbilical Cord Mesenchymal Stem Cells: Role of Regulatory Genes in Their Differentiation to Osteoblasts," *Stem Cells and Development*, 2009; 18:1211-1220.
Deans, R.J. et al., "Mesenchymal stem cells: Biology and potential clinical uses," *Experimental Hematology*, 2000; 28: 875-884.
"Dulbecco's Modified Eagle's Medium (DME) Formulation." Sigma-Aldrich, available on line at <http://www.sigmaaldrich.com/life-science/cell-culture/learning-center/media-formulations/dme.printerview.html>. Accessed Mar. 17, 2014.
Hass, R. et al., "Different populations and sources of human mesenchymal stem cells (MSC): A comparison of adult and neonatal tissue-derived MSC," *Cell Communication and Signaling*, 2011; 9:12, p. 1-14.
Henderson, Gi, et al., "Inhibition of Placental Valine Uptake after Acute and Chronic Maternal Ethanol Consumption", *J Pharmacol Exp Therap*, 1981; 216:465-472.
Lonza (Cambrex), hMSC Human Mesenchymal Stem Cells, Lonza, 2014, http://www.lonza.com/products-services/bio-research/primary-and-stem-cells/adult-stem-cells-and-media/hmsc-mesenchymal-stem-cells.aspx; accessed Jan. 31, 2014.
Solomon, D. E., "An in vitro examination of extracellular matrix scaffold for use in wound healing," *Int. J. Path*, 2002, 93: 209-216.
Troyer, D. L. et al., "Concise Review: Wharton's Jelly-Derived Cells Are a Primitive Stromal Cell Population," *Stem Cells*, 2008; 26:591-599.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,445, dated Jul. 11, 2008, 12 pages.
In the U.S. Patent and Trademark Office, Non-Final Office Action in re: U.S. Appl. No. 10/877,445, dated Mar. 19, 2008, 12 pages.
In the U.S. Patent and Trademark Office, Final Office Action in re: U.S. Appl. No. 10/877,445, dated Nov. 5, 2007, 17 pages.
In the U.S. Patent and Trademark Office, Non-Final Office Action in re: U.S. Appl. No. 10/877,445, dated May 17, 2007, 20 pages.
In the U.S. Patent and Trademark Office, Final Office Action in re: U.S. Appl. No. 10/877,445, dated Sep. 11, 2006, 30 pages.

(56) References Cited

OTHER PUBLICATIONS

In the U.S. Patent and Trademark Office, Non-Final Office Action in re: U.S. Appl. No. 10/877,445, dated Nov. 21, 2005, 17 pages.
In the U.S. Patent and Trademark Office, Non-Final Office Action in re: U.S. Appl. No. 11/322,372, dated Sep. 3, 2008, 13 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 12 pages.
In the U.S. Patent and Trademark Office, Final Office Action in re: U.S. Appl. No. 11/297,778, dated Apr. 11, 2008, 9 pages.
In the U.S. Patent and Trademark Office, Non-Final Office Action in re: U.S. Appl. No. 11/297,778, dated Feb. 22, 2007, 8 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the United States Patent and Trademark Office, Final Office Action in re: U.S. Appl. No. 11/315,898, dated Sep. 16, 2008, 13 pages.
In the United States Patent and Trademark Office, Non-Final Office Action in re: U.S. Appl. No. 11/323,372, dated Sep. 3, 2008, 45 pages.
In the United States Patent and Trademark Office, Non-Final Office Action, in re: U.S. Appl. No. 11/297,156, dated Oct. 10, 2008, 36 pages.
In the United States Patent and Trademark Office, Non-Final Office Action in re: U.S. Appl. No. 11/317,574, dated Sep. 30, 2008, 28 pages.
In the United States Patent and Trademark Office, Non-Final Office Action in re: U.S. Appl. No. 10/951,357, dated Nov. 26, 2008, 25 pages.
In the United States Patent and Trademark Office, Non-Final Office Action in re: U.S. Appl. No. 11/315,943, dated Feb. 20, 2009, 17 pages.
In the U.S. Patent and Trademark Office, Final Office Action in re: U.S. Appl. No. 11/322,003 dated Feb. 13, 2009, 24 pages.
In the U.S. Patent and Trademark Office, Final Office Action in re: U.S. Appl. No. 10/876,998 dated Feb. 13, 2009, 18 pages.
In the U.S. Patent and Trademark Office, Final Office Action in re: U.S. Appl. No. 11/322,372 dated Feb. 13, 2009, 22 pages.
In the United States Patent and Trademark Office, Non-Final Office Action in re: U.S. Appl. No. 11/611,602, dated Mar. 3, 2009, 17 pages.
In the United States Patent and Trademark Office, Non-Final Office Action in re: U.S. Appl. No. 11/297,778, dated Mar. 9, 2009, 12 pages.
In the U.S. Patent and Trademark Office, Non-Final Office Action in re: U.S. Appl. No. 10/877,445, dated Mar. 19, 2009, 23 pages.
In the U.S. Patent and Trademark Office, Final Office Action in re: U.S. Appl. No. 11/315,897, dated Mar. 20, 2009, 21 pages.
In the U.S. Patent and Trademark Office, Non-Final Office Action in re: U.S. Appl. No. 11/481,480, dated Mar. 20, 2009, 50 pages.
In the U.S. Patent and Trademark Office, Non-Final Office Action in re: U.S. Appl. No. 11/481,456 dated Apr. 16, 2009, 50 pages.
In the U.S. Patent and Trademark Office, Non-Final Office Action in re: U.S. Appl. No. 11/317,574 dated Apr. 29, 2009, 29 pages.
In the U.S. Patent and Trademark Office, Final Office Action in re: U.S. Appl. No. 11/612,872 dated May 15, 2009, 7 pages.
In the U.S. Patent and Trademark Office, Non-Final Office Action in re: U.S. Appl. No. 10/877,446, dated Jun. 12, 2009, 16 pages.
Abbas, A. et al., *Cellular and Molecular Immunology*, 1991, p. 320.
Agbulut, O. et al., "Comparison of Human Skeletal Myoblasts and Bone Marrow-Derived CD133+ Progenitors for the Repair of Infarcted Myocardium," *Journal of the American College of Cardiology*, 2004; 44(2):458-463.
Aldskogius, H. et al., "Strategies for Repair of the Deafferented Spinal Cord," *Brain Res. Rev.*, 2002; 40:301-308.
Armulik, A. et al., "Endothelial/Pericyte Interactions," *Circ. Res.*, 2005; 97:512-523.
Aston, J. E., et al., "Repair of Articular Surfaces by Allografts of Articular and Growth-Plate Cartilage," *Journal of Bone and Joint Surgery*, 1986; 68-B(1):29-35.
Auda-Boucher et al., "Staging of the Commitment of Murine Cardiac Cell Progenitors," *Developmental Biology*, 2000, 214-225.
Bai, M., et al, "Dimerization of the Extracellular Calcium-sensing Receptor (CaR) on the Cell Surface of CaR-Transfected HEK293 Cells," *J. Biol Chem.*, 1998; 273(36): 23605-23610.
Bergers, G. et al., "The Role of Pericytes in Blood-Vessel Formation and Maintenance," *Neuro-Oncology*, 2005; 7:452-464.
Bhindi, R. et at, "Rat Models of Myocardial Infarction," *Thromb Haemost*, 2006; 96:602-610.
Blakemore et al., "Modelling Large Areas of Demyelination in the Rat Reveals the Potential and Possible Limitations of Transplanted Glial Cells for Remyelination in The CNS," *GLIA*, 2002; 38:155-168.
Bussolati et al., "Isolation of Renal Progenitor Cells from Adult Human Kidney," *American Journal of Pathology*, 2005; 166(2):545-555.
"Cell Lysis, p. 2" http://www.piercenet.com/objects/view.cfm?type=Page&ID=1904ED25-8FA4-475C-8068-C2EB13D5F4E7; accessed Aug. 7, 2008.
Chen, J. et al., "Therapeutic Benefit of Intravenous Administration of Bone Marrow Stromal Cells after Cerebral Ischemia in Rats," *Stroke*, 2001; 32(4):1005-1011.
Daley, G.Q. et al., "Realistic Prospects for Stem Cell Therapeutics," *Hematol.*, 2003; 398-418.
del Monte, F. et al., "Improvement in Survival and Cardiac Metabolism After Gene Transfer of Sarcoplasmic Reticulum $Ca^{2+}$-ATPase in a Rat Model of Heart Failure," *Circulation*, 2001;104:1424-1429.
Franc, S. et al., "Microfibrillar Composition of Umbilical Cord Matrix : Characterization of Fibrillin, Collagen VI and Intact Collagen V," *Placenta*, 1988; 19:95-104.
Gröhn, P. et al., "Collagen-Coated $BA^{2+}$-Alginate Microcarriers for the Culture of Anchorage-Dependent Mammalian Cells," *BioTechniques*, 1997; 22(5): 970-975.
Gupta, S. et al., "Isolation and Characterization of Kidney-Derived Stem Cells," *J. of Am. Soci. of Nephrol.*, 2006; 17(11):3028-3040.

(56) References Cited

OTHER PUBLICATIONS

Herrera, M.B. et al., "Mesenchymal Stem Cells Contribute to the Renal Repair of Acute Tubular Epithelial Injury," *Int. J. Mol. Med.*, 2004; 14(6):1035-1041.
Hill, D.P. et al., "Screening for Novel Pattern Formation Genes Using Gene Trap Approaches," *Methods in Enzymology*, 1993; 225:664-681.
Hishikawa, K. et al., "Musculin/MyoR is Expressed in Kidney Side Population Cells and Can Regulate Their Function," *Journal of Cell Biology*, 2005; 169(6):921-928.
Hoynowski, S.M. et al., "Characterization and Differentiation of Equine Umbilical Cord-Derived Matrix Cells," *Biochemical and Biophysical Research Communications*, 2007; 362:347-353.
In'T Anker, P., et al., "Isolation of Mesenchymal Stem Cells of Fetal or Maternal Origin from Human Placenta," *Stem Cells*, 2004; 22:1338-1345.
Jones, J. et al., "Insulin-Like Growth Factors and their Binding Proteins: Biological Actions," *Endocrine Review*, 1995; 16(1):3-34.
Jørgensen, N.R. et al., "Intercellular Calcium Signaling Occurs Between Human Osteoblasts and Osteoclasts and Requires Activation of Osteoclast P2X7 Receptors," *The Journal of Biological Chemistry*, (2002); 277(9): 7574-7580.
Kawata, M. et al., "Transcriptional Control of HLA-A,B,C Antigen in Human Placental Cytotrophoblast Isolated Using Trophoblast- and HLA-Specific Monoclonal Antibodies and the Fluorescence-Activated Cell Sorter," *J. Exp. Med.*, Sep. 1984; 160:633-651.
Kirschstein, R. et al., "Can Stem Cells Repair a Damaged Heart?" *Stem Cells: Scientific Progress and Future Research Directions*, 2001; 87-92.
Kisiday, J. et al., "Self-Assembling Peptide Hydrogel Fosters Chondrocyte Extracellular Matrix Production and Cell Division: Implications for Cartilage Tissue Repair," *PNAS*, 2002; 99(15):9996-10001.
Kurtz, A. et al., "Activity in Fetal Bovine Serum that Stimulates Erythroid Colony Formation in Fetal Mouse Livers is Insulinlike Growth Factor I," *J. Clin. Invest.*, 1985; 76;1643-1648.
Kushida, A., et al., "Decrease in Culture Temperature Releases Monolayer Endothelial Cell Sheets Together with Deposited Fibronectin Matrix from Temperature-Responsive Culture Surfaces," *J. of Biomedical Materials Research*, 1999; 45(4):355-362.
Li, Y. et al., "Intact, Injured, Necrotic and Apoptotic Cells after Focal Cerebral Ischemia in the Rat," *J. Neural. Sci.*, 1998; 156(2):119-132.
Li, Y. et al., "Ultrastructural and Light Microscopic Evidence of Apoptosis after Middle Cerebral Artery Occlusion in the Rat," *Am. J. Pathol.*, 1995; 146(5):1045-1051.
Lindvall, O. et al., "Stem Cell Therapy for Human Neurodegenerative Disorders—How to Make It Work," *Nature Medicine*, 2004;10(Suppl.):S42-S50.
Ma, L. et al., "Human Umbilical Cord Wharton's Jelly-Derived Mesenchymal Stem Cells Differentiation into Nerve-Like Cells," *Chinese Med. Jour.*, 2005; 118(23):1987-1993.
Ma, P.X . et al., "Synthetic Nano-Scale Fibrous Extracellular Matrix ," *J. Biomed Mater Res.*, 1999; 46(1):60-72.
Mackay, A.M. et al., "Chondrogenic Differentiation of Cultured Human Mesenchymal Stem Cells From Marrow," *Tissue Engineering*, 1998; 4(4):415-428.
Maeshima, A. et al., "Adult Kidney Tubular Cell Population Showing Phenotypic Plasticity, Tubulogenic Capacity, and Integration Capability into Developing Kidney," *Journal of American Society of Nephrology*, 2006; 17(1):188-198.
Melero-Martin, J. et al., "Optimal In-Vitro Expansion of Chondroprogenitor Cells in Monolayer Culture," *Biotechnology and Bioengineering*, 2006; 93(3):519-533.
Merriam-Webster Medline Plus Online Medical Dictionary, definitions of "iliac", "ilium" ileal/ileac and "ileum". [online] [retrieved on Feb. 12, 2008]. Retrieved from the Internet: URL://www.nlm.nih.gov/medlineplus/mplusdictionary.html.
Merriam-Webster Online Dictionary 10$^{th}$ Edition, Definition of "Scaffold" [retrieved on Sep. 12, 2008].
Morigi, M. et al., "Mesenchymal Stem Cells are Renotropic, Helping to Repair the Kidney and Improve Function in Acute Renal Failure," *J. Am. Soc. Nephrol.*, 2004; 15(7):1794-1804.
Nishishita, T. et al., "A Potential Pro-Angiogenic Cell Therapy With Human Placenta-Derived Mesenchymal Cells," *Biochemical and Biophysical Research Communications*, 2004; 325:24-31.
Pera, M.F. et al., "Human Embryonic Stem Cells", *J. Cell Science*, 2000; 113:5-10.
Pisharodi, M. et al., "An Animal Model for Neuron-Specific Spinal Cord Lesions by the Microinjection of N-Methylaspartate, Kainic Acid, and Quisqualic Acid," 1985; *Appl. Neurophysiology* 48:226-233.
Pittenger, M.F. et al., "Mesenchymal Stem Cells and Their Potential as Cardiac Therapeutics," *Circ. Res.*, 2004; 95:9-20.
Plaia, T., et al., "Characterization of a New Nih-Registered Variant Human Embryonic Stem Cell Line, BG01V: A Tool for Human Embryonic Stem Cell Research," *Stem Cells*, 2006: 24(3): 531-546.
Pountos, I. et al., "Mesenchymal Stem Cell Tissue Engineering: Techniques for Isolation, Expansion and Application," *Injury*, 2007; 38(Supp. 4):S23-33.
Quaini, F. et al., "Chimerism of the Transplanted Heart," *NEJM*, 2002; 346:5-15.
Rahman, Z. et al., "Isolation and Primary Culture of Urothelial Cells from Normal Human Bladder," *Urol. Research*, 1987; 15:315-320.
Rehman, J. et al., "Secretion of Angiogenic and Antiapoptotic Factors by Human Adipose Stromal Cells," *Circulation*, 2004; 109:1292-1298.
Roskams, A.J. et al., "Directing Stem Cells and Progenitor Cells on the Stage of Spinal Cord Injury," *Exp. Neurol.*, 2005; 193:267-272.
Russo, E., "Cultivating Policy from Cell Types," *The Scientist*, 2001; 15(11):6 (printout is numbered 1-6).
Schouten, J.W. et al., "A Review and Rationale for the Use of Cellular Transplantation as a Therapeutic Strategy for Traumatic Brain Injury," *Journal of Neurotrauma*, 2004; 21(11):1501-1538.
Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.
Song, H. et al., "Astroglia Induce Neurogenesis From Adult Neural Stem Cells," *Nature*, 2002; 417(6884):39-44.
Tao, W., "Application of Encapsulated Cell Technology for Retinal Degenerative Disease", *Expert. Opin. Biol. Ther.*, 2006; 6(7): 717-726.
Toma, C. et al., "Human Mesenchymal Stem Cells Differentiate to a Cardiomyocyte Phenotype in the Adult Murine Heart," *Circulation* 2002; 105:93-98.
Ulloa-Montoya, F. et al., "Culture Systems for Pluripotent Stem Cells," *Journal of Bioscience and Bioengineering*, 2005; 100(1):12-27.
Urbich, C. et al., "Endothelial Progenitor Cells Characterization and Role in Vascular Biology,", *Circ. Res.*, 2004; 95:343-353.
Villegas-Perez, M.P. et al., "Rapid and Protracted Phases of Retinal Ganglion Cell Loss Follow Axotomy in the Optic Nerve of Adult Rats," *J. Neurobiology*, 1993; 24(1):23-36.
Wenning, G.K. et al., "Neural Transplantation in Animal Models of Multiple System Atrophy: A Review," *J. Nueral Transm.*, 1999; Suppl.(55):103-113.
Wikipedia, Definition of "Iliac crest" provided by Wikipedia, the free encyclopedia; retrieved from the Internet at URL: http://en.wikipedia.org/wiki/Iliac_crest; downloaded on Dec. 18, 2007.
Wolford, L.M. et al., "Considerations in Nerve Repair," *BUMC Proceedings*, 2003; 16:152-156.
Xu, A. et al.,"Soft, Porous Poly(D,L lactide-co-glycotide) Microcarriers Designed for Ex Vivo Studies and for Transplantation of Adherent Cell Types including Progenitors," *Annals of the New York Academy of Sciences*, 2001, vol. 944: 144-159.

(56) References Cited

OTHER PUBLICATIONS

Yamashima, T., "Implication of Cysteine Proteases Calpain, Cathepsin and Caspase in Ischemic Neuronal Death of Primates," *Progress in Neurobiology*, 2000; 62:273-295.

Yang, C. et al., "Enhancement of Neovascularization With Cord Blood CD133+ Cell-Derived Endothelial Progenitor Cell Transplantation," *Thrombosis and Haemostasis*, Jun. 2004; 91(6):1202-1212.

Zhang, X. et al., "Efficient Adeno-Associated Virus-Mediated Gene Expression in Human Placenta-Derived Mesenchymal Cells," *Microbiol. Immunol.*, 2003; 47(1):109-116.

* cited by examiner

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 1
gagaaatcca aagagcaaat gg                                            22

<210> SEQ ID NO 2
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 2
agaatggaaa actggaatag g                                             21
```

```
<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
tcttcgatgc ttcggattcc                                               20

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 4
gaattctcgg aatctctgtt g                                             21

<210> SEQ ID NO 5
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 5
ttacaagcag tgcagaaaac c                                             21

<210> SEQ ID NO 6
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 6
agtaaacatt gaaaccacag cc                                            22

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
tctgcagctc tgtgtgaagg                                               20

<210> SEQ ID NO 8
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 8
cttcaaaaac ttctccacaa cc                                            22

<210> SEQ ID NO 9
<211> LENGTH: 17
<212> TYPE: DNA
<213> ORGANISM: Artificial Sequence
<220> FEATURE:
```

-continued

```
<223> OTHER INFORMATION: Oligonucleotide primer

<400> SEQUENCE: 9
cccacgccac gctctcc                                                  17

<210> SEQ ID NO 10
<211> LENGTH: 19
<212> TYPE: DNA
<213> ORGANISM: Artificial Sequence
<220> FEATURE:
<223> OTHER INFORMATION: Oligonucleotide primer

<400> SEQUENCE: 10
tcctgtcagt tggtgctcc                                                19
```

HUMAN UMBILICAL CORD TISSUE CELLS FOR INHIBITING ADVERSE IMMUNE RESPONSE IN HISTOCOMPATIBILITY-MISMATCHED TRANSPLANTATION

CROSS-REFERENCE TO RELATED APPLICATIONS

This application claims benefit to U.S. Provisional Patent Application No. 60/751,395, filed Dec. 16, 2005, the contents of which are incorporated by reference herein, in their entirety.

FIELD OF THE INVENTION

This invention relates to the field of transplantation immunology. In particular, the invention relates to cells derived from postpartum tissue having the capability to inhibit an adverse immune response in tissue transplantation between a histocompatibility-mismatched donor and recipient, and methods for using such postpartum tissue-derived cells to stave off rejection and prevent graft versus host disease in a transplant recipient.

BACKGROUND OF THE INVENTION

Various publications, including patents, published applications, technical articles and scholarly articles are cited throughout the specification. Each of these cited publications is incorporated by reference herein, in its entirety.

Tissue transplantation is indicated for the treatment of various diseases, pathologies, and traumatic injuries. Although thousands of transplants are performed each year, nearly 90,000 individuals in the United States alone find themselves on various transplant wait lists for tissues and organs. Contributing to the shortage of available transplant tissue is the over-arching need for compatibility between the transplant donor and the transplant recipient.

Compatibility of transplant donors and recipients stems primarily from the major histocompatibility complex (MHC), which encodes glycoproteins that are expressed on the cell surface. These glycoproteins, referred to in humans as human leukocyte antigens (HLA), play a central role in the immune system's capacity to distinguish between self and non-self. (Thorsby E et al. (2004) Transplant Proc. 36(2Suppl): 16S-21S). There are three main classifications of HLA molecules, HLA-A, HLA-B, and HLA-DR, a set of which is referred to as a haplotype. (Bradley B (1991) Immunol Lett 29:55-59; and, Schreuder G M et al. (1999) Tissue Antigens, 54:490-437). In humans, one haplotype is inherited from each parent.

Each group of HLA molecules is highly polymorphic. (Turner D (2004) Vox Sang. 87 Suppl1:87-90). As such, there is high variability of HLA expression, even among siblings. (Jeras M (2002) Transpl. Immunol. 10:205-14). This high variability of HLA expression is problematic for transplantation purposes, as any HLA mismatch between the transplant donor and recipient will facilitate rejection of the transplanted tissue. (Petersdorf E W (2004) Curr. Op. Hematol. 11:386-391).

Another problem stemming from HLA mismatching is graft versus host disease (GVHD). GVHD typically arises in instances where the grafted tissue contains immunocompetent cells that can attack the tissues of the transplant host. Bone marrow transplantation (BMT) and hematopoietic stem cell transplantation (HSCT) are particularly problematic in this regard as they typically comprise and can generate immunocompetent cells. (Iwasaki T (2004) Clin. Med. Res. 2:243-252).

BMT and HSCT are indicated for various blood diseases and immune disorders, although HSCT is increasingly the preferred method. However, one of the impediments to the survival and overall health of HSCT patients is GVHD and related complications. (Morishima Y et al. (2002) Blood. 99:4200-4206). HLA compatibility plays an important role in graft failure or survival, and whether the transplant recipient is at risk to develop GVHD. (Davies S M (2000) Blood 96:4096-41002; and, Dickinson A M et al. (2005) Curr. Opin. Immunol. 17:517-525).

To stave off GVHD and rejection of the transplanted tissues, transplant recipients must endure a lifetime of immunosuppressive treatment regimens. Many anti-rejection medications cause severe side effects in the transplant patient, and their immunosuppressive effects can leave the patient vulnerable to opportunistic infections and certain cancers. Thus, a significant advance in tissue transplantation would be to provide a means to inhibit adverse immune responses in the transplant recipient such as GVHD and rejection of the transplanted tissue with less severe side effects and complications than, and without the systemic immunosuppression of traditional methods.

SUMMARY OF THE INVENTION

One aspect of the invention features method for inhibiting an adverse immune response in a transplant recipient that is histocompatibility-mismatched to the transplant donor. The method comprises administering a cell composition to the transplant recipient in an amount effective for inhibiting the adverse immune response, wherein the cell composition comprises a pharmaceutically acceptable carrier and postpartum-derived cells derived from human postpartum tissue substantially free of blood, said cells being capable of self-renewal and expansion in culture, wherein the cells require L-Valine for growth and are capable of growth in an atmosphere containing oxygen from about 5% to at least about 20%, and wherein the cells comprise at least one of the following characteristics: (a) potential for at least about 40 doublings in culture; (b) attachment and expansion on a coated or uncoated tissue culture vessel, wherein a coated tissue culture vessel comprises a coating of gelatin, laminin, collagen, polyornithine, vitronectin, or fibronectin; (c) production of at least one of tissue factor, vimentin, and alpha-smooth muscle actin; (d) production of at least one of CD10, CD13, CD44, CD73, CD90, PDGFr-alpha, PD-L2 and HLA-A,B,C; (e) lack of production of at least one of CD31, CD34, CD45, CD80, CD86, CD117, CD141, CD178, B7-H2, HLA-G, and HLA-DR,DP,DQ, as detected by flow cytometry; (f) expression of at least one of interleukin 8; reticulon 1; chemokine (C—X—C motif) ligand 1 (melanoma growth stimulating activity, alpha); chemokine (C—X—C motif) ligand 6 (granulocyte chemotactic protein 2); chemokine (C—X—C motif) ligand 3; and tumor necrosis factor, alpha-induced protein 3; (g) expression of at least one of C-type (calcium dependent, carbohydrate-recognition domain) lectin, superfamily member 2 (activation-induced); Wilms tumor 1; aldehyde dehydrogenase 1 family, member A2; and renin; oxidized low density lipoprotein (lectin-like) receptor 1; *Homo sapiens*, clone IMAGE:4179671, mRNA, partial cds; protein kinase C, zeta; hypothetical protein DKFZp564F013; down-regulated in ovarian cancer 1; *Homo sapiens* mRNA; and cDNA DKFZp547K1113 (from clone DKFZp547K1113); (h) expression of a gene, which relative to a human cell that is a fibroblast, a mesenchymal stem cell, or an iliac crest bone marrow cell, is reduced for at least one of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin,alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus EIB 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa; (i) secretion of at least one of MCP-1, IL-6, IL-8, GCP-2, HGF, KGF, FGF, HB-EGF, BDNF, TPO, MIP1a, RANTES, and TIMP1; and (j) lack of secretion of at least one of TGF-beta2, ANG2, PDGFbb, MIP1b, I309, MDC, and VEGF, as detected by ELISA.

In some embodiments the adverse immune response is graft versus host disease, while in other embodiments the adverse immune response is rejection of the transplanted tissue. The postpartum derived cells may be placenta-derived cells, umbilicus-derived cells, or a combination of placenta-derived cells and umbilicus-derived cells. In various embodiments, the cell composition is administered by injection or infusion, or it may be administered by implantation of a device, scaffold or matrix implanted in the transplant recipient.

In some embodiments, the cell composition comprises at least about 50% postpartum-derived cells. In other embodiments, the cell composition comprises a substantially homogeneous population of postpartum-derived cells. In certain embodiments, the cells are administered with at least one other cell type. The other cell type may be administered simultaneously with, or before, or after, the postpartum-derived cells. In certain embodiments, the cells are administered with at least one other agent for treating the adverse immune response. The other agent may be administered simultaneously with, or before, or after, the postpartum-derived cells.

The other agent may include or more of an antithrombogenic agent, an anti-inflammatory agent, an immunosuppressive agent, an immunomodulatory agent, or an antiapoptotic agent.

Another aspect of the invention features a pharmaceutical composition for inhibiting an adverse immune response in a transplant recipient that is histocompatibility-mismatched to the transplant donor, comprising a pharmaceutically acceptable carrier and an amount of the above-described postpartum-derived cells effective to inhibit the adverse immune response in a transplant recipient that is histocompatibility-mismatched to the transplant donor.

In some embodiments the adverse immune response is graft versus host disease, while in other embodiments the adverse immune response is rejection of the transplanted tissue. The postpartum derived cells may be placenta-derived cells, umbilicus-derived cells, or a combination of placenta-derived cells and umbilicus-derived cells. In various embodiments, the pharmaceutical composition is formulated for administration by injection or infusion, or it may be formulated for administration by implantation of a device, scaffold or matrix implanted in the transplant recipient.

In some embodiments, the pharmaceutical composition comprises at least about 50% postpartum-derived cells. In other embodiments, it comprises a substantially homogeneous population of postpartum-derived cells. In certain embodiments, the pharmaceutical composition comprises at least one other cell type or at least one other agent for treating the adverse immune response. The other agent may include or more of an antithrombogenic agent, an anti-inflammatory agent, an immunosuppressive agent, an immunomodulatory agent, or an antiapoptotic agent.

Another aspect of the invention features a kit for inhibiting an adverse immune response in a transplant recipient that is histocompatibility-mismatched to the transplant donor, comprising a pharmaceutically acceptable carrier, a population of the postpartum-derived cells described above, and instructions for using the kit in a method for inhibiting the adverse immune response. The kit may also include one or more of at least one reagent and instructions for culturing the postpartum-derived cells, or at least one other cell type, or at least one other agent for inhibiting the adverse immune response.

Another aspect of the invention features a method for inhibiting an adverse immune response in a transplant recipient that is histocompatibility-mismatched to the transplant donor comprising administering to the patient a composition comprising one or more of a conditioned medium generated by the above-described postpartum-derived cells, a cell lysate generated from the above-described postpartum-derived cells, a soluble cell fraction generated from the above-described postpartum-derived cells, or an extracellular matrix containing the above-described postpartum-derived cells.

Yet another aspect of the invention features pharmaceutical composition for inhibiting an adverse immune response in a transplant recipient that is histocompatibility-mismatched to the transplant donor, comprising a pharmaceutically acceptable carrier and an amount of the aforementioned conditioned medium, cell lysate, soluble cell fraction or extracellular matrix effective to inhibit the adverse immune response in a transplant recipient that is histocompatibility-mismatched to the transplant donor.

Still another aspect of the invention features a kit for inhibiting an adverse immune response in a transplant recipient that is histocompatibility-mismatched to the transplant donor, comprising a pharmaceutically acceptable carrier, above-described composition comprising a conditioned medium, cell lysate, soluble cell fraction or extracellular matrix of postpartum-derived cells, and instructions for using the kit in a method for inhibiting the adverse immune response.

Other features and advantages of the invention will be understood from the drawings, detailed description and examples that follow.

DETAILED DESCRIPTION OF ILLUSTRATIVE EMBODIMENTS

Figure 1:
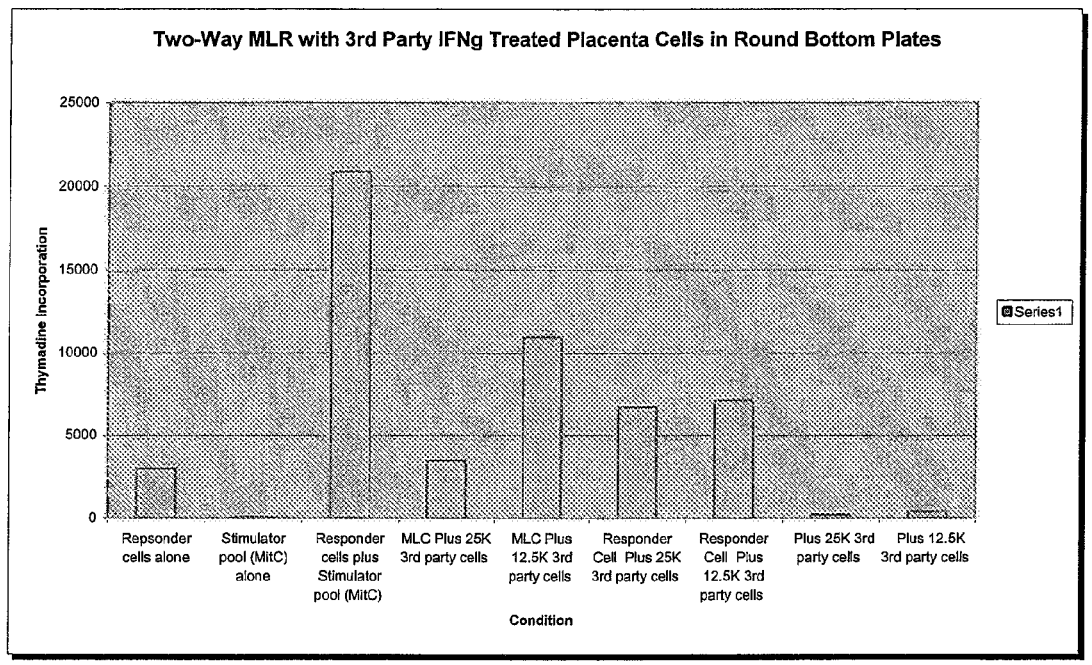
FIG. 1. Bar graph showing results of two-way mixed lymphocyte reaction (MLR) with third party IFNγ-treated placenta-derived cells in round-bottom plates.

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

The following abbreviations may be used in the specification and examples: PPDC, postpartum-derived cells; UDC, umbilicus-derived cells; PDC, placental-derived cells; MHC, major histocompatibility complex; HLA, human leukocyte antigen; BMT, bone marrow transplantation; HSCT, hematopoietic stem cell transplantation; GVHD, graft versus host disease;

Stem cells are undifferentiated cells defined by the ability of a single cell both to self-renew and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

The term inhibition refers to a reduction in adverse immunological events observed in the adaptive immune response of transplanted donor tissue against the transplant recipient, graft versus host disease, as well as the adaptive immune response of the transplant recipient against the transplanted donor tissue.

The cells of the present invention are generally referred to as postpartum cells or postpartum-derived cells (PPDCs). They also may sometimes be referred to more specifically as umbilicus-derived cells (UDCs) or placenta-derived cells (PDCs). In addition, the cells may be described as being stem or progenitor cells, the latter term being used in the broad sense. The term derived is used to indicate that the cells have been obtained from their biological source and grown or otherwise manipulated in vitro (e.g., cultured in a Growth Medium to expand the population and/or to produce a cell line). The in vitro manipulations of umbilical stem cells and the unique features of the umbilicus-derived cells of the present invention are described in detail below.

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a Growth Medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having beenpassaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Growth Medium generally refers to a medium sufficient for the culturing of PPDCs. In particular, one presently preferred medium for the culturing of the cells of the invention in comprises Dulbecco's Modified Eagle Media (also known as Dulbecco's Minimal Essential Media) (DMEM). Particularly preferred is DMEM-low glucose (also DMEM-LG herein) (Invitrogen, Carlsbad, Calif.). The DMEM-low glucose is preferably supplemented with 15% (v/v) fetal bovine serum (e.g., defined fetal bovine serum, Hyclone, Logan Utah), antibiotics and antimycotics (preferably, 50-100 Units/milliliter penicillin, 50-100 microgram/milliliter streptomycin, and 0-0.25 microgram/milliliter amphotericin B; Invitrogen, Carlsbad, Calif.), and 0.001% (v/v) 2-mercaptoethanol (Sigma, St. Louis Mo.).

The term standard growth conditions refers to culturing of cells at 37° C., in a standard humidified atmosphere comprising 5% $CO_2$. While such conditions are useful for culturing, it is to be understood that such conditions are capable of being varied by the skilled artisan who will appreciate the options available in the art for culturing cells.

Generally, a trophic factor is defined as a substance that promotes survival, growth, proliferation and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

The term effective amount refers to a concentration or amount of a compound, material, or composition, as described herein that is effective to achieve a particular biological result. Such results include, but are not limited to, inhibiting the adaptive immune response of transplanted donor tissue against the transplant recipient, as well as the adaptive immune response of the transplant recipient against the transplanted donor tissue, inhibition of graft versus host disease, and inhibition of transplant rejection. Such effective activity may be achieved, for example, by administering the cells and/or compositions of the present invention to the recipient. With respect to PPDCs as administered to a patient in vivo, an effective amount may range from as few as several hundred or fewer to as many as several million or more. In specific embodiments, an effective amount may range from $10^3$-$10^{11}$, more specifically at least about $10^4$ cells. It will be appreciated that the number of cells to be administered will vary depending on the specifics of the disorder to be treated, including but not limited to size or total volume/surface area to be treated, as well as proximity of the site of administration to the location of the region to be treated, among other factors familiar to the skilled artisan.

The terms effective period (or time) and effective conditions refer to a period of time or other controllable conditions (e.g., temperature, humidity for in vitro methods), necessary or preferred for an agent or pharmaceutical composition to achieve its intended result.

Adaptive immunity or adaptive immune response are used interchangeably and in a broad sense herein, and refer to the immune response to antigen challenge, including the development of immunological memory. The adaptive immune response includes, without limitation, humoral and cellular immunity.

Humoral immunity or humoral immune response are used interchangeably herein, and refer to the production of immunoglobulin molecules in response to an antigen challenge.

Cellular immunity or cellular immune response or cell mediated immunity are used interchangeably herein, and refer to the production, activation, and/or proliferation of cytotoxic or helper T-lymphocytes, mononuclear cells, and cytokines in response to an antigen challenge. The term encompasses all adaptive immunity that cannot be transferred to a naïve recipient with antibodies.

Innate immunity refers to the body's non-specific mechanisms for resistance to antigen challenge that are not enhanced upon subsequent challenge with a particular antigen.

The terms patient or subject are used interchangeably herein, and refer to animals, including mammals, and preferably humans, who are treated with the pharmaceutical compositions or in accordance with the methods described herein.

The terms donor or transplant donor are used interchangeably herein, and refer to an any organism that is the source of cells or tissue to be transplanted into another organism. The terms recipient or transplant recipient or transplant patient are used interchangeably herein, and refer to any organism that receives transplanted tissue from a donor.

Histocompatibility-mismatch refers to any differences in histocompatibility antigens between a transplant donor and transplant recipient that can elicit an immune response by the transplanted cells or tissue against the tissues of the transplant recipient, can elicit an immune response by the transplant recipient against the transplanted cells or tissues, and/or can result in rejection of transplanted tissue or graft versus host disease.

Rejection refers to any immune response against transplanted cells or tissue that can result in decreased growth or vitality of the transplant, or failure of the transplant to survive.

Graft versus host disease (GVHD) is used in a broad sense herein, and refers to any immune response by cells or tissue from a transplant donor against the cells or tissues of the transplant recipient, regardless of the severity or duration of the response and regardless of whether the transplant recipient manifests any clinical symptoms of GVHD recognized in the art.

The term pharmaceutically acceptable carrier (or medium), which may be used interchangeably with the term biologically compatible carrier or medium, refers to reagents, cells, compounds, materials, compositions, and/or dosage forms that are not only compatible with the cells and other agents to be administered therapeutically, but also are, within the scope of sound medical judgment, suitable for use in contact with the tissues of human beings and animals without excessive toxicity, irritation, allergic response, or other complication commensurate with a reasonable benefit/risk ratio. As described in greater detail herein, pharmaceutically acceptable carriers suitable for use in the present invention include liquids, semi-solid (e.g., gels) and solid materials (e.g., cell scaffolds and matrices, tubes sheets and other such materials as known in the art and described in greater detail herein). These semi-solid and solid materials may be designed to resist degradation within the body (non-biodegradable) or they may be designed to degrade within the body (biodegradable, bioerodable). A biodegradable material may further be bioresorbable or bioabsorbable, i.e., it may be dissolved and absorbed into bodily fluids (water-soluble implants are one example), or degraded and ultimately eliminated from the body, either by conversion into other materials or breakdown and elimination through natural pathways.

Several terms are used herein with respect to cell or tissue transplantation. The terms autologous transfer, autologous transplantation, autograft and the like refer to transplantation wherein the transplant donor is also the transplant recipient. The terms allogeneic transfer, allogeneic transplantation, allograft and the like refer to transplantation wherein the transplant donor is of the same species as the transplant recipient, but is not the same individual. A cell transplant in which the donor's cells and have been histocompatibility matched with a recipient is sometimes referred to as a syngeneic transfer. The terms xenogeneic transfer, xenogeneic transplantation, xenograft and the like refer to transplantation wherein the transplant donor is of a different species than the transplant recipient.

According to the methods described herein, a mammalian placenta and umbilical cord are recovered upon or shortly after termination of either a full-term or pre-term pregnancy, for example, after expulsion after birth. The postpartum tissue may be transported from the birth site to a laboratory in a sterile container such as a flask, beaker, culture dish, or bag. The container may have a solution or medium, including but not limited to a salt solution, such as, for example, Dulbecco's Modified Eagle's Medium (DMEM, also referred to as Dulbecco's Minimal Essential Medium) or phosphate buffered saline (PBS), or any solution used for transportation of organs used for transplantation, such as University of Wisconsin solution or perfluorochemical solution. One or more antibiotic and/or antimycotic agents, such as but not limited to penicillin, streptomycin, amphotericin B, gentamicin, and nystatin, may be added to the medium or buffer. The postpartum tissue may be rinsed with an anticoagulant solution such as heparin-containing solution. It is preferable to keep the tissue at about 4-10° C. prior to extraction of PPDCs. It is even more preferable that the tissue not be frozen prior to extraction of PPDCs.

Isolation of PPDCs preferably occurs in an aseptic environment. The umbilical cord may be separated from the placenta by means known in the art. Alternatively, the umbilical cord and placenta are used without separation. Blood and debris are preferably removed from the postpartum tissue prior to isolation of PPDCs. For example, the postpartum tissue may be washed with buffer solution, such as but not limited to phosphate buffered saline. The wash buffer also may comprise one or more antimycotic and/or antibiotic agents, such as but not limited to penicillin, streptomycin, amphotericin B, gentamicin, and nystatin.

Postpartum tissue comprising a whole placenta or a fragment or section thereof is disaggregated by mechanical force (mincing or shear forces). In a presently preferred embodiment, the isolation procedure also utilizes an enzymatic digestion process. Many enzymes are known in the art to be useful for the isolation of individual cells from complex tissue matrices to facilitate growth in culture. Ranging from weakly digestive (e.g., deoxyribonucleases and the neutral protease, dispase) to strongly digestive (e.g., papain and trypsin), such enzymes are available commercially. A non-exhaustive list of enzymes compatible herewith includes mucolytic enzyme activities, metalloproteases, neutral proteases, serine proteases (such as trypsin, chymotrypsin, or elastase), and deoxyribonucleases. Presently preferred are enzyme activities selected from metalloproteases, neutral proteases and mucolytic activities. For example, collagenases are known to be useful for isolating various cells from tissues. Deoxyribonucleases can digest single-stranded DNA and can minimize cell-clumping during isolation. Preferred methods involve enzymatic treatment with, for example, collagenase and dispase, or collagenase, dispase, and hyaluronidase, and such methods are provided wherein in certain preferred embodiments, a mixture of collagenase and the neutral protease dispase are used in the dissociating step. More preferred are those methods which employ digestion in the presence of at least one collagenase from *Clostridium histolyticum*, and either of the protease activities, dispase and thermolysin. Still more preferred are methods employing digestion with both collagenase and dispase enzyme activities. Also preferred are methods which include digestion with a hyaluronidase activity in addition to collagenase and dispase activities. The skilled artisan will appreciate that many such enzyme treatments are known in the art for isolating cells from various tissue sources. For example, the LIBERASE Blendzyme (Roche) series of enzyme combinations are suitable for use in the instant methods. Other sources of enzymes are known, and the skilled artisan may also obtain such enzymes directly from their natural sources. The skilled artisan is also well-equipped to assess new, or additional enzymes or enzyme combinations for their utility in isolating the cells of the invention. Preferred enzyme treatments are 0.5, 1, 1.5, or 2 hours long or longer. In other preferred embodiments, the tissue is incubated at 37° C. during the enzyme treatment of the dissociation step.

In some embodiments of the invention, postpartum tissue is separated into sections comprising various aspects of the tissue, such as neonatal, neonatal/maternal, and maternal aspects of the placenta, for instance. The separated sections then are dissociated by mechanical and/or enzymatic dissociation according to the methods described herein. Cells of neonatal or maternal lineage may be identified by any means known in the art, for example, by karyotype analysis or in situ hybridization for a Y chromosome.

Isolated cells or postpartum tissue from which PPDCs grow out may be used to initiate, or seed, cell cultures. Isolated cells are transferred to sterile tissue culture vessels either uncoated or coated with extracellular matrix or ligands such as laminin, collagen (native, denatured or crosslinked), gelatin, fibronectin, and other extracellular matrix proteins. PPDCs are cultured in any culture medium capable of sustaining growth of the cells such as, but not limited to, DMEM (high or low glucose), advanced DMEM, DMEM/MCDB 201, Eagle's basal medium, Ham's F10 medium (F10), Ham's F-12 medium (F12), Hayflick's Medium, Iscove's modified Dulbecco's medium, Mesenchymal Stem Cell Growth Medium (MSCGM), DMEM/F12, RPMI 1640, and CELL-GRO-FREE. The culture medium may be supplemented with one or more components including, for example, fetal bovine serum (FBS), preferably about 2-15% (v/v); equine serum (ES); human serum (HS); fetal calf serum; beta-mercaptoethanol (BME or 2-ME), preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination. The culture medium preferably comprises Growth Medium as defined for the Examples.

The cells are seeded in culture vessels at a density to allow cell growth. In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25 to about 40° C. and more preferably are cultured at 37° C. The cells are preferably cultured in an incubator. The medium in the culture vessel can be static or agitated, for example, using a bioreactor. PPDCs preferably are grown under low oxidative stress (e.g., with addition of glutathione, Vitamin C, Catalase, Vitamin E, N-Acetylcysteine). "Low oxidative stress", as used herein, refers to conditions of no or minimal free radical damage to the cultured cells.

Methods for the selection of the most appropriate culture medium, medium preparation, and cell culture techniques are well known in the art and are described in a variety of sources, including Doyle et al., (eds.), 1995, CELL & TISSUE CULTURE: LABORATORY PROCEDURES, John Wiley & Sons, Chichester; and Ho and Wang (eds.), 1991, ANIMAL CELL BIOREACTORS, Butterworth-Heinemann, Boston, which are incorporated herein by reference.

After culturing the isolated cells or tissue fragments for a sufficient period of time, PPDCs will have grown out, either as a result of migration from the postpartum tissue or cell division, or both. In some embodiments of the invention, PPDCs are passaged, or removed to a separate culture vessel containing fresh medium of the same or a different type as that used initially, where the population of cells can be mitotically expanded. The cells of the invention may be used at any point between passage 0 and senescence. The cells preferably are passaged between about 3 and about 25 times, more preferably are passaged about 4 to about 12 times, and preferably are passaged 10 or 11 times. Cloning and/or subcloning may be performed to confirm that a clonal population of cells has been isolated.

In some aspects of the invention, the different cell types present in postpartum tissue are fractionated into subpopulations from which the PPDCs can be isolated. This may be accomplished using standard techniques for cell separation including, but not limited to, enzymatic treatment to dissociate postpartum tissue into its component cells, followed by cloning and selection of specific cell types, for example but not limited to selection based on morphological and/or biochemical markers; selective growth of desired cells (positive selection), selective destruction of unwanted cells (negative selection); separation based upon differential cell agglutinability in the mixed population as, for example, with soybean agglutinin; freeze-thaw procedures; differential adherence properties of the cells in the mixed population; filtration; conventional and zonal centrifugation; centrifugal elutriation (counter-streaming centrifugation); unit gravity separation; countercurrent distribution; electrophoresis; and fluorescence activated cell sorting (FACS). For a review of clonal selection and cell separation techniques, see Freshney, 1994, CULTURE OF ANIMAL CELLS: A MANUAL OF BASIC TECHNIQUES, 3rd Ed., Wiley-Liss, Inc., New York, which is incorporated herein by reference.

The culture medium is changed as necessary, for example, by carefully aspirating the medium from the dish, for example, with a pipette, and replenishing with fresh medium. Incubation is continued until a sufficient number or density of cells accumulate in the dish. The original explanted tissue sections may be removed and the remaining cells trypsinized using standard techniques or using a cell scraper. After trypsinization, the cells are collected, removed to fresh medium and incubated as above. In some embodiments, the medium is changed at least once at approximately 24 hours post-trypsinization to remove any floating cells. The cells remaining in culture are considered to be PPDCs.

PPDCs may be cryopreserved. Accordingly, in a preferred embodiment described in greater detail below, PPDCs for autologous transfer (for either the mother or child) may be derived from appropriate postpartum tissues following the birth of a child, then cryopreserved so as to be available in the event they are later needed for transplantation.

PPDCs may be characterized, for example, by growth characteristics (e.g., population doubling capability, doubling time, passages to senescence), karyotype analysis (e.g., normal karyotype; maternal or neonatal lineage), flow cytometry (e.g., FACS analysis), immunohistochemistry and/or immunocytochemistry (e.g., for detection of epitopes), gene expression profiling (e.g., gene chip arrays; polymerase chain reaction (for example, reverse transcriptase PCR, real time PCR, and conventional PCR)), protein arrays, protein secretion (e.g., by plasma clotting assay or analysis of PDC-conditioned medium, for example, by Enzyme Linked ImmunoSorbent Assay (ELISA)), mixed lymphocyte reaction (e.g., as measure of stimulation of PBMCs), and/or other methods known in the art.

Examples of PPDCs derived from placental tissue were deposited with the American Type Culture Collection (ATCC, Manassas, Va.) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079. Examples of PPDCs derived from umbilicus tissue were deposited with the American Type Culture Collection on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

In various embodiments, the PPDCs possess one or more of the following growth features (1) they require L-valine for growth in culture; (2) they are capable of growth in atmospheres containing oxygen from about 5% to at least about 20% (3) they have the potential for at least about 40 doublings in culture before reaching senescence; and (4) they attach and expand on a coated or uncoated tissue culture vessel, wherein the coated tissue culture vessel comprises a coating of gelatin, laminin, collagen, polyornithine, vitronectin or fibronectin.

In certain embodiments the PPDCs possess a normal karyotype, which is maintained as the cells are passaged. Karyotyping is particularly useful for identifying and distinguishing neonatal from maternal cells derived from placenta. Methods for karyotyping are available and known to those of skill in the art.

In other embodiments, the PPDCs may be characterized by production of certain proteins, including (1) production of at least one of tissue factor, vimentin, and alpha-smooth muscle actin; and (2) production of at least one of CD10, CD13, CD44, CD73, CD90, PDGFr-alpha, PD-L2 and HLA-A, B, C cell surface markers, as detected by flow cytometry. In other embodiments, the PPDCs may be characterized by lack of production of at least one of CD31, CD34, CD45, CD80, CD86, CD117, CD141, CD178, B7-H2, HLA-G, and HLA-DR, DP, DQ cell surface markers, as detected by flow cytometry. Particularly preferred are cells that produce at least two of tissue factor, vimentin, and alpha-smooth muscle actin. More preferred are those cells producing all three of the proteins tissue factor, vimentin, and alpha-smooth muscle actin.

In other embodiments, the PPDCs may be characterized by gene expression, which relative to a human cell that is a fibroblast, a mesenchymal stem cell, or an iliac crest bone marrow cell, is increased for a gene encoding at least one of interleukin 8; reticulon 1; chemokine (C—X—C motif) ligand 1 (melonoma growth stimulating activity, alpha); chemokine (C—X—C motif) ligand 6 (granulocyte chemotactic protein 2); chemokine (C—X—C motif) ligand 3; tumor necrosis factor, alpha-induced protein 3; C-type lectin superfamily member 2; Wilms tumor 1; aldehyde dehydrogenase 1 family member A2; renin; oxidized low density lipoprotein receptor 1; *Homo sapiens* clone IMAGE:4179671; protein kinase C zeta; hypothetical protein DKFZp564F013; down-regulated in ovarian cancer 1; and *Homo sapiens* gene from clone DKFZp547k1113.

In yet other embodiments, the PPDCs may be characterized by gene expression, which relative to a human cell that is a fibroblast, a mesenchymal stem cell, or an iliac crest bone marrow cell, is reduced for a gene encoding at least one of: short stature homeobox 2; heat shock 27 kDa protein 2; chemokine (C—X—C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeo box 2 (growth arrest-specific homeo box); sine oculis homeobox homolog 1 (*Drosophila*); crystallin, alpha B; disheveled associated activator of morphogenesis 2; DKFZP586B2420 protein; similar to neuralin 1; tetranectin (plasminogen binding protein); src homology three (SH3) and cysteine rich domain; cholesterol 25-hydroxylase; runt-related transcription factor 3; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; neuroblastoma, suppression of tumorigenicity 1; insulin-like growth factor binding protein 2, 36 kDa; *Homo sapiens* cDNA FLJ12280 fis, clone MAMMA1001744; cytokine receptor-like factor 1; potassium intermediate/small conductance calcium-activated channel, subfamily N, member 4; integrin, beta 7; transcriptional co-activator with PDZ-binding motif (TAZ); sine oculis homeobox homolog 2 (*Drosophila*); KIAA1034 protein; vesicle-associated membrane protein 5 (myobrevin); EGF-containing fibulin-like extracellular matrix protein 1; early growth response 3; distalless homeo box 5; hypothetical protein FLJ20373; aldo-keto reductase family 1, member C3 (3-alpha hydroxysteroid dehydrogenase, type II); biglycan; transcriptional co-activator with PDZ-binding motif (TAZ); fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); BCL2/adenovirus EIB 19 kDa interacting protein 3-like; AE binding protein 1; and cytochrome c oxidase subunit VIIa polypeptide 1 (muscle).

In other embodiments, the PPDCs may be characterized by secretion of at least one of MCP-1, IL-6, IL-8, GCP-2, HGF, KGF, FGF, HB-EGF, BDNF, TPO, MIP1a, RANTES, and TIMP1. In alternative embodiments, the PPDCs may be characterized by lack of secretion of at least one of TGF-beta2, ANG2, PDGFbb, MIP1b, 1309, MDC, and VEGF, as detected by ELISA.

In preferred embodiments, the cell comprises two or more of the above-listed growth, protein/surface marker production, gene expression or substance-secretion characteristics. More preferred are those cells comprising, three, four, or five or more of the characteristics. Still more preferred are PPDCs comprising six, seven, or eight or more of the characteristics. Still more preferred presently are those cells comprising all of above characteristics.

In some preferred embodiments, the PPDCs are derived from umbilical cord tissue substantially free of blood, are capable of self-renewal and expansion in culture, have the potential to differentiate into cells of at least a neural phenotype, require L-valine for growth, can grow in at least about 5% oxygen, and comprise at least one of the following characteristics: potential for at least about 40 doublings in culture; attachment and expansion on a coated or uncoated tissue culture vessel that comprises a coating of gelatin, laminin, collagen, polyornithine, vitronectin, or fibronectin; production of vimentin and alpha-smooth muscle actin; production of CD10, CD13, CD44, CD73, and CD90; and, expression of a gene, which relative to a human cell that is a fibroblast, a mesenchymal stem cell, or an iliac crest bone marrow cell, is increased for a gene encoding interleukin 8 and reticulon 1. In some embodiments, such PPDCs do not produce CD45 and CD117. The PPDCs as described in this paragraph can be used in methods for inhibiting an adverse immune response in a transplant recipient that is histocompatibility-mismatched to the transplant donor, can be used in pharmaceutical compositions for inhibiting an adverse immune response in a transplant recipient that is histocompatibility-mismatched to the transplant donor, for example, wherein such compositions comprise the cells having these characteristics and a pharmaceutically acceptable carrier, and can be used in kits for making, using, and practicing such methods and pharmaceutical compositions as described and exemplified herein. In addition, the PPDCs as described in this paragraph can be used to generate conditioned cell culture media that can be used for making, using, and practicing such methods and pharmaceutical compositions as described and exemplified herein.

Among cells that are presently preferred for use with the invention in several of its aspects are postpartum cells having the characteristics described above and more particularly those wherein the cells have normal karyotypes and maintain normal karyotypes with passaging, and further wherein the cells express each of the markers CD10, CD13, CD44, CD73, CD90, PDGFr-alpha, and HLA-A, B, C, wherein the cells produce the immunologically-detectable proteins which correspond to the listed markers. Still more preferred are those cells which in addition to the foregoing do not produce proteins corresponding to any of the markers CD31, CD34, CD45, CD117, CD141, or HLA-DR, DP, DQ, as detected by flow cytometry.

In another of its several aspects, the invention provides populations of cells comprising the cells described above. Cell populations are useful in connection with the methods of the invention, as well as in connection with making the pharmaceutical cell compositions and cell lysates in larger amounts than isolated cells can provide.

Preferred populations comprise from about 1% postpartum-derived cells to about 10% postpartum cells. More preferred populations comprise at least about 10% postpartum-derived cells. More preferred populations comprise at least about 25% postpartum-derived cells. Also, some preferred populations comprise about 50% postpartum-derived cells. Such populations may be useful for coculture or other cultures wherein the cells are equally populous and divide at the same rate, or where the population is adjusted to about 50% of each culture after expansion of the cultures in coculture or separately. More preferred for some applications are populations comprising at least about 65% postpartum-derived cells. Populations that comprising at least 90% postpartum-derived cells are highly preferred for certain aspects of the invention. More preferred populations comprise substantially only postpartum-derived cells.

The populations may comprise a clonal cell line of postpartum-derived cells. Such populations are particularly useful wherein a cell clone with highly desirable functionality is isolated. Both neotal and maternal clones are useful and are provided herein. Methods of isolating clonal cell lines from cultured cells are known in the art.

In various embodiments, the methods of the invention may utilize cell lysates, soluble cell fractions and membrane-enriched cell fractions prepared from the populations of the postpartum cells. Such lysates and fractions have many utilities. Use of cell lysates, and more particularly soluble cell fractions, in vivo allows the beneficial intracellular milieu to be used in a transplant recipient that is histocompatibility-mismatched to the transplant donor without stimulating lymphocytes or generating other adverse immunological responses, without facilitating rejection of the transplanted tissue, and without triggering rejection.

Methods of lysing cells are well-known in the art and include various means of mechanical disruption, enzymatic disruption, or chemical disruption, or combinations thereof. Such cell lysates may be prepared from cells directly in their Growth Medium and thus containing secreted growth factors and the like, or may be prepared from cells washed free of medium in, for example, PBS or another solution. For making lysates from cells directly in the growth medium it is preferred that cells are grown in serum from the species in which the lysates are to be used, in some embodiments, washed cells may be preferred. Washed cells may be resuspended at concentrations greater than the original population density if preferred.

Cell lysates prepared from populations of postpartum-derived cells may be used as is, further concentrated, by for example, ultrafiltration or lyophilization, or even dried, enriched, partially purified, combined with pharmaceutically-acceptable carriers or diluents as are known in the art, or combined with other compounds such as biologicals, for example pharmaceutically useful protein compositions. Cell lysates may be used in vitro or in vivo, alone or, for example, with syngeneic or autologous live cells. The lysates, if introduced in vivo, may be introduced locally at a site of treatment, or remotely to provide, for example, needed cellular growth factors to a patient. Preferably, the lysates are not immunogenic, and more preferably they are immunologically tolerated in a broad population of syngeneic and allogeneic recipients without adverse immunological consequences or reaction. Cell lysates of the invention are useful from cells at any stage or age which have been grown under conditions for growth and expansion, for example on Growth Medium. Even senescent cells are useful for the preparation of lysate and can provide certain factors that are biologically useful. Nonviable or even dead or killed cells have utility for preparing lysates, and cellular fractions.

The methods of the invention can also utilize pharmaceutical compositions comprising a postpartum-derived cell and another therapeutic agent, factor, or bioactive agent, such as a pharmaceutical compound. Such bioactive agents include, but are not limited to, IGF, LIF, PDGF, EGF, FGF, as well as antithrombogenic, anti-apoptotic agents, anti-inflammatory agents, immunosuppressive or immunomodulatory agents, and antioxidants. Such compositions can further comprise one or more additional cell types in addition to the PPDCs and the bioactive component.

Thus, in conjunction with postpartum-derived cells, other biologically active molecules, such as antithrombogenic agents, anti-apoptotic agents, and anti-inflammatory agents may be useful and may be administered in sequence with, or coadministered with the cells, individually or in combinations or two or more such compounds or agents. For example, anti-apoptotic agents may be useful to minimize programmed cell death. Such agents include but are not limited to EPO, EPO derivatives and analogs, and their salts, TPO, IGF-1, IGF-II, hepatocyte growth factor (HGF), and caspase inhibitors. Anti-inflammatory agents include but are not limited to P38 MAP kinase inhibitors, statins, IL-6 and IL-1 inhibitors, Pemirolast, Tranilast, Remicade®, Sirolimus, nonsteroidal anti-inflammatory compounds, for example, Tepoxalin, Tolmetin, and Suprofen.

Other bioactive factors or therapeutic agents which can be coadministered with the postpartum-derived cells include, for example, antithrombogenic factors, immunosuppressive or immunomodulatory agents, and antioxidants. One purpose for co-administration or combination therapy of postpartum-derived cells with immunosuppressives is to supplement immunosuppressant effectiveness. In one embodiment, combination therapy of postpartum-derived cells with immunosuppressives may achieve the same level of biological efficacy while allowing for a reduction in the dosage of the immunosuppressive administered and thereby alleviate undesirable side effects as encountered with use of the immunosuppressive alone. In another embodiment, the combination therapy of postpartum-derived cells with immunosuppressives may allow for an increase in overall biological efficacy without an increase in the dosage of the immunosuppressive administered as opposed to therapy with the immunosuppressive alone. Examples of immunosuppressive and immunomodulatory agents include calcineurin inhibitors, for example cyclosporine, Tacrolimus, mTOR inhibitors such as Sirolimus or Everolimus; anti-proliferatives such as azathioprine and mycophenolate mofetil; corticosteroids for example prednisolone or hydrocortisone; antibodies such as monoclonal anti-IL-2Rα receptor antibodies, Basiliximab, Daclizumab; polyclonal anti-T-cell antibodies such as anti-thymocyte globulin (ATG), anti-lymphocyte globulin (ALG), and the monoclonal anti-T cell antibody OKT3. Antithrombogenic compounds which can be therapeutically provided in conjunction with the cells of the invention include, for example, heparin, heparin derivatives, urokinase, and PPack (dextrophenylalanine proline arginine chloromethylketone); antithrombin compounds, platelet receptor antagonists, anti-thrombin antibodies, anti-platelet receptor antibodies, aspirin, dipyridamole, protamine, hirudin, prostaglandin inhibitors, and platelet inhibitors. Antioxidants are well known in the art of course and any pharmaceutically acceptable antioxidant may be administered in conjunction with the cells of the invention including probucol; vitamins A, C, and E, coenzyme Q-10, glutathione, L cysteine, N-acetylcysteine, or antioxidant derivative, analogs or salts of the foregoing.

In addition to the above, compositions derived from the cells may be used in accordance with the methods of the invention. Cell lysates, soluble cell fractions and membrane-enriched cell fractions are provided herein, as described above in detail. Extracellular matrices derived from the cells, for example, comprising basement membranes are also useful and are provided herein. Cell lysates, soluble cell fractions, membrane-enriched cell fractions and extracellular matrix derived from the cells can all be administered to patients as appropriate, or coadministered with the cells of the invention, with or without additional cells or cell types.

Methods of the invention may also include the use of conditioned culture media as provided herein. Such media have first been used to grow the cells or cultures of the invention, which during growth secrete one or more useful products into the medium. Conditioned medium from these novel cells are useful for many purposes, including for example, supporting the growth of other mammalian cells in need of growth factors or trophic factors secreted into the media by the cells and cultures of the invention, and promoting, for example, angiogenesis. Methods of preparing and storing conditioned media are known in the art and primarily involve removal of the cells, for example by centrifugation.

The invention provides in another of its aspects cell compositions for use in transplantation, comprising a pharmaceutically-acceptable carrier and postpartum-derived cells derived from mammalian postpartum tissue substantially free of blood. The cells are capable of self-renewal and expansion in culture and have the potential to inhibit any immune response by the grafted cells or tissue against the recipient and/or to inhibit any immune response by the recipient against the transplanted tissue in order to inhibit rejection.

The postpartum-derived cells are capable of growth in an atmosphere containing oxygen from about 5% to at least about 20%. The cells also require L-valine for growth, have the potential for at least about 40 doublings in culture, attach and expand on a coated or uncoated tissue culture vessel, wherein a coated tissue culture vessel is coated with gelatin, laminin, or fibronectin; produce tissue factor, vimentin, and alpha-smooth muscle actin; produce each of CD10, CD13, CD44, CD73, CD90, PDGFr-alpha, and HLA-A,B,C; and do not produce any of CD31, CD34, CD45, CD117, CD141, or HLA-DR, DP, DQ, as detected by flow cytometry. In preferred embodiments, the cells are derived from human tissue.

The cell compositions can be administered therapeutically to a transplant recipient. The cell compositions can comprise cells or cell products that inhibit an adverse immune response in the transplant recipient that is histocompatibility-mismatched to the transplant donor such as graft versus host disease and/or rejection of the transplanted cells or tissue.

The cell compositions can be administered to the transplant recipient, for example, by injection. In certain embodiments, the cell compositions are injected at or near the situs of the transplant. In other embodiments, the injection may be onto the surface of the transplanted tissue, into an adjacent area, or even to a more remote area. In preferred embodiments, the cells can home to the area of the transplant. Particularly preferred are cells that can be injected intravenously and locate appropriately to the desired site of action.

The cell compositions can also be provided in the form of a matrix-cell complex. Matrices include biocompatible scaffolds, lattices, self-assembling structures and the like, whether bioabsorbable or not, liquid, gel, or solid. Such matrices are known in the arts of therapeutic cell treatment, surgical repair, tissue engineering, and wound healing. Preferably the matrices are pretreated with the cells. More preferably the matrices are populated with cells in close association to the matrix or its spaces. The cells can adhere to the matrix in some embodiments; in others, the cells are entrapped or contained within the matrix spaces. Most preferred are those matrix-cell complexes were the cells are growing in close association with the matrix and when used therapeutically, the growth and survival of the transplanted tissue is stimulated and supported, and proper angiogenesis is similarly stimulated or supported, and any immune response by the transplant recipient against the transplanted tissue or by the grafted tissue against the recipient is inhibited. The matrix-cell compositions can be introduced into a patient's body in any way known in the art, including but not limited to implantation, injection, surgical attachment, transplantation with other tissue, injection, and the like. In some embodiments, the matrices form in vivo, or even more preferably in situ, for example in situ polymerizable gels can be used in accordance with the invention. Examples of such gels are known in the art.

In some embodiments, the postpartum-derived cells, or co-cultures thereof, may be seeded onto such three-dimensional matrices, such as scaffolds and implanted in vivo, where the seeded cells may proliferate on or in the framework or help establish transplanted tissue and inhibit a graft versus host response in vivo with or without cooperation of other cells.

Growth of PPDCs or co-cultures thereof on the three-dimensional framework preferably results in the formation of a three-dimensional tissue, or foundation for such tissue, which can be utilized in vivo, for example, to inhibit any immune response by the grafted cells or tissue against the recipient, and/or to inhibit rejection of the grafted cells or tissue. In one embodiment, the three-dimensional scaffolds can be prepared as tubular structures, for example, for use in transplants of blood vessels or ducts.

In accordance with one aspect of the invention, PPDCs or co-cultures thereof are inoculated, or seeded on a three-dimensional framework or matrix, such as a scaffold, a foam or hydrogel. The framework may be configured into various shapes such as generally flat, generally cylindrical or tubular, or can be completely free-form as may be required or desired for the corrective structure under consideration. In some embodiments, the PPDCs grow on the three dimensional structure, while in other embodiments, the cells only survive, or even die, however in doing so they inhibit any immune response by the grafted cells or tissue against the recipient, and/or to inhibit rejection of the grafted cells or tissue. In some embodiments, the PPDCs facilitate the vascularization, growth, and vitality of the transplanted cells or tissue.

The matrix can be designed such that the matrix structure supports the PPDCs or co-cultures thereof without subsequent degradation or allows the transplant to vascularize and support itself, at which point, the matrix is degraded. A review of matrix design is provided by Hutmacher, *J. Biomat. Sci. Polymer Edn.*, 12(1):107-124 (2001).

The matrices, scaffolds, foams and self-assembling systems contemplated for use herein can be implanted in combination with any one or more cells, growth factors, drugs, or other components, such as bioactive agents that promote healing, or in growth of tissue, or stimulate vascularization or innervation thereof or otherwise enhance or improve the therapeutic outcome or the practice of the invention, in addition to the cells of the invention.

The cells of the invention can be grown freely in culture or removed from the culture and inoculated onto a three-dimensional framework. Inoculation of the three-dimensional framework with a concentration of cells, e.g., approximately $10^6$ to $5 \times 10^7$ cells per milliliter, preferably results in the establishment of the three-dimensional support in relatively shorter periods of time. Moreover in some application it may be preferably to use a greater or lesser number of cells depending on the result desired.

In some embodiments, it is useful to re-create in culture the cellular microenvironment found in vivo, such that the extent to which the cells are grown prior to implantation in vivo or use in vitro may vary. PPDCs or co-cultures thereof may be inoculated onto the framework before or after implantation. For inoculation of the cells onto the framework before implantation, the framework is preferably incubated in an appropriate growth medium. During the incubation period, the inoculated cells will grow and envelop the framework and may, for example, bridge or partially bridge any interstitial spaces therein.

Examples of matrices, for example scaffolds which may be used for aspects of the invention include mats (woven, knitted, and more preferably nonwoven) porous or semiporous foams, self assembling peptides and the like. Nonwoven mats may, for example, be formed using fibers comprised of natural or synthetic polymers. In a preferred embodiment, absorbable copolymers of glycolic and lactic acids (PGA/PLA), sold under the tradename VICRYL (Ethicon, Inc., Somerville, N.J.) are used to form a mat. Foams, composed of, for example, poly(epsilon-caprolactone)/poly(glycolic acid) (PCL/PGA) copolymer, formed by processes such as freeze-drying, or lyophilization, as discussed in U.S. Pat. No. 6,355,699, can also serve as scaffolds. Gels also form suitable matrices, as used herein. Examples include in situ polymerizable gels, and hydrogels, for example composed of self-assembling peptides. These materials are frequently used as supports for growth of tissue. In situ-forming degradable networks are also suitable for use in the invention (see, e.g., Anseth, K. S. et al, 2002, *J. Controlled Release* 78: 199-209; Wang, D. et al., 2003, *Biomaterials* 24: 3969-3980; U.S. Patent Publication 2002/0022676 to He et al.). These materials are formulated as fluids suitable for injection, then may be induced by a variety of means (e.g., change in temperature, pH, exposure to light) to form degradable hydrogel networks in situ or in vivo.

According to one embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another embodiment, the cells of the invention are seeded onto foam scaffolds that may be composite structures. In addition, the three-dimensional framework may be molded into a useful shape, such as a specific structure in the body to be repaired, replaced, or augmented through transplantation.

The framework may be treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework may be modified to improve the attachment or growth of cells and differentiation of tissue, such as by plasma-coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

Different proportions of the various types of collagen, for example, deposited on the framework can affect the growth of tissue-specific or other cells which may be later inoculated onto the framework or which may grow onto the structure in vivo. For example, for three-dimensional skin culture systems, collagen types I and III are preferably deposited in the initial matrix. Alternatively, the framework can be inoculated with a mixture of cells which synthesize the appropriate collagen types desired. Thus, depending upon the tissue to be cultured, the appropriate collagen type to be inoculated on the framework or produced by the cells seeded thereon may be selected. For example, the relative amounts of collagenic and elastic fibers present in the framework can be modulated by controlling the ratio of collagen-producing cells to elastin-producing cells in the initial inoculum. For example, since the inner walls of arteries are rich in elastin, an arterial scaffold should contain a co-culture of smooth muscle cells which secrete elastin.

The seeded or inoculated three-dimensional framework of the invention can be used in a variety of applications. These include but are not limited to transplantation or implantation of either the cultured cells obtained from the matrix or the cultured matrix itself in vivo.

PPDCs can be inoculated onto a flat scaffold. The scaffold is preferably incubated in culture medium prior to implantation. Two or more flat frameworks can be laid atop another and sutured together to generate a multilayer framework.

A scaffold can be cut into a strip (e.g., rectangular in shape) of which the width is approximately equal to the inner circumference of a tubular organ, for example, a duct such as the hepatic duct, into which it will ultimately be inserted. The cells can be inoculated onto the scaffold and incubated by floating or suspending in liquid media. At the appropriate stage of confluence, the scaffold can be rolled up into a tube by joining the long edges together. The seam can be closed by suturing the two edges together using fibers of a suitable material of an appropriate diameter.

According to the invention, a scaffold can be formed as a tube, inoculated with PPDCs, and suspended in media in an incubation chamber. In order to prevent cells from occluding the lumen, one of the open ends of the tubular framework can be affixed to a nozzle. Liquid media can be forced through this nozzle from a source chamber connected to the incubation chamber to create a current through the interior of the tubular framework. The other open end can be affixed to an outflow aperture which leads into a collection chamber from which the media can be recirculated through the source chamber. The tube can be detached from the nozzle and outflow aperture when incubation is complete. This method is described by Ballermann, B. J., et al., Int. Application No. WO 94/25584 and in U.S. application Ser. No. 08/430,768, both of which are incorporated herein by reference in their entirety.

In general, two three-dimensional frameworks can be combined into a tube in accordance with the invention using any of the following methods.

Two or more flat frameworks can be laid atop another and sutured together. This two-layer sheet can then be rolled up, and, as described above, joined together and secured.

One tubular scaffold that is to serve as the inner layer can be inoculated with PPDCs and incubated. A second scaffold can be grown as a flat strip with width slightly larger than the outer circumference of the tubular framework. After appropriate growth is attained, the flat framework can be wrapped around the outside of the tubular scaffold followed by closure of the seam of the two edges of the flat framework and, preferably, securing the flat framework to the inner tube.

Two or more tubular meshes of slightly differing diameters can be grown separately. The framework with the smaller diameter can be inserted inside the larger one and secured.

For each of these methods, more layers can be added by reapplying the method to the double-layered tube. The scaffolds can be combined at any stage of growth of the PPDCs, and incubation of the combined scaffolds can be continued when desirable.

The lumenal aspect of the tubular construct can be comprised of or treated with materials that render the lumenal surface of the tubular scaffold non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the lumenal surface of the tubular scaffold non-thrombogenic. Such treatments include anti-thrombotic agents such as heparin, and treatments which alter the surface charge of the material such as plasma coating.

The therapeutic cell compositions, in certain embodiments also comprise cells that express at least one of interleukin 8, reticulon 1, chemokine (C—X—C motif) ligand 1 (melanoma growth stimulating activity, alpha), chemokine (C—X—C motif) ligand 6 (granulocyte chemotactic protein 2), chemokine (C—X—C motif) ligand 3, and tumor necrosis factor, alpha-induced protein 3, or which have reduced expression, relative to a human cell that is a fibroblast, a mesenchymal stem cell, or an iliac crest bone marrow cell, for at least one of short stature homeobox 2, heat shock 27 kDa protein 2, chemokine (C—X—C motif) ligand 12 (stromal cell-derived factor 1), elastin (supravalvular aortic stenosis, Williams-Beuren syndrome), *Homo sapiens* mRNA, cDNA DKFZp586M2022 (from clone DKFZp586M2022), mesenchyme homeobox 2 (growth arrest-specific homeobox), sine oculis homeobox homolog 1 (*Drosophila*), crystallin, alpha B, dishevelled associated activator of morphogenesis 2, DKFZP586B2420 protein, similar to neuralin 1, tetranectin (plasminogen binding protein), src homology three (SH3) and cysteine rich domain, B-cell translocation gene 1, antiproliferative, cholesterol 25-hydroxylase, runt-related transcription factor 3, hypothetical protein FLJ23191, interleukin 11 receptor alpha, procollagen C-endopeptidase enhancer, frizzled homolog 7 (*Drosophila*), hypothetical gene BC008967, collagen, type VIII alpha 1, tenascin C (hexabrachion), iroquois homeobox protein 5, hephaestin, integrin, beta 8, synaptic vesicle glycoprotein 2, *Homo sapiens* cDNA FLJ12280 fis, clone MAMMA1001744, cytokine receptor-like factor 1, potassium intermediate/small conductance calcium-activated channel, subfamily N, member 4, integrin, alpha 7, DKFZP586L151 protein, transcriptional co-activator with PDZ-binding motif (TAZ), sine oculis homeobox homolog 2 (*Drosophila*), KIAA1034 protein, early growth response 3, distal-less homeobox 5, hypothetical protein FLJ20373, aldo-keto reductase family 1, member C3 (3-alpha hydroxysteroid dehydrogenase, type II), biglycan;

fibronectin 1, proenkephalin, integrin, beta-like 1 (with EGF-like repeat domains), *Homo sapiens* mRNA full length insert cDNA clone EUROIMAGE 1968422, EphA3; KIAA0367 protein, natriuretic peptide receptor C/guanylate cyclase C (atrionatriuretic peptide receptor C), hypothetical protein FLJ14054, *Homo sapiens* mRNA, cDNA DKFZp564B222 (from clone DKFZp564B222), vesicle-associated membrane protein 5 (myobrevin), EGF-containing fibulin-like extracellular matrix protein 1, BCL2/adenovirus EIB 19 kDa interacting protein 3-like, AE binding protein 1, cytochrome c oxidase subunit VIIa polypeptide 1 (muscle), neuroblastoma, suppression of tumorigenicity 1, insulin-like growth factor binding protein 2, 36 kDa.

Preferred cell compositions also comprise cells which secrete at least one of MCP-1, IL-6, IL-8, GCP-2, HGF, KGF, FGF, HB-EGF, BDNF, TPO, MIP1a, RANTES, and TIMP1, and do not secrete at least one of TGF-beta2, ANG2, PDG-Fbb, MIP1b, 1309, MDC, and VEGF, as detected by ELISA.

In yet another of its aspects, the invention provides methods for inhibiting an adverse immune response in a transplant recipient that is histocompatibility-mismatched to the transplant donor, comprising administering a postpartum-derived cell composition to the transplant recipient in an amount effective for inhibiting the adverse immune response.

In some embodiments, the adverse immune response is an adaptive immune response. In a detailed embodiment, the adverse immune response is an immune response by the grafted tissue against the transplant patient and may result in graft versus host disease. In another detailed embodiment, the adverse immune response is rejection of the transplanted tissue. In some embodiments, the methods are effective to inhibit both graft versus host disease and rejection of the transplanted tissue. In all such embodiments, it is preferable that the postpartum derived cells that comprise the composition are umbilicus-derived cells, placenta-derived cells, or a combination of umbilicus- and placenta-derived cells.

The postpartum derived cell compositions can provide support for growth, stimulation, or vitality of the transplanted tissue. The postpartum derived cells can be coadministered with cell parts, cell lysates, or with other allogeneic, syngeneic or autologous cells, although successful inhibition of an adverse immune response could comprise administering PPDCs to the transplant patient in the absence of other cells, cell parts, or cell lysates. The cells need not integrate into the transplanted tissue, although it is preferred that the PPDCs at least partially integrate, multiply, or survive in the patient. In other preferred embodiments, the patient experiences additional benefits from the administration of the PPDCs, for example, the ability of the PPDCs to support the growth of other cells, including stem cells or progenitor cells present in or around the transplanted tissue, growth or vascularization of the transplanted tissue, and the production of beneficial cellular factors, chemokines, cytokines and the like. In some embodiments, the transplant recipient benefits from the therapeutic treatment with the PPDCs, but the PPDCs do not survive for a prolonged period in the patient. In one embodiment, the cells gradually decline in number, viability or biochemical activity, in other embodiments, the decline in cells may be preceded by a period of activity, for example growth, division, or biochemical activity. In other embodiments, senescent, nonviable or even dead cells are able to have a beneficial effect.

The methods may further comprise administering one or more agents in addition to the cell composition. Such agents can be administered before, after, or at the same time the cell composition is administered. Non-limiting examples of suitable agents include antithrombogenic agents, anti-inflammatory agents, immunosuppressive agents, immunomodulatory agents, and antiapoptotic agents or other agents suitable in the art. The choice of appropriate agent is within the skill of the art, and may vary depending on the physical characteristics or overall health or wellness of the transplant recipient.

The administering of PPDCs is preferably carried out in vivo by transplanting, implanting, injecting, fusing, delivering via catheter, delivering via device implanted in the transplant recipient, or providing as a matrix-cell complex, or any other means known in the art for providing cell therapy.

In some embodiments of the inventive methods, the cell composition comprises about 50% postpartum-derived cells. In preferred embodiments, the cell composition comprises substantially only postpartum-derived cells. In more preferred embodiments, the therapeutic cell composition comprises a substantially homogeneous population of postpartum-derived cells.

Also featured in accordance with the present invention are methods for inhibiting an adverse immune response in a transplant recipient that is histocompatibility-mismatched to the transplant donor, wherein the method comprises administering to the patient a composition comprising a conditioned medium generated by postpartum-derived cells, a cell lysate generated from postpartum-derived cells, a soluble cell fraction generated from postpartum-derived cells, or an extracellular matrix of postpartum-derived cells. The adverse immune response can be graft versus host disease or rejection of the transplanted tissue. In these embodiments the postpartum derived cells that are used to make the compositions can be umbilicus-derived cells, placenta-derived cells or a combination of both. In addition to the composition, additional cell types or additional agents such as antithrombogenic agents, anti-inflammatory agents, immunosuppressive agents, immunomodulatory agents, antiapoptotic agents can be administered to the transplant recipient.

Also provided herein are methods for inhibiting an adverse immune response in a transplant recipient that is histocompatibility-mismatched to the transplant donor, comprising administering a postpartum-derived cell composition to the patient in an amount effective for inhibiting the adverse immune response, wherein the postpartum-derived cell composition is administered as a matrix-cell complex. In certain embodiments, the matrix is a scaffold, preferably bioabsorbable, comprising at least the postpartum-derived cells.

Kits for practicing the methods of the invention are also provided. Where used to inhibit an adverse immune response in a transplant recipient that is histocompatibility-mismatched to the transplant donor, the kits include a PPDC composition, with or without a matrix, and with or without a co-culture present. The kits also optionally include a means of administering the cells, for example by injection, and a pharmaceutically-acceptable carrier for the cells, if required. The kits include instructions for use of the cells.

The invention also provides for banking of tissues, cells, populations and cell compositions of the invention. As discussed above, the PPDCs are readily cryopreserved. The invention therefore provides methods of cryopreserving the cells in a bank, wherein the cells are stored frozen and associated with a complete characterization of the cells based on immunological, biochemical and genetic properties of the cells. The cells so frozen can be used therapeutically for autologous, syngeneic, or allogeneic transplants, depending on the requirements of the procedure and the needs of the patient. Preferably, the information on each cryopreserved sample is stored in a computer which is searchable based on the requirements of the surgeon, procedure and patient with suitable matches being made based on the characterization of the cells or populations. Preferably, the cells of the invention are grown and expanded to the desired quantity of cells and cell compositions are prepared either separately or as co-cultures, in the presence or absence of a matrix or support. While for some applications it may be preferable to use cells freshly prepared, the remainder can be cryopreserved and banked by freezing the cells and entering the information in the computer to associate the computer entry with the samples. Even where it is not necessary to match a transplant source or donor with a recipient of such cells for immunological purposes, the bank system makes it easy to match, for example, desirable biochemical or genetic properties of the banked cells to the therapeutic needs. Upon matching of the desired properties with a particle banked sample, the sample is retrieved and readied for therapeutic use. Cell lysates prepared as described herein may also be cryopreserved and banked in accordance with the present invention.

In another aspect of the invention, kits for isolation, growth and maintenance, and use of PPDCs are provided. The cells, cell lysates, soluble cell fractions, membrane fractions and matrices can conveniently be employed as parts of kits, for example, for a kit for culture or implantation. The invention provides a kit including the postpartum-derived cells and additional components, including instructions for isolation, growth or maintenance, or use of the cells or cell fractions, together with for example, matrix (e.g., a scaffold) material, hydrating agents (e.g., physiologically-compatible saline solutions, prepared cell culture media), cell culture substrates (e.g., culture dishes, plates, vials, etc.), cell culture media (whether in liquid or dehydrated form), antibiotic compounds, hormones, and the like. Kits for growth can for example include all of the components of the Growth Medium as used herein, including serum, for example fetal bovine serum. While the kit can include any such components, preferably it includes all ingredients necessary for its intended use. If desired, the kit also can include cells (typically cryopreserved), which can be seeded into the lattice as described herein. Kits for isolation will contain everything required to practice the isolation methods as provided herein, except for the umbilicus tissue which should be obtained fresh or frozen from a tissue bank at the time of isolation. The surgical equipment for dissociating the tissue, preferred enzymes, or choices of enzymes in stable form are provided, as are the buffers and medium, cell strainers and the like, as required or preferred for the method as disclosed above. Detailed instructions with optional steps and lists of suppliers of optional or alternative materials are also conveniently provided. Control cells can be included for comparison of the cells isolated to, for example the UDC cultures deposited with the ATCC.

Kits for utilizing the PPDCs preferably contain populations of the cells, or compositions comprising the cells, components and products, or fractions or conditioned media derived from the cells as described above. In some embodiments, the kits may include one or more cell populations, including at least PDCs and/or UDCs and a pharmaceutically acceptable carrier (liquid, semi-solid or solid). The populations in some embodiments are homogenous or even clonal cell lines of UDCs or PDCs. In other embodiments, the kits include other cell lines for use in coculture. Kits preferably include additional bioactive agents as desired for example anti-thrombogenic agents, anti-inflammatory agents, anti-apoptotic agents, and immunosuppressive or immunomodulatory compounds. The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) UDCs or fractions, components or products of UDCs, (2) reagents for practicing the in vitro method, (3) other cells or cell populations, as appropriate, for example for cocultures and (4) instructions for conducting the in vitro method. Kits for the preparation of cell-derived components can include both the components required for growth of the cells and the components required for preparing the cell fraction of interest, along with instructions for obtaining the desired fraction from the cells. Kits for production of and collection of conditioned media are also provided herein and include cells, medium, collection vessels, instructions, standards for assaying the secreted molecules of interest and the like.

The following examples describe several aspects of embodiments of the invention in greater detail. These examples are provided to further illustrate, not to limit, aspects of the invention described herein.

EXAMPLE 1

Derivation of Cells from Postpartum Tissue

This example describes the preparation of postpartum-derived cells from placental and umbilical cord tissues. Postpartum umbilical cords and placentae were obtained upon birth of either a full term or pre-term pregnancy. Cells were harvested from 5 separate donors of umbilicus and placental tissue. Different methods of cell isolation were tested for their ability to yield cells with: 1) the potential to differentiate into cells with different phenotypes, a characteristic common to stem cells, or 2) the potential to provide trophic factors useful for other cells and tissues.

Methods & Materials

Umbilical cell isolation. Umbilical cords were obtained from National Disease Research Interchange (NDRI, Philadelphia, Pa.). The tissues were obtained following normal deliveries. The cell isolation protocol was performed aseptically in a laminar flow hood. To remove blood and debris, the cord washed in phosphate buffered saline (PBS; Invitrogen, Carlsbad, Calif.) in the presence of antimycotic and antibiotic (100 units/milliliter penicillin, 100 micrograms/milliliter streptomycin, 0.25 micrograms/milliliter amphotericin B). The tissues were then mechanically dissociated in 150 cm$^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing antimycotic and antibiotic as described above. In some experiments, an enzyme mixture of collagenase and dispase was used ("C:D;" collagenase (Sigma, St Louis, Mo.), 500 Units/milliliter; and dispase (Invitrogen), 50 Units/milliliter in DMEM:-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM:-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of Growth Medium (DMEM: Low glucose (Invitrogen), 15 percent (v/v) fetal bovine serum (FBS; defined bovine serum; Lot#AND18475; Hyclone, Logan, Utah), 0.001% (v/v) 2-mercaptoethanol (Sigma), 1 milliliter per 100 milliliters of antibiotic/antimycotic as described above. The cell suspension was filtered through a 70-micrometer nylon cell strainer (BD Biosciences). An additional 5 milliliters rinse comprising Growth Medium was passed through the strainer. The cell suspension was then passed through a 40-micrometer nylon cell strainer (BD Biosciences) and chased with a rinse of an additional 5 milliliters of Growth Medium.

The filtrate was resuspended in Growth Medium (total volume 50 milliliters) and centrifuged at 150×g for 5 minutes. The supernatant was aspirated and the cells were resuspended in 50 milliliters of fresh Growth Medium. This process was repeated twice more.

Upon the final centrifugation supernatant was aspirated and the cell pellet was resuspended in 5 milliliters of fresh Growth Medium. The number of viable cells was determined using Trypan Blue staining. Cells were then cultured under standard conditions.

The cells isolated from umbilical cords were seeded at 5,000 cells/cm$^2$ onto gelatin-coated T-75 cm$^2$ flasks (Corning Inc., Corning, N.Y.) in Growth Medium with antibiotics/antimycotics as described above. After 2 days (in various experiments, cells were incubated from 2-4 days), spent medium was aspirated from the flasks. Cells were washed with PBS three times to remove debris and blood-derived cells. Cells were then replenished with Growth Medium and allowed to grow to confluence (about 10 days from passage 0) to passage 1. On subsequent passages (from passage 1 to 2 and so on), cells reached sub-confluence (75-85 percent confluence) in 4-5 days. For these subsequent passages, cells were seeded at 5000 cells/cm$^2$. Cells were grown in a humidified incubator with 5 percent carbon dioxide and atmospheric oxygen, at 37° C.

Placental Cell Isolation. Placental tissue was obtained from NDRI (Philadelphia, Pa.). The tissues were from a pregnancy and were obtained at the time of a normal surgical delivery. Placental cells were isolated as described for umbilical cell isolation.

The following example applies to the isolation of separate populations of maternal-derived and neonatal-derived cells from placental tissue.

The cell isolation protocol was performed aseptically in a laminar flow hood. The placental tissue washed in phosphate buffered saline (PBS; Invitrogen, Carlsbad, Calif.) in the presence of antimycotic and antibiotic (as described above) to remove blood and debris. The placental tissue was then dissected into three sections: top-line (neonatal side or aspect), mid-line (mixed cell isolation neonatal and maternal) and bottom line (maternal side or aspect).

The separated sections were individually washed several times in PBS with antibiotic/antimycotic to further remove blood and debris. Each section was then mechanically dissociated in 150 cm$^2$ tissue culture plates in the presence of 50 milliliters of DMEM/Low glucose, to a fine pulp. The pulp was transferred to 50 milliliter conical tubes. Each tube contained approximately 5 grams of tissue. The tissue was digested in either DMEM-Low glucose or DMEM-High glucose medium containing antimycotic and antibiotic (100 U/milliliter penicillin, 100 micrograms/milliliter streptomycin, 0.25 micrograms/milliliter amphotericin B) and digestion enzymes. In some experiments an enzyme mixture of collagenase and dispase ("C:D") was used containing collagenase (Sigma, St Louis, Mo.) at 500 Units/milliliter and dispase (Invitrogen) at 50 Units/milliliter in DMEM-Low glucose medium. In other experiments a mixture of collagenase, dispase and hyaluronidase (C:D:H) was used (collagenase, 500 Units/milliliter; dispase, 50 Units/milliliter; and hyaluronidase (Sigma), 5 Units/milliliter in DMEM-Low glucose). The conical tubes containing the tissue, medium, and digestion enzymes were incubated for 2 h at 37° C. in an orbital shaker (Environ, Brooklyn, N.Y.) at 225 rpm.

After digestion, the tissues were centrifuged at 150×g for 5 minutes, the resultant supernatant was aspirated off. The pellet was resuspended in 20 milliliters of Growth Medium with penicillin/streptomycin/amphotericin B. The cell suspension was filtered through a 70 micrometer nylon cell strainer (BD Biosciences), chased by a rinse with an additional 5 milliliters of Growth Medium. The total cell suspension was passed through a 40 micrometer nylon cell strainer (BD Biosciences) followed with an additional 5 milliliters of Growth Medium as a rinse.

The filtrate was resuspended in Growth Medium (total volume 50 milliliters) and centrifuged at 150×g for 5 minutes. The supernatant was aspirated and the cell pellet was resuspended in 50 milliliters of fresh Growth Medium. This process was repeated twice more. After the final centrifugation, supernatant was aspirated and the cell pellet was resuspended in 5 milliliters of fresh Growth Medium. A cell count was determined using the Trypan Blue Exclusion test. Cells were then cultured at standard conditions.

LIBERASE Cell Isolation. Cells were isolated from umbilicus tissues in DMEM-Low glucose medium with LIBERASE (Boehringer Mannheim Corp., Indianapolis, Ind.) (2.5 milligrams per milliliter, Blendzyme 3®; Roche Applied Sciences, Indianapolis, Ind.) and hyaluronidase (5 Units/milliliter, Sigma). Digestion of the tissue and isolation of the cells was as described for other protease digestions above, using the LIBERASE/hyaluronidase mixture in place of the C:D or C:D:H enzyme mixture. Tissue digestion with LIBERASE resulted in the isolation of cell populations from postpartum tissues that expanded readily.

Cell isolation using other enzyme combinations. Procedures were compared for isolating cells from the umbilical cord using differing enzyme combinations. Enzymes compared for digestion included: i) collagenase; ii) dispase; iii) hyaluronidase; iv) collagenase:dispase mixture (C;D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 1-1).

TABLE 1-1

Isolation of cells from umbilical cord tissue using varying enzyme combinations

| Enzyme Digest | Cells Isolated | Cell Expansion |
| --- | --- | --- |
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key:
+ = good,
++ = very good,
+++ = excellent,
X = no success under conditions tested Isolation of cells from residual blood in the cords. Other attempts were made to isolate pools of cells from umbilical cord by different approaches. In one instance umbilical cord was sliced and washed with Growth Medium to dislodge the blood clots and gelatinous material. The mixture of blood, gelatinous material and Growth Medium was collected and centrifuged at 150×g. The pellet was resuspended and seeded onto gelatin-coated flasks in Growth Medium. From these experiments a cell population was isolated that readily expanded.

Isolation of cells from cord blood. Cells have also been isolated from cord blood samples attained from NDRI. The isolation protocol used here was that of International Patent Application PCT/US2002/029971 by Ho et al (Ho, T. W. et al., WO2003025149 A2). Samples (50 milliliter and 10.5 milliliters, respectively) of umbilical cord blood (NDRI, Philadelphia Pa.) were mixed with lysis buffer (filter-sterilized 155 mM ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in complete minimal essential medium (Gibco, Carlsbad Calif.) containing 10 percent fetal bovine serum (Hyclone, Logan Utah), 4 millimolar glutamine (Mediatech Herndon, Va.), 100 Units penicillin per 100 milliliters and 100 micrograms streptomycin per 100 milliliters (Gibco, Carlsbad, Calif.). The resuspended cells were centrifuged (10 minutes at 200×g), the supernatant was aspirated, and the cell pellet washed in complete medium. Cells were seeded directly into either T75 flasks (Corning, N.Y.), T75 laminin-coated flasks, or T175 fibronectin-coated flasks (both Becton Dickinson, Bedford, Mass.).

Isolation of cells using different enzyme combinations and growth conditions. To determine whether cell populations could be isolated under different conditions and expanded under a variety of conditions immediately after isolation, cells were digested in Growth Medium with or without 0.001 percent (v/v) 2-mercaptoethanol (Sigma, St. Louis, Mo.), using the enzyme combination of C:D:H, according to the procedures provided above. Placental-derived cells so isolated were seeded under a variety of conditions. All cells were grown in the presence of penicillin/streptomycin. (Table 1-2).

Isolation of cells using different enzyme combinations and growth conditions. In all conditions cells attached and expanded well between passage 0 and 1 (Table 1-2). Cells in conditions 5-8 and 13-16 were demonstrated to proliferate well up to 4 passages after seeding at which point they were cryopreserved and banked.

Results

Cell isolation using different enzyme combinations. The combination of C:D:H, provided the best cell yield following isolation, and generated cells which expanded for many more generations in culture than the other conditions (Table 1). An expandable cell population was not attained using collagenase or hyaluronidase alone. No attempt was made to determine if this result is specific to the collagen that was tested.

Isolation of cells using different enzyme combinations and growth conditions. Cells attached and expanded well between passage 0 and 1 under all conditions tested for enzyme digestion and growth (Table 2). Cells in experimental conditions 5-8 and 13-16 proliferated well up to 4 passages after seeding, at which point they were cryopreserved. All cells were banked for further investigation.

Isolation of cells from residual blood in the cords. Nucleated cells attached and grew rapidly. These cells were analyzed by flow cytometry and were similar to cells obtained by enzyme digestion.

Isolation of cells from cord blood. The preparations contained red blood cells and platelets. No nucleated cells attached and divided during the first 3 weeks. The medium was changed 3 weeks after seeding and no cells were observed to attach and grow.

Summary. Populations of cells can be derived from umbilical cord and placental tissue efficiently using the enzyme combination collagenase (a matrix metalloprotease),dispase (a neutral protease) and hyaluronidase (a mucolytic enzyme that breaks down hyaluronic acid). LIBERASE, which is a Blendzyme®, may also be used. Specifically, Blendzyme 3®, which is collagenase (4 Wunsch units/g) and thermolysin (1714 casein Units/g) was also used together with hyaluronidase to isolate cells. These cells expanded readily over many passages when cultured in Growth Medium on gelatin coated plastic.

Cells were also isolated from residual blood in the cords, but not cord blood. The presence of cells in blood clots washed from the tissue, that adhere and grow under the conditions used, may be due to cells being released during the dissection process.

TABLE 1-2

Isolation and culture expansion of postpartum cells under varying conditions:

| Condition | Medium | 15% FBS | BME | Gelatin | 20% O2 | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/mL) |
| 6 | DMEM-Lg | N (2%) | Y | N (Laminin) | N (5%) | EGF/FGF (20 ng/mL) |
| 7 | DMEM-Lg | N (2%) | Y | N (Fibrone) | Y | PDGF/VEGF |
| 8 | DMEM-Lg | N (2%) | Y | N (Fibrone) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/mL) |
| 14 | DMEM-Lg | N (2%) | N | N (Laminin) | N (5%) | EGF/FGF (20 ng/mL) |
| 15 | DMEM-Lg | N (2%) | N | N (Fibrone) | Y | PDGF/VEGF |
| 16 | DMEM-Lg | N (2%) | N | N (Fibrone) | N (5%) | PDGF/VEGF |

EXAMPLE 2

Growth Characteristics of Postpartum-Derived Cells

The cell expansion potential of postpartum-derived cells (PPDCs) was compared to other populations of isolated stem cells. The process of cell expansion to senescence is referred to as Hayflick's limit (Hayflick L. 1974a, 1974b). Postpartum-derived cells are highly suited for therapeutic use because they can be readily expanded to sufficient cell numbers.

Materials and Methods

Gelatin-coating flasks. Tissue culture plastic flasks were coated by adding 20 milliliters 2% (w/v) porcine gelatin (Type B: 225 Bloom; Sigma, St Louis, Mo.) to a T75 flask (Corning, Corning, N.Y.) for 20 minutes at room temperature. After removing the gelatin solution, 10 milliliters phosphate-buffered saline (PBS) (Invitrogen, Carlsbad, Calif.) was added and then aspirated.

Comparison of expansion potential of PPDCs with other cell populations. For comparison of growth expansion potential the following cell populations were utilized; i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot # 9F0844; Cambrex, Walkersville, Md.); iv) Umbilicus-derived cells; and v) Placenta-derived cells. Cells were initially seeded at 5,000 cells/cm$^2$ on gelatin-coated T75 flasks in Growth Medium with penicillin/streptomycin/amphotericin B. For subsequent passages, cell cultures were treated as follows. After trypsinization, viable cells were counted after Trypan Blue staining. Cell suspension (50 microliters) was combined with Trypan Blue (50 milliliters, Sigma, St. Louis Mo.). Viable cell numbers were estimated using a hemocytometer.

Following counting, cells were seeded at 5,000 cells/cm$^2$ onto gelatin-coated T 75 flasks in 25 milliliters of fresh Growth Medium. Cells were grown under standard conditions at 37° C. The Growth Medium was changed twice per week. When cells reached about 85 percent confluence they were passaged; this process was repeated until the cells reached senescence.

At each passage, cells were trypsinized and counted. The viable cell yield, population doubling [ln(cell final/cell initial)/ln 2] and doubling time (time in culture (h)/population doubling) were calculated. For the purposes of determining optimal cell expansion, the total cell yield per passage was determined by multiplying the total yield for the previous passage by the expansion factor for each passage (i.e., expansion factor=cell final/cell initial).

Expansion potential of cell banks at low density. The expansion potential of cells banked at passage 10 was also tested, using a different set of conditions. Normal dermal skin fibroblasts (cc-2509 lot # 9F0844; Cambrex, Walkersville, Md.), umbilicus-derived cells, and placenta-derived cells were tested. These cell populations had been banked at passage 10 previously, having been cultured at 5,000 cells/cm$^2$ and grown to confluence at each passage to that point. The effect of cell density on the cell populations following cell thaw at passage 10 was determined. Cells were thawed under standard conditions and counted using Trypan Blue staining. Thawed cells were then seeded at 1000 cells/cm$^2$ in DMEM: Low glucose Growth Medium with antibiotic/antimycotic as described above. Cells were grown under standard atmospheric conditions at 37° C. Growth Medium was changed twice a week and cells were passaged as they reached about 85% confluence. Cells were subsequently passaged until senescence, i.e., until they could not be expanded any further. Cells were trypsinized and counted at each passage. The cell yield, population doubling (ln(cell final/cell initial)/ln 2) and doubling time (time in culture (h)/population doubling). The total cell yield per passage was determined by multiplying total yield for the previous passage by the expansion factor for each passage (i.e., expansion factor=cell final/cell initial).

Expansion of PPDCs at low density from initial cell seeding. The expansion potential of freshly isolated PPDCs under low cell seeding conditions was tested. PPDDs were prepared as described herein. Cells were seeded at 1000 cells/cm$^2$ and passaged as described above until senescence. Cells were grown under standard atmospheric conditions at 37° C. Growth Medium was changed twice per week. Cells were passaged as they reached about 85% confluence. At each passage, cells were trypsinized and counted by Trypan Blue staining. The cell yield, population doubling (ln(cell final/cell initial)/ln 2) and doubling time (time in culture (h)/population doubling) were calculated for each passage. The total cell yield per passage was determined by multiplying the total yield for the previous passage by the expansion factor for each passage (i.e. expansion factor=cell final/cell initial). Cells were grown on gelatin and non-gelatin coated flasks.

Expansion of clonal neonatal placenta-derived cells. Cloning was used in order to expand a population of neonatal cells from placental tissue. Following isolation of three differential cell populations from the placenta (as described herein), these cell populations were expanded under standard growth conditions and then karyotyped to reveal the identity of the isolated cell populations. Because the cells were isolated from a mother who delivered a boy, it was straightforward to distinguish between the male and female chromosomes by performing metaphase spreads. These experiments demonstrated that fetal-aspect cells were karyotype positive for neonatal phenotpye, mid-layer cells were karyotype positive for both neonatal and maternal phenotypes and maternal-aspect cells were karyotype positive for maternal cells.

Expansion of cells in low oxygen culture conditions. It has been demonstrated that low oxygen cell culture conditions can improve cell expansion in certain circumstances (US20040005704). To determine if cell expansion of PPDCs could be improved by altering cell culture conditions, cultures of umbilical-derived cells were grown in low oxygen conditions. Cells were seeded at 5000 cells/cm$^2$ in Growth Medium on gelatin coated flasks. Cells were initially cultured under standard atmospheric conditions through passage 5, at which point they were transferred to low oxygen (5% O$_2$) culture conditions.

Other growth conditions. In other protocols, cells were expanded on non-coated, collagen-coated, fibronectin-coated, laminin-coated and extracellular matrix protein-coated plates. Cultures have been demonstrated to expand well on these different matrices.

Results

Comparison of expansion potential of PPDCs with other stem cell and non-stem cell populations. Both umbilical-derived and placenta-derived cells expanded for greater than 40 passages generating cell yields of >1E17 cells in 60 days. In contrast, MSCs and fibroblasts senesced after <25 days and <60 days, respectively. Although adipose-derived cells expanded for almost 60 days they generated total cell yields of 4.5E12. Thus, when seeded at 5000 cells/cm$^2$ under the experimental conditions utilized, postpartum-derived cells expanded much better than the other cell types grown under the same conditions (Table 2-1).

TABLE 2-1

Growth characteristics for different cell populations grown to senescence

| Cell Type | Senescence | Total Population Doublings | Total Cell Yield |
|---|---|---|---|
| MSC | 24 d | 8 | 4.72 E7 |
| Adipose | 57 d | 24 | 4.5 E12 |
| Fibroblasts | 53 d | 26 | 2.82 E13 |
| Umbilicus | 65 d | 42 | 6.15 E17 |
| Placenta | 80 d | 46 | 2.49 E19 |

Expansion potential of cell banks at low density. Umbilicus-derived, placenta-derived and fibroblast cells expanded for greater than 10 passages generating cell yields of >1E11 cells in 60 days (Table 2-2). After 60 days under these conditions the fibroblasts became senescent whereas the umbilicus-derived and placenta-derived cell populations senesced after 80 days, completing >50 and >40 population doublings respectively.

TABLE 2-2

Growth characteristics for different cell populations using low density growth expansion from passage 10 till senescence

| Cell Type | Senescence | Total Population Doublings | Total Cell Yield |
|---|---|---|---|
| Fibroblast (P10) | 80 d | 43.68 | 2.59 E11 |
| Umbilicus (P10) | 80 d | 53.6 | 1.25 E14 |
| Placenta (P10) | 60 d | 32.96 | 6.09 E12 |

Expansion of PPDCs at low density from initial cell seeding. PPDCs were expanded at low density (1,000 cells/cm$^2$) on gelatin-coated and uncoated plates or flasks. Growth potential of these cells under these conditions was good. The cells expanded readily in a log phase growth. The rate of cell expansion was similar to that observed when placenta-derived cells were seeded at 5000 cells/cm$^2$ on gelatin-coated flasks in Growth Medium. No differences were observed in cell expansion potential between culturing on either uncoated flasks or gelatin-coated flasks. However, cells appeared phenotypically much smaller on gelatin-coated flasks and more larger cell phenotypes were observed on uncoated flasks.

Expansion of clonal neonatal or maternal placenta-derived cells. A clonal neonatal or maternal cell population can be expanded from placenta-derived cells isolated from the neonatal aspect or the maternal aspect, respectively, of the placenta. Cells are serially diluted and then seeded onto gelatin-coated plates in Growth medium for expansion at 1 cell/well in 96-well gelatin coated plates. From this initial cloning, expansive clones are identified, trypsinized, and reseeded in 12-well gelatin-coated plates in Growth medium and then subsequently passaged into T25 gelatin-coated flasks at 5,000 cells/cm$^2$ in Growth medium. Subcloning is performed to ensure that a clonal population of cells has been identified. For subcloning experiments, cells are trypsinized and reseeded at 0.5 cells/well. The subclones that grow well are expanded in gelatin-coated T25 flasks at 5,000 cells cm$^2$/flask. Cells are passaged at 5,000 cells cm$^2$/T75 flask. The growth characteristics of a clone may be plotted to demonstrate cell expansion. Karyotyping analysis can confirm that the clone is either neonatal or maternal.

Expansion of cells in low oxygen culture conditions. Cells expanded well under the reduced oxygen conditions, however, culturing under low oxygen conditions did not appear to have a significant effect on cell expansion of PPDCs under the conditions used.

Summary. Cell expansion conditions comprising growing isolated postpartum-derived cells at densities of about 5000 cells/cm$^2$, in Growth Medium on gelatin-coated or uncoated flasks, under standard atmospheric oxygen, are sufficient to generate large numbers of cells at passage 11. Furthermore, the data suggests that the cells can be readily expanded using lower density culture conditions (e.g. 1000 cells/cm$^2$). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations. Under the conditions utilized, while the expansion potential of MSC and adipose-derived cells is limited, postpartum-derived cells expand readily to large numbers.

References for Example 2
1) Hayflick L. 1974a. *J Am Geriatr Soc.* 22:1-12.
2) Hayflick L. 1974b. *Gerontologist.* 14:37-45.
3) U.S. Patent publication US20040058412
4) U.S. Patent publication US20040048372
5) U.S. Patent publication US20040005704.

EXAMPLE 3

Evaluation of Growth Media for Placenta-Derived Cells

Several cell culture media were evaluated for their ability to support the growth of placenta-derived cells. The growth of placenta-derived cells in normal (20%) and low (5%) oxygen was assessed after 3 days using the MTS calorimetric assay.

Methods & Materials

Placenta-derived cells at passage 8 (P8) were seeded at 1×10$^3$ cells/well in 96 well plates in Growth Medium with penicillin/streptomycin. After 8 hours the medium was changed as described below and cells were incubated in normal (atmospheric) or low (5%, v/v) oxygen at 37° C., 5% CO$_2$ for 48 hours. MTS was added to the culture medium (CELL-TITER 96 AQueous One Solution Cell Proliferation Assay, Promega, Madison, Wis.) for 3 hours and the absorbance measured at 490 nanometers (Molecular Devices, Sunnyvale Calif.).

TABLE 3-1

| Culture Media | | |
|---|---|---|
| Culture Medium | Supplier | Added fetal bovine serum % (v/v) |
| DMEM low glucose | Gibco Carlsbad CA | 0, 2 10 |
| DMEM high glucose | Gibco | 0, 2 10 |
| RPMI 1640 | Mediatech, Inc. Herndon, VA | 0, 2 10 |
| Cell gro-free (Serum-free, Protein-free | Mediatech, Inc. | — |
| Ham's F10 | Mediatech, Inc. | 0, 2 10 |
| MSCGM (complete with serum) | Cambrex, Walkersville, MD | 0, 2 10 |
| Complete-serum free w/albumin | Mediatech, Inc. | — |
| Growth Medium | NA | — |
| Ham's F12 | Mediatech, Inc. | 0, 2 10 |
| Iscove's | Mediatech, Inc. | 0, 2 10 |
| Basal Medium Eagle's | Mediatech, Inc. | |
| DMEM/F12 (1:1) | Mediatech, Inc. | 0, 2 10 |

Results

Standard curves for the MTS assay established a linear correlation between an increase in absorbance and an increase in cell number. The absorbance values obtained were converted into estimated cell numbers and the change (%) relative to the initial seeding was calculated.

The Effect of Serum. The addition of serum to media at normal oxygen conditions resulted in a reproducible dose-dependent increase in absorbance and thus the viable cell number. The addition of serum to complete MSCGM resulted in a dose-dependent decrease in absorbance. In the media without added serum, cells only grew appreciably in CELL-GRO-FREE, Ham's F10 and DMEM.

The Effect of Oxygen. Reduced oxygen appeared to increase the growth rate of cells in Growth Medium, Ham's F10, and MSCGM. In decreasing order of growth, the media resulting in the best growth of the cells were Growth Medium>MSCGM>Iscove's+10% FBS=DMEM-H+10% FBS=Ham's F12+10% FBS=RPMI 1640+10% FBS.

Summary. Placenta-derived cells may be grown in a variety of culture media in normal or low oxygen. Short term growth of placenta-derived cells was determined in twelve basal media with 0, 2 and 10% (v/v) serum in 5% or atmospheric oxygen. In general, placenta-derived cells did not grow as well in serum-free conditions with the exception of Ham's F10 and CELLGRO-Free, which are also protein-free. Growth in these serum-free media was about 25-33% of the maximal growth observed with media containing 15% serum.

EXAMPLE 4

Growth of Postpartum-Derived Cells in Medium Containing D-Valine

It has been reported that medium containing D-valine instead of the normal L-valine isoform can be used to selectively inhibit the growth of fibroblast-like cells in culture (Hongpaisan, 2000; Sordillo et al., 1988). It was not previously known whether postpartum-derived cells could grow in medium containing D-valine.

Methods & Materials

Placenta-derived cells (P3), fibroblasts (P9) and umbilical-derived cells (P5) were seeded at $5 \times 10^3$ cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a Modified Growth Medium (DMEM with D-valine (special order Gibco), 15% (v/v) dialyzed fetal bovine serum (Hyclone, Logan, Utah), 0.001% (v/v) betamercaptoethanol (Sigma), penicillin/streptomycin (Gibco)).

Results

Placenta-derived, umbilical-derived, and fibroblast cells seeded in the D-valine-containing medium did not proliferate, unlike cells seeded in Growth Medium containing dialyzed serum. Fibroblasts cells changed morphologically, increasing in size and changing shape. All of the cells died and eventually detached from the flask surface after 4 weeks. These results indicate that medium containing D-valine is not suitable for selectively growing postpartum-derived cells.

References for Example 4
1) Hongpaisan J. 2000. *Cell Biol Int.* 24:1-7.
2) Sordillo L M, Oliver S P, Akers R M. 1988). *Cell Biol Int Rep.* 12:355-64.

EXAMPLE 5

Cryopreservation Media for Placenta-Derived Cells

Cryopreservation media for the cryopreservation of placenta-derived cells were evaluated.

Methods & Materials

Placenta-derived cells grown in Growth Medium in a gelatin-coated T75 flask were washed with PBS and trypsinized using 1 milliliter Trypsin/EDTA (Gibco). The trypsinization was stopped by adding 10 milliliters Growth Medium. The cells were centrifuged at 150×g, supernatant removed, and the cell pellet was resuspended in 1 milliliter Growth Medium. An aliquot of cell suspension, 60 microliters, was removed and added to 60 microliters trypan blue (Sigma). The viable cell number was estimated using a hemocytometer. The cell suspension was divided into four equal aliquots each containing $88 \times 10^4$ cells each. The cell suspension was centrifuged and resuspended in 1 milliliter of each media below and transferred into Cryovials (Nalgene).

1.) Growth Medium +10% (v/v) DMSO (Hybrimax, Sigma, St. Louis, Mo.)
2.) Cell Freezing medium w/DMSO, w/methyl cellulose, serum-free (C6295, Sigma, St. Louis, Mo.)
3.) Cell Freezing medium serum-free (C2639, Sigma, St. Louis, Mo.)
4.) Cell Freezing Medium w/glycerol (C6039, Sigma, St. Louis, Mo.)

The cells were cooled at approximately −1° C./min overnight in a −80° C. freezer using a "Mr Frosty" freezing container according to the manufacturer's instructions (Nalgene, Rochester, N.Y.). Vials of cells were transferred into liquid nitrogen for 2 days before thawing rapidly in a 37° C. water bath. The cells were added to 10 milliliters Growth Medium and centrifuged before the cell number and viability was estimated. Cells were seeded onto gelatin-coated flasks at 5,000 cells/cm$^2$ to determine whether the cells would attach and proliferate.

Results

The initial viability of the cells to be cryopreserved was assessed by trypan blue staining to be 100%. The initial viability of the cells to be cryopreserved was assessed by trypan blue staining to be 100%.

There was a commensurate reduction in cell number with viability for C6295 due to cells lysis. The viable cells cryopreserved in all four solutions attached, divided, and produced a confluent monolayer within 3 days. There was no discernable difference in estimated growth rate.

Summary. The cryopreservation of cells is one procedure available for preparation of a cell bank or a cell product. Four cryopreservation mixtures were compared for their ability to protect human placenta-derived cells from freezing damage. Dulbecco's modified Eagle's medium (DMEM) and 10% (v/v) dimethylsulfoxide (DMSO) is the preferred medium of those compared for cryopreservation of placenta-derived cells.

EXAMPLE 6

Karyotype Analysis of Postpartum-Derived Cells

Cell lines used in cell therapy are preferably homogeneous and free from any contaminating cell type. Cells used in cell therapy should have a normal chromosome number (46) and structure. To identify placenta- and umbilicus-derived cell lines that are homogeneous and free from cells of non-postpartum tissue origin, karyotypes of cell samples were analyzed.

Materials and Methods

PPDCs from postpartum tissue of a male neonate were cultured in Growth Medium containing penicillin/streptomycin. Postpartum tissue from a male neonate (X,Y) was selected to allow distinction between neonatal-derived cells and maternal derived cells (X,X). Cells were seeded at 5,000 cells per square centimeter in Growth Medium in a T25 flask (Corning, Corning, N.Y.) and expanded to 80% confluence. A T25 flask containing cells was filled to the neck with Growth Medium. Samples were delivered to a clinical cytogenetics laboratory by courier (estimated lab to lab transport time is one hour). Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted as exhibiting a normal appearance. Three of the sixteen cell lines analyzed exhibited a heterogeneous phenotype (XX and XY) indicating the presence of cells derived from both neonatal and maternal origins (Table 6-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

TABLE 6-1

Results of PPDC karyotype analysis

| Tissue | passage | Metaphase cells counted | Metaphase cells analyzed | Number of karyotype | ISCN Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-NC1 | 1 | 20 | 5 | 2 | 46, XY |
| Placenta-NC3 | 1 | 20 | 6 | 4 | 46, XY[2]/46, XX[18] |
| Placenta-NC4 | 1 | 20 | 5 | 2 | 46, XY |
| Placenta-NC15 | 1 | 20 | 5 | 2 | 46, XY |
| Placenta-NC20 | 1 | 20 | 5 | 2 | 46, XY |

Key:
N—Neonatal aspect;
V—villous region;
M—maternal aspect;
C—clone

Summary. Chromosome analysis identified placenta- and umbilicus-derived cellswhose karyotypes appeared normal as interpreted by a clinical cytogenetic laboratory. Karyotype analysis also identified cell lines free from maternal cells, as determined by homogeneous karyotype.

EXAMPLE 7

Evaluation of Human Postpartum-Derived Cell Surface Markers by Flow Cytometry

Characterization of cell surface proteins or "markers" by flow cytometry can be used to determine a cell line's identity. The consistency of expression can be determined from multiple donors, and in cells exposed to different processing and culturing conditions. Postpartum-derived cell (PPDC) lines isolated from the placenta and umbilicus were characterized (by flow cytometry), providing a profile for the identification of these cell lines.

Materials and Methods

Media and culture vessels. Cells were cultured in Growth Medium (Gibco Carlsbad, Calif.) with penicillin/streptomycin. Cells were cultured in plasma-treated T75, T150, and T225 tissue culture flasks (Corning, Corning, N.Y.) until confluent. The growth surfaces of the flasks were coated with gelatin by incubating 2% (w/v) gelatin (Sigma, St. Louis, Mo.) for 20 minutes at room temperature.

Antibody Staining and flow cytometry analysis. Adherent cells in flasks were washed in PBS and detached with Trypsin/EDTA. Cells were harvested, centrifuged, and resuspended in 3% (v/v) FBS in PBS at a cell concentration of $1 \times 10^7$ per milliliter. In accordance to the manufacture's specifications, antibody to the cell surface marker of interest (see below) was added to one hundred microliters of cell suspension and the mixture was incubated in the dark for 30 minutes at 4° C. After incubation, cells were washed with PBS and centrifuged to remove unbound antibody. Cells were resuspended in 500 microliter PBS and analyzed by flow cytometry. Flow cytometry analysis was performed with a FACScalibur instrument (Becton Dickinson, San Jose, Calif.).

The following antibodies to cell surface markers were used.

| Antibody | Manufacture | Catalog Number |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG-PE | Sigma | P-4685 |

Placenta and umbilicus comparison. Placenta-derived cells were compared to umbilicus-derive cells at passage 8.

Passage to passage comparison. Placenta- and umbilicus-derived cells were analyzed at passages 8, 15, and 20.

Donor to donor comparison. To compare differences among donors, placenta-derived cells from different donors were compared to each other, and umbilicus-derived cells from different donors were compared to each other.

Surface coating comparison. Placenta-derived cells cultured on gelatin-coated flasks was compared to placenta-derived cells cultured on uncoated flasks. Umbilicus-derived cells cultured on gelatin-coated flasks was compared to umbilicus-derived cells cultured on uncoated flasks.

Digestion enzyme comparison. Four treatments used for isolation and preparation of cells were compared. Cells isolated from placenta by treatment with 1) collagenase; 2) collagenase/dispase; 3) collagenase/hyaluronidase; and 4) collagenase/hyaluronidase/dispase were compared.

Placental layer comparison. Cells derived from the maternal aspect of placental tissue were compared to cells derived from the villous region of placental tissue and cells derived from the neonatal fetal aspect of placenta.

Results

Placenta vs. umbilicus comparison. Placenta- and umbilicus-derived cells analyzed by flow cytometry showed positive expression of CD10, CD13, CD44, CD73, CD 90, PDGFr-alpha and HLA-A, B, C, indicated by the increased values of fluorescence relative to the IgG control. These cells were negative for detectable expression of CD31, CD34, CD45, CD117, CD141, and HLA-DR, DP, DQ, indicated by fluorescence values comparable to the IgG control. Variations in fluorescence values of positive curves were accounted for. The mean (i.e. CD13) and range (i.e. CD90) of the positive curves showed some variation, but the curves appeared normal, confirming a homogenous population. Both curves individually exhibited values greater than the IgG control.

Passage to passage comparison—placenta-derived cells. Placenta-derived cells at passages 8, 15, and 20 analyzed by flow cytometry all were positive for expression of CD10, CD13, CD44, CD73, CD 90, PDGFr-alpha and HLA-A, B, C, as reflected in the increased value of fluorescence relative to the IgG control. The cells were negative for expression of CD31, CD34, CD45, CD117, CD141, and HLA-DR, DP, DQ having fluorescence values consistent with the IgG control.

Passage to passage comparison—umbilicus-derived cells. Umbilicus-derived cells at passage 8, 15, and 20 analyzed by flow cytometry all expressed CD10, CD13, CD44, CD73, CD 90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control.

Donor to donor comparison—placenta-derived cells. Placenta-derived cells isolated from separate donors analyzed by flow cytometry each expressed CD10, CD13, CD44, CD73, CD 90, PDGFr-alpha and HLA-A, B, C, with increased values of fluorescence relative to the IgG control. The cells were negative for expression of CD31, CD34, CD45, CD117, CD141, and HLA-DR, DP, DQ as indicated by fluorescence value consistent with the IgG control.

Donor to donor comparison—umbilicus derived cells. Umbilicus-derived cells isolated from separate donors analyzed by flow cytometry each showed positive expression of CD10, CD13, CD44, CD73, CD 90, PDGFr-alpha and HLA-A, B, C, reflected in the increased values of fluorescence relative to the IgG control. These cells were negative for expression of CD31, CD34, CD45, CD117, CD141, and HLA-DR, DP, DQ with fluorescence values consistent with the IgG control.

The effect of surface coating with gelatin on placenta-derived cells. Placenta-derived cells expanded on either gelatin-coated or uncoated flasks analyzed by flow cytometry all expressed of CD10, CD13, CD44, CD73, CD 90, PDGFr-alpha and HLA-A, B, C, reflected in the increased values of fluorescence relative to the IgG control. These cells were negative for expression of CD31, CD34, CD45, CD117, CD141, and HLA-DR, DP, DQ indicated by fluorescence values consistent with the IgG control.

The effect of surface coating with gelatin on umbilicus-derived cells. Umbilicus-derived cells expanded on gelatin and uncoated flasks analyzed by flow cytometry all were positive for expression of CD10, CD13, CD44, CD73, CD 90, PDGFr-alpha and HLA-A, B, C, with increased values of fluorescence relative to the IgG control. These cells were negative for expression of CD31, CD34, CD45, CD117, CD141, and HLA-DR, DP, DQ, with fluorescence values consistent with the IgG control.

Effect of enzyme digestion procedure used for preparation of the cells on the cell surface marker profile. Placenta-derived cells isolated using various digestion enzymes analyzed by flow cytometry all expressed CD10, CD13, CD44, CD73, CD 90, PDGFr-alpha and HLA-A, B, C, as indicated by the increased values of fluorescence relative to the IgG control. These cells were negative for expression of CD31, CD34, CD45, CD117, CD141, and HLA-DR, DP, DQ as indicated by fluorescence values consistent with the IgG control\

Placental layer comparison. Cells isolated from the maternal, villous, and neonatal layers of the placenta, respectively, analyzed by flow cytometry showed positive expression of CD10, CD13, CD44, CD73, CD 90, PDGFr-alpha and HLA-A, B, C, as indicated by the increased value of fluorescence relative to the IgG control. These cells were negative for expression of CD31, CD34, CD45, CD117, CD141, and HLA-DR, DP, DQ as indicated by fluorescence values consistent with the IgG control.

Summary. Analysis of placenta- and umbilicus-derived cells by flow cytometry has established of an identity of these cell lines. Placenta- and umbilicus-derived cells are positive for CD10, CD13, CD44, CD73, CD90, PDGFr-alpha, HLA-A, B, C and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges was observed, but all positive curves under all conditions tested were normal and expressed fluorescence values greater than the IgG control, thus confirming that the cells comprise a homogenous population that has positive expression of the markers.

EXAMPLE 8

Immunohistochemical Characterization of Postpartum Tissue Phenotypes

The phenotypes of cells found within human postpartum tissues, namely umbilical cord and placenta, was analyzed by immunohistochemistry.

Materials & Methods

Tissue Preparation. Human umbilical cord and placenta tissue was harvested and immersion fixed in 4% (w/v) paraformaldehyde overnight at 4° C. Immunohistochemistry was performed using antibodies directed against the following epitopes:vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 micrometers thick) using a standard cryostat (Leica Microsystems) and mounted onto glass slides for staining.

Immunohistochemistry. Immunohistochemistry was performed similar to previous studies (e.g., Messina, et al., 2003, Exper. Neurol. 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), Triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150; Santa Cruz Biotech). Cultures were washed, and 10 micromolar DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Umbilical cord characterization. Vimentin, desmin, SMA, CK18, vWF, and CD34 markers were expressed in a subset of the cells found within umbilical cord. In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers.

Placenta characterization. Vimentin, desmin, SMA, CK18, vWF, and CD34 were all observed within the placenta and regionally specific.

GROalpha, GCP-2, ox-LDL R1, and NOGO-A Tissue Expression. None of these markers were observed within umbilical cord or placental tissue.

Summary. Vimentin, desmin, alpha-smooth muscle actin, cytokeratin 18, von Willebrand Factor, and CD 34 are expressed in cells within human umbilical cord and placenta.

EXAMPLE 9

Analysis of Postpartum Tissue-Derived Cells Using Oligonucleotide Arrays

Affymetrix GENECHIP arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

Materials and Methods

Isolation and culture of cells. Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth Medium (using DMEM-LG) on gelatin-coated tissue culture plastic flasks. The cultures were incubated at 37° C. with 5% $CO_2$.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen). The cells were grown on standard tissue-treated plastic.

Human mesenchymal stem cells (hMSC) were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human iliac crest bone marrow was received from NDRI with patient consent. The marrow was processed according to the method outlined by Ho, et al. (WO03/025149). The marrow was mixed with lysis buffer (155 mM $NH_4Cl$, 10 mM $KHCO_3$, and 0.1 mM EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 mM glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at 5×104 cells/cm². The cells were incubated at 37° C. with 5% CO2 at either standard atmospheric O2 or at 5% O2. Cells were cultured for 5 days without a media change. Media and non-adherent cells were removed after 5 days of culture. The adherent cells were maintained in culture.

Isolation of mRNA and GENECHIP Analysis. Actively growing cultures of cells were removed from the flasks with a cell scraper in cold PBS. The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA, which was then transcribed into cRNA and biotin-labeled. The biotin-labeled cRNA was hybridized with HG-U133A GENECHIP oligonucleotide array (Affymetrix, Santa Clara Calif.). The hybridization and data collection was performed according to the manufacturer's specifications. Analyses were performed using "Significance Analysis of Microarrays" (SAM) version 1.21 computer software (Stanford University; Tusher, V. G. et al., 2001, Proc. Natl. Acad. Sci. USA 98: 5116-5121).

Results

Fourteen different populations of cells were analyzed. The cells along with passage information, culture substrate, and culture media are listed in Table 9-1.

TABLE 9-1

Cells analyzed by the microarray study. Cell lines are listed by identification code along with passage at time of analysis, cell growth substrate and growth medium.

| Cell Population | Passage | Substrate | Medium |
|---|---|---|---|
| Umbilicus (022803) | 2 | Gelatin | DMEM, 15% FBS, 2-ME |
| Umbilicus (042103) | 3 | Gelatin | DMEM, 15% FBS, 2-ME |
| Umbilicus (071003) | 4 | Gelatin | DMEM, 15% FBS, 2-ME |
| Placenta (042203) | 12 | Gelatin | DMEM, 15% FBS, 2-ME |
| Placenta (042903) | 4 | Gelatin | DMEM, 15% FBS, 2-ME |
| Placenta (071003) | 3 | Gelatin | DMEM, 15% FBS, 2-ME |
| ICBM (070203) (5% O2) | 3 | Plastic | MEM, 10% FBS |
| ICBM (062703) (std. O2) | 5 | Plastic | MEM, 10% FBS |
| ICBM (062703) (5% O2) | 5 | Plastic | MEM, 10% FBS |
| hMSC (Lot 2F1655) | 3 | Plastic | MSCGM |
| hMSC (Lot 2F1656) | 3 | Plastic | MSCGM |
| hMSC (Lot 2F 1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by a Principle Component Analysis, analyzing the 290 genes that were differentially expressed in the cells. This analysis allows for a relative comparison for the similarities between the populations. Table 9-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes (i.e., the greater the distance, the less similarity exists).

TABLE 9-2

Euclidian Distances for the Cell Pairs

| | |
|---|---|
| ICBM-hMSC | 24.71 |
| Placental-umbilical | 25.52 |
| ICBM-fibroblast | 36.44 |
| ICBM-fibroblast-placenta | 37.09 |
| Fibroblast-MSC | 39.63 |
| ICBM-umbilical | 40.15 |
| Fibroblast-umbilical | 41.59 |
| MSC-placenta | 42.84 |
| MSC-umbilical | 46.86 |
| ICBM-placenta | 48.41 |

Tables 9-3, 9-4, and 9-5 show the expression of genes increased in placenta-derived cells (Table 9-3), increased in umbilicus-derived cells (Table 9-4), and reduced in umbilicus- and placenta-derived cells (Table 9-5). The column entitled "Probe Set ID" refers to the manufacturer's identification code for the sets of several oligonucleotide probes located on a particular site on the chip, which hybridize to the named gene (column "Gene Name"), comprising a sequence that can be found within the NCBI (GenBank) database at the specified accession number (column "NCBI Accession Number").

TABLE 9-3

Genes shown to have specifically increased expression in the placenta-derived cells as compared to other cell lines assayed
Genes Increased in Placenta-Derived Cells

| Probe Set ID | Gene Name | NCBI Accession Number |
|---|---|---|
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | Rennin | NM_000537 |
| 210004_at | oxidized low density lipoprotein (lectin-like) receptor 1 | AF035776 |
| 214993_at | Homo sapiens, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | Homo sapiens mRNA; cDNA DKFZp547K1113 (from clone DKFZp547K1113) | AI246730 |

TABLE 9-4

Genes shown to have specifically increased expression in the umbilicus-derived cells as compared to other cell lines assayed
Genes Increased in Umbilicus-Derived Cells

| Probe Set ID | Gene Name | NCBI Accession Number |
|---|---|---|
| 202859_x_at | interleukin 8 | NM_000584 |
| 211506_s_at | interleukin 8 | AF043337 |
| 210222_s_at | reticulon 1 | BC000314 |
| 204470_at | chemokine (C—X—C motif) ligand 1 (melanoma growth stimulating activity | NM_001511 |
| 206336_at | chemokine (C—X—C motif) ligand 6 (granulocyte chemotactic protein 2) | NM_002993 |
| 207850_at | Chemokine (C—X—C motif) ligand 3 | NM_002090 |
| 203485_at | reticulon 1 | NM_021136 |
| 202644_s_at | tumor necrosis factor, alpha-induced protein 3 | NM_006290 |

TABLE 9-5

Genes shown to have decreased expression in umbilicus- and placenta-derived cells as compared to other cell lines assayed
Genes Decreased in Umbilicus- and Placenta-Derived Cells

| Probe Set ID | Gene name | NCBI Accession Number |
|---|---|---|
| 210135_s_at | short stature homeobox 2 | AF022654.1 |
| 205824_at | heat shock 27 kDa protein 2 | NM_001541.1 |
| 209687_at | chemokine (C—X—C motif) ligand 12 (stromal cell-derived factor 1) | U19495.1 |
| 203666_at | chemokine (C—X—C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeo box 2 (growth arrest-specific homeo box) | NM_005924.1 |
| 205817_at | sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |

TABLE 9-5-continued

Genes shown to have decreased expression in umbilicus- and placenta-derived cells as compared to other cell lines assayed
Genes Decreased in Umbilicus- and Placenta-Derived Cells

| Probe Set ID | Gene name | NCBI Accession Number |
|---|---|---|
| 205200_at | tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | interleukin 11 receptor, alpha | NM_004512.1 |
| 202465_at | procollagen C-endopeptidase enhancer | NM_002593.2 |
| 203706_s_at | frizzled homolog 7 (*Drosophila*) | NM_003507.1 |
| 212736_at | hypothetical gene BC008967 | BE299456 |
| 214587_at | collagen, type VIII, alpha 1 | BE877796 |
| 201645_at | tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | Synaptic vesicle glycoprotein 2 | NM_014849.1 |
| 213909_at | *Homo sapiens* cDNA FLJ12280 fis, clone MAMMA1001744 | AU147799 |
| 206315_at | Cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | sine oculis homeobox homolog 2 (*Drosophila*) | NM_016932.1 |
| 213435_at | KIAA1034 protein | AB028957.1 |
| 206115_at | Early growth response 3 | NM_004430.1 |
| 213707_s_at | distal-less homeo box 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | proenkephalin | NM_006211.1 |
| 205422_s_at | integrin, beta-like 1 (with EGF-like repeat domains) | NM_004791.1 |
| 214927_at | *Homo sapiens* mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | *Homo sapiens* mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | insulin-like growth factor binding protein 2, 36 kDa | NM_000597.1 |

Tables 9-6, 9-7, and 9-8 show the expression of genes increased in human fibroblasts (Table 9-6), ICBM cells (Table 9-7), and MSCs (Table 9-8).

TABLE 9-6

Genes that were shown to have increased expression in fibroblasts as compared to the other cell lines assayed.
Genes increased in fibroblasts dual specificity phosphatase 2
KIAA0527 protein
*Homo sapiens* cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
*Homo sapiens* cDNA: FLJ23564 fis, clone LNG10773
*Homo sapiens* mRNA; cDNA DKFZp564A072 (from clone DKFZp564A072)
LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [Homo sapiens]
transforming growth factor, beta 2
hypothetical protein MGC29643
antigen identified by monoclonal antibody MRC OX-2
putative X-linked retinopathy protein

TABLE 9-7

Genes that were shown to have increased expression in the ICBM-derived cells as compared to the other cell lines assayed.
a) Genes Increased In ICBM Cells cardiac ankyrin repeat protein
MHC class I region ORF
integrin, alpha 10
hypothetical protein FLJ22362
UDP-N-acetyl-alpha-D-galactosamine:polypeptide N-acetylgalactosaminyltransferase 3 (GalNAc-T3)
interferon-induced protein 44
SRY (sex determining region Y)-box 9 (campomelic dysplasia, autosomal sex-reversal)
keratin associated protein 1-1
hippocalcin-like 1
jagged 1 (Alagille syndrome)
proteoglycan 1, secretory granule

TABLE 9-8

Genes that were shown to have increased expression in the MSC cells as compared to the other cell lines assayed.
b) Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
*Homo sapiens* cDNA FLJ12232 fis, clone MAMMA1001206
*Homo sapiens* cDNA FLJ34668 fis, clone LIVER2000775
jun B proto-oncogene TABLE 9-8-continued Genes that were shown to have increased expression in the MSC cells as compared to the other cell lines assayed.
b) Genes Increased In MSC Cells B-cell CLL/lymphoma 6 (zinc finger protein 51)
zinc finger protein 36, C3H type, homolog (mouse)

Summary. The present examination was performed to provide a molecular characterization of the postpartum cells derived from umbilical cord and placenta. This analysis included cells derived from three different umbilical cords and three different placentas. The examination also included two different lines of dermal fibroblasts, three lines of mesenchymal stem cells, and three lines of iliac crest bone marrow cells. The mRNA that was expressed by these cells was analyzed using an oligonucleotide array that contained probes for 22,000 genes. Results showed that 290 genes are differentially expressed in these five different cell types. These genes include ten genes that are specifically increased in the placenta-derived cells and seven genes specifically increased in the umbilical cord-derived cells. Fifty-four genes were found to have specifically lower expression levels in placenta and umbilical cord, as compared with the other cell types. The expression of selected genes has been confirmed by PCR (see the example that follows). These results demonstrate that the postpartum-derived cells have a distinct gene expression profile, for example, as compared to bone marrow-derived cells and fibroblasts.

EXAMPLE 10

Cell Markers in Postpartum-Derived Cells

In the preceding example, similarities and differences in cells derived from the human placenta and the human umbilical cord were assessed by comparing their gene expression profiles with those of cells derived from other sources (using an oligonucleotide array). Six "signature" genes were identified: oxidized LDL receptor 1, interleukin-8, rennin, reticulon, chemokine receptor ligand 3 (CXC ligand 3), and granulocyte chemotactic protein 2 (GCP-2). These "signature" genes were expressed at relatively high levels in postpartum-derived cells.

The procedures described in this example were conducted to verify the microarray data and find concordance/discordance between gene and protein expression, as well as to establish a series of reliable assay for detection of unique identifiers for placenta- and umbilicus-derived cells.
Methods & Materials Cells. Placenta-derived cells (three isolates, including one isolate predominately neonatal as identified by karyotyping analysis), umbilicus-derived cells (four isolates), and Normal Human Dermal Fibroblasts (NHDF; neonatal and adult) grown in Growth Medium with penicillin/streptomycin in a gelatin-coated T75 flask. Mesechymal Stem Cells (MSCs) were grown in Mesenchymal Stem Cell Growth Medium Bullet kit (MSCGM; Cambrex, Walkerville, Md.).

For the IL-8 protocol, cells were thawed from liquid nitrogen and plated in gelatin-coated flasks at 5,000 cells/cm$^2$, grown for 48 hours in Growth Medium and then grown for further 8 hours in 10 milliliters of serum starvation medium [DMEM-low glucose (Gibco, Carlsbad, Calif.), penicillin/streptomycin (Gibco, Carlsbad, Calif.) and 0.1% (w/v) Bovine Serum Albumin (BSA; Sigma, St. Louis, Mo.)]. After this treatment RNA was extracted and the supernatants were centrifuged at 150×g for 5 minutes to remove cellular debris. Supernatants were then frozen at −80° C. for ELISA analysis.

Cell culture for ELISA assay. Postpartum cells derived from placenta and umbilicus, as well as human fibroblasts derived from human neonatal foreskin were cultured in Growth Medium in gelatin-coated T75 flasks. Cells were frozen at passage 11 in liquid nitrogen. Cells were thawed and transferred to 15-milliliter centrifuge tubes. After centrifugation at 150×g for 5 minutes, the supernatant was discarded. Cells were resuspended in 4 milliliters culture medium and counted. Cells were grown in a 75 cm$^2$ flask containing 15 milliliters of Growth Medium at 375,000 cell/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of tyrpsin/EDTA (Gibco, Carlsbad, Calif.) was added each flask. After cells detached from the flask, trypsin activity was neutralized with 8 milliliters of Growth Medium. Cells were transferred to a 15 milliliters centrifuge tube and centrifuged at 150×g for 5 minutes. Supernatant was removed and 1 milliliter Growth Medium was added to each tube to resuspend the cells. Cell number was estimated using a hemocytometer.

ELISA assay. The amount of IL-8 secreted by the cells into serum starvation medium was analyzed using ELISA assays (R&D Systems, Minneapolis, Minn.). All assays were tested according to the instructions provided by the manufacturer.

Total RNA isolation. RNA was extracted from confluent postpartum-derived cells and fibroblasts or for IL-8 expression from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 U/sample) (Sigma St. Louis, Mo.). RNA was eluted with 50 microliters DEPC-treated water and stored at −80° C.

Reverse transcription. RNA was also extracted from human placenta and umbilicus. Tissue (30 milligram) was suspended in 700 microliters of buffer RLT containing 2-mercaptoethanol. Samples were mechanically homogenized and the RNA extraction proceeded according to manufacturer's specification. RNA was extracted with 50 microliters of DEPC-treated water and stored at −80° C. RNA was reversed transcribed using random hexamers with the TaqMan reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells (signature genes—including oxidized LDL receptor, interleukin-8, rennin and reticulon), were further investigated using real-time and conventional PCR.

Real-time PCR. PCR was performed on cDNA samples using Assays-on-Demand™ gene expression products: oxidized LDL receptor (Hs00234028); rennin (Hs00166915); reticulon (Hs00382515); CXC ligand 3 (Hs00171061); GCP-2 (Hs00605742); IL-8 (Hs00174103); and GAPDH (Applied Biosystems, Foster City, Calif.) were mixed with cDNA and TaqMan Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 min and 95° C. for 10 min, followed by 40 cycles of 95° C. for 15 sec and 60° C. for 1 min. PCR data was analyzed according to manufacturer's specifications (User Bulletin #2 from Applied Biosystems for ABI Prism 7700 Sequence Detection System).

Conventional PCR. Conventional PCR was performed using an ABI PRISM 7700 (Perkin Elmer Applied Biosystems, Boston, Mass., USA) to confirm the results from real-time PCR. PCR was performed using 2 microliters of cDNA solution, 1× AmpliTaq Gold universal mix PCR reaction buffer (Applied Biosystems, Foster City, Calif.) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for rennin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 1. Primer concentration in the final PCR reaction was 1 micromolar except for GAPDH, which was 0.5 micromolar. GAPDH primers were the same as real-time PCR, except that the manufacturer's TaqMan probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length Polaroid camera (VWR International, South Plainfield, N.J.).

TABLE 10-1

Primers used

| c) Primer name | Primers |
|---|---|
| Oxidized LDL receptor | S: 5'-GAGAAATCCAAAGAGCAAATGG-3' (SEQ ID NO: 1) <br> A: 5'-AGAATGGAAAACTGGAATAGG-3' (SEQ ID NO: 2) |
| Renin | S: 5'-TCTTCGATGCTTCGGATTCC-3' (SEQ ID NO: 3) <br> A: 5'-GAATTCTCGGAATCTCTGTTG-3' (SEQ ID NO: 4) |
| Reticulon | S: 5'- TTACAAGCAGTGCAGAAAACC-3' (SEQ ID NO: 5) <br> A: 5'- AGTAAACATTGAAACCACAGCC-3' (SEQ ID NO: 6) |
| Interleukin-8 | S: 5'- TCTGCAGCTCTGTGTGAAGG-3' (SEQ ID NO: 7) <br> A: 5'-CTTCAAAAACTTCTCCACAACC- 3' (SEQ ID NO: 8) |
| Chemokine (CXC) ligand 3 | S: 5'- CCCACGCCACGCTCTCC-3' (SEQ ID NO: 9) <br> A: 5'-TCCTGTCAGTTGGTGCTCC -3' (SEQ ID NO: 10) |

Immunofluorescence. PPDCs were fixed with cold 4% (w/v) paraformaldehyde (Sigma-Aldrich, St. Louis, Mo.) for 10 minutes at room temperature. One isolate each of umbilicus- and placenta-derived cells at passage 0 (P0) (directly after isolation) and passage 11 (P11) (two isolates of placenta-derived, two isolates of umbilicus-derived cells) and fibroblasts (P11) were used. Immunocytochemistry was performed using antibodies directed against the following epitopes:vimentin (1:500, Sigma, St. Louis, Mo.), desmin (1:150; Sigma—raised against rabbit; or 1:300; Chemicon, Temecula, Calif.—raised against mouse,), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum cells: anti-human GRO alpha—PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG—Texas Red (1:250; Molecular Probes, Eugene, Oreg.) and/or goat anti-rabbit IgG—Alexa 488 (1:250; Molecular Probes) or donkey anti-goat IgG—FITC (1:150, Santa Cruz Biotech). Cultures were then washed and 10 micromolar DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution. Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of Cells for Facs Analysis. Adherent Cells in Flasks were Washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$ per milliliter. One hundred microliter aliquots were delivered to conical tubes. Cells stained for intracellular antigens were permeablized with Perm/Wash buffer (BD Pharmingen, San Diego, Calif.). Antibody was added to aliquots as per manufactures specifications and the cells were incubated for in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufactures specification and the cells were incubated in the dark for 30 minutes at 4° C. After incubation, cells were washed with PBS and centrifuged to remove excess secondary antibody. Washed cells were resuspended in 0.5 milliliters PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), Donkey against Goat IgG (sc-3743; Santa Cruz, Biotech.). Flow cytometry analysis was performed with FACScalibur (Becton Dickinson San Jose, Calif.).

Results

Results of real-time PCR for selected "signature" genes performed on cDNA from cells derived from human placentae, adult and neonatal fibroblasts and Mesenchymal Stem Cells (MSCs) indicate that both oxidized LDL receptor and rennin were expressed at higher level in the placenta-derived cells as compared to other cells. The data obtained from real-time PCR were analyzed by the ΔΔCT method and expressed on a logarithmic scale. Levels of reticulon and oxidized LDL receptor expression were higher in umbilicus-derived cells as compared to other cells. No significant difference in the expression levels of CXC ligand 3 and GCP-2 were found between postpartum-derived cells and controls. The results of real-time PCR were confirmed by conventional PCR. Sequencing of PCR products further validated these observations. No significant difference in the expression level of CXC ligand 3 was found between postpartum-derived cells and controls using conventional PCR CXC ligand 3 primers listed above.

The production of the cytokine, IL-8 in postpartum was elevated in both Growth Medium-cultured and serum-starved postpartum-derived cells. All real-time PCR data was validated with conventional PCR and by sequencing PCR products.

When supernatants of cells grown in serum-free medium were examined for the presence of IL-8, the highest amounts were detected in media derived from umbilical-derived cells and some isolates of placenta cells (Table 10-1). No IL-8 was detected in medium derived from human dermal fibroblasts.

TABLE 10-1

| IL-8 protein amount measured by ELISA | |
| --- | --- |
| Cell type | IL-8 |
| hFibro | ND |
| Placenta Isolate 1 | ND |
| Umb Isolate 1 | 2058.42 ± 144.67 |
| Placenta Isolate 2 | ND |
| Umb Isolate 2 | 2368.86 ± 22.73 |
| Placenta Isolate3 (normal O$_2$) | 17.27 ± 8.63 |
| Placenta Isolate 3 (lowO$_2$, W/O BME) | 264.92 ± 9.88 |

Results of the ELISA assay for interleukin-8 (IL-8) performed on placenta-and umbilicus-derived cells as well as human skin fibroblasts.
Values are presented here are picograms/million cells, n = 2, sem.
ND: Not Detected Placenta-derived cells were also examined for the production of oxidized LDL receptor, GCP-2 and GROalpha by FACS analysis. Cells tested positive for GCP-2. Oxidized LDL receptor and GRO were not detected by this method.

Placenta-derived cells were also tested for the production of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the production of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilicus-derived cells were positive for alpha-smooth muscle actin and vimentin, with the staining pattern consistent through passage 11.

Summary. Concordance between gene expression levels measured by microarray and PCR (both real-time and conventional) has been established for four genes: oxidized LDL receptor 1, rennin, reticulon, and IL-8. The expression of these genes was differentially regulated at the mRNA level in PPDCs, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level, however GCP-2 was detected at the protein level by FACS analysis in the placenta-derived cells. Although this result is not reflected by data originally obtained from the microarray experiment, this may be due to a difference in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, in the Growth Medium and under the conditions utilized in these procedures. Cells derived from the human umbilical cord at passage 0 were probed for the expression of alpha-smooth muscle actin and vimentin, and were positive for both. The staining pattern was preserved through passage 11.

EXAMPLE 11

Secretion of Trophic Factors by Postpartum-Derived Cells

The secretion of selected trophic factors from placenta- and umbilicus-derived cells was measured. Factors selected for detection included: (1) those known to have angiogenic activity, such as hepatocyte growth factor (HGF) (Rosen et al. (1997) Ciba Found. Symp. 212:215-26), monocyte chemotactic protein 1 (MCP-1) (Salcedo et al. (2000) Blood 96; 34-40), interleukin-8 (IL-8) (Li et al. (2003) J. Immunol. 170:3369-76), keratinocyte growth factor (KGF), basic fibroblast growth factor (bFGF), vascular endothelial growth factor (VEGF) (Hughes et al. (2004) Ann. Thorac. Surg. 77:812-8), matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1alpha (SDF-1 alpha); (2) those known to have neurotrophic/neuroprotective activity, such as brain-derived neurotrophic factor (BDNF) (Cheng et al. (2003) Dev. Biol. 258; 319-33), interleukin-6 (IL-6), granulocyte chemotactic protein-2 (GCP-2), transforming growth factor beta2 (TGFbeta2); and (3) those known to have chemokine activity, such as macrophage inflammatory protein 1alpha (MIP1a), macrophage inflammatory protein 1beta (MIP1b), monocyte chemoattractant-1 (MCP-1), Rantes (regulated on activation, normal T cell expressed and secreted), I309, thymus and activation-regulated chemokine (TARC), Eotaxin, macrophage-derived chemokine (MDC), IL-8).

Methods & Materials

Cell culture. PPDCs from placenta and umbilicus as well as human fibroblasts derived from human neonatal foreskin were cultured in Growth Medium with penicillin/streptomycin on gelatin-coated T75 flasks. Cells were cryopreserved at passage 11 and stored in liquid nitrogen. After thawing of the cells, Growth Medium was added to the cells followed by transfer to a 15 milliliter centrifuge tube and centrifugation of the cells at 150×g for 5 minutes. The supernatant was discarded. The cell pellet was resuspended in 4 milliliters Growth Medium, and cells were counted. Cells were seeded at 375,000 cells/75 cm$^2$ flask containing 15 milliliters of Growth Medium and cultured for 24 hours. The medium was changed to a serum-free medium (DMEM-low glucose (Gibco), 0.1% (w/v) bovine serum albumin (Sigma), penicillin/streptomycin (Gibco)) for 8 hours. Conditioned serum-free medium was collected at the end of incubation by centrifugation at 14,000×g for 5 minutes and stored at −20° C. To estimate the number of cells in each flask, cells were washed with PBS and detached using 2 milliliters trypsin/EDTA. Trypsin activity was inhibited by addition of 8 milliliters Growth Medium. Cells were centrifuged at 150×g for 5 minutes. Supernatant was removed, and cells were resuspended in 1 milliliter Growth Medium. Cell number was estimated using a hemocytometer.

ELISA assay. Cells were grown at 37° C. in 5% carbon dioxide and atmospheric oxygen. Placenta-derived cells (batch 101503) also were grown in 5% oxygen or beta-mercaptoethanol (BME). The amount of MCP-1, IL-6, VEGF, SDF-1alpha, GCP-2, IL-8, and TGF-beta 2 produced by each cell sample was measured by an ELISA assay (R&D Systems, Minneapolis, Minn.). All assays were performed according to the manufacturer's instructions.

SearchLight multiplexed ELISA assay. Chemokines (MIP1a, MIP1b, MCP-1, Rantes, I309, TARC, Eotaxin, MDC, IL8), BDNF, and angiogenic factors (HGF, KGF, bFGF, VEGF, TIMP1, ANG2, PDGF-bb, TPO, HB-EGF were measured using SearchLight Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the original standard or sample.

Results

ELISA assay. MCP-1 and IL-6 were secreted by placenta- and umbilicus-derived cells and dermal fibroblasts (Table 11-1). SDF-1alpha was secreted by placenta-derived cells cultured in 5% $O_2$ and by fibroblasts. GCP-2 and IL-8 were secreted by umbilicus-derived cells and by placenta-derived cells cultured in the presence of BME or 5% $O_2$. GCP-2 also was secreted by human fibroblasts. TGF-beta2 was not detectable by ELISA assay.

TABLE 11-1

ELISA assay results
(values presented are picograms/milliliter/million cells (n = 2, sem)

| | MCP-1 | IL-6 | VEGF | SDF-1α | GCP-2 | IL-8 | TGF-β2 |
|---|---|---|---|---|---|---|---|
| Fibroblast | 17 ± 1 | 61 ± 3 | 29 ± 2 | 19 ± 1 | 21 ± 1 | ND | ND |
| Placenta (042303) | 60 ± 3 | 41 ± 2 | ND | ND | ND | ND | ND |
| Umbilicus (022803) | 1150 ± 74 | 4234 ± 289 | ND | ND | 160 ± 11 | 2058 ± 145 | ND |
| Placenta (071003) | 125 ± 16 | 10 ± 1 | ND | ND | ND | ND | ND |
| Umbilicus (071003) | 2794 ± 84 | 1356 ± 43 | ND | ND | 2184 ± 98 | 2369 ± 23 | ND |
| Placenta (101503) BME | 21 ± 10 | 67 ± 3 | ND | ND | 44 ± 9 | 17 ± 9 | ND |
| Placenta (101503) 5% $O_2$, W/O BME | 77 ± 16 | 339 ± 21 | ND | 1149 ± 137 | 54 ± 2 | 265 ± 10 | ND |

Key:
ND: Not Detected.

SearchLight multiplexed ELISA assay. TIMP1, TPO, KGF, HGF, FGF, HBEGF, BDNF, MIP1b, MCP1, RANTES, I309, TARC, MDC, and IL-8 were secreted from umbilicus-derived cells (Tables 11-2 and 11-3). TIMP1, TPO, KGF, HGF, HBEGF, BDNF, MIP1a, MCP-1, RANTES, TARC, Eotaxin, and IL-8 were secreted from placenta-derived cells (Tables 12-2 and 12-3). No Ang2, VEGF, or PDGF-bb were detected.

TABLE 11-2

SearchLight Multiplexed ELISA assay results

| | TIMP1 | ANG2 | PDGFbb | TPO | KGF | HGF | FGF | VEGF | HBEGF | BDNF |
|---|---|---|---|---|---|---|---|---|---|---|
| Hfb | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.81.3 | ND |
| U1 | 57718.4 | ND | ND | 1240.0 | 5.8 | 559.3 | 148.7 | ND | 9.3 | 165.7 |
| P3 | 14176.8 | ND | ND | 568.7 | 5.2 | 10.2 | ND | ND | 1.9 | 33.6 |
| U3 | 21850.0 | ND | ND | 1134.5 | 9.0 | 195.6 | 30.8 | ND | 5.4 | 388.6 |

Key:
hFB (human fibroblasts),
P1 (placenta-derived cells (042303)),
U1 (umbilicus-derived cells (022803)),
P3 (placenta-derived cells(071003)),
U3 (umbilicus-derived cells (071003)).
ND: Not Detected.

TABLE 11-3

SearchLight Multiplexed ELISA assay results

|     | MIP1a | MIP1b | MCP1 | RANTES | I309 | TARC | Eotaxin | MDC | IL8 |
| --- | --- | --- | --- | --- | --- | --- | --- | --- | --- |
| hFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| U1 | ND | 8.0 | 1694.2 | ND | 22.4 | 37.6 | ND | 18.9 | 51930.1 |
| P3 | ND | ND | 102.7 | ND | ND | 0.4 | ND | ND | 63.8 |
| U3 | ND | 5.2 | 2018.7 | 41.5 | 11.6 | 21.4 | ND | 4.8 | 10515.9 |

Key:
hFB (human fibroblasts),
P1 (placenta-derived PPDC (042303)),
U1 (umbilicus-derived PPDC (022803)),
P3 (placenta-derived PPDC (071003)),
U3 (umbilicus-derived PPDC (071003)).
ND: Not Detected.

Summary. Umbilicus- and placenta-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration.

EXAMPLE 12

In Vitro Immunological Evaluation of Postpartum-Derived Cells

Postpartum-derived cells (PPDCs) were evaluated in vitro for their immunological characteristics in an effort to predict the immunological response, if any, these cells would elicit upon in vivo transplantation. PPDCs were assayed by flow cytometry for the presence of HLA-DR, HLA-DP, HLA-DQ, CD80, CD86, and B7-H2. These proteins are expressed by antigen-presenting cells (APC) and are required for the direct stimulation of naïve CD4+ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, 2003, supra), CD 178 (Coumans, et al., (1999) *Journal of Immunological Methods* 224, 185-196), and PD-L2 (Abbas & Lichtman, 2003, supra; Brown, et. al. (2003) *The Journal of Immunology* 170, 1257-1266). The expression of these proteins by cells residing in placental tissues is thought to mediate the immuno-privileged status of placental tissues in utero. To predict the extent to which placenta- and umbilicus-derived cell lines elicit an immune response in vivo, the cell lines were tested in a one-way mixed lymphocyte reaction (MLR).

Materials and Methods

Cell culture. Cells were cultured to confluence in Growth Medium containing penicillin/streptomycin in T75 flasks (Corning, Corning, N.Y.) coated with 2% gelatin (Sigma, St. Louis, Mo.).

Antibody Staining. Cells were washed in phosphate buffered saline (PBS) (Gibco, Carlsbad, Calif.) and detached with Trypsin/EDTA (Gibco, Carlsbad, Mo.). Cells were harvested, centrifuged, and re-suspended in 3% (v/v) FBS in PBS at a cell concentration of $1 \times 10^7$ per milliliter. Antibody (Table 12-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 12-1

Antibodies

| Antibody | Manufacturer | Catalog Number |
| --- | --- | --- |
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD 178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Mixed Lymphocyte Reaction. Cryopreserved vials of passage 10 umbilicus-derived cells labeled as cell line A and passage 11 placenta-derived cells labeled as cell line B were sent on dry ice to CTBR (Senneville, Quebec) to conduct a mixed lymphocyte reaction using CTBR SOP No. CAC-031. Peripheral blood mononuclear cells (PBMCs) were collected from multiple male and female volunteer donors. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, [$^3$H]thymidine was added to each sample and cultured for 18 hours. Following harvest of the cells, radiolabeled DNA was extracted, and [$^3$H]-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the PPDCs was calculated as the mean proliferation of the receiver plus mitomycin C-treated postpartum cell line divided by the baseline proliferation of the receiver.

Results

Mixed lymphocyte reaction—placenta-derived cells. Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta-derived cell lines were treated with mitomycin C and cultured in a mixed lymphocyte reaction with the six individual allogeneic receivers. Reactions were performed in triplicate using two cell culture plates with three receivers per plate (Table 12-2). The average stimulation index ranged from 1.3 (plate 2) to 3 (plate 1) and the allogeneic donor positive controls ranged from 46.25 (plate 2) to 279 (plate 1) (Table 12-3).

TABLE 12-2

Mixed Lymphocyte Reaction Data - Cell Line B (Placenta)
DPM for Proliferation Assay

| Analytical number | Culture System | Replicates 1 | 2 | 3 | Mean | SD | CV |
|---|---|---|---|---|---|---|---|
| | Plate ID: Plate1 | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 (allogenic donor) | Proliferation baseline of receiver | 84 | 242 | 208 | 178.0 | 83.16 | 46.7 |
| | Control of autostimulation (Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin C treated autologous cells) | 822 | 1075 | 487 | 794.7 | 294.95 | 37.1 |
| | Plate ID: Plate 2 | | | | | | |
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 12-3

Average stimulation index of placenta cells and an allogeneic donor in a mixed lymphocyte reaction with six individual allogeneic receivers
Average Stimulation Index

|  | Recipient | Placenta |
|---|---|---|
| Plate 1 (receivers 1-3) | 279 | 3 |
| Plate 2 (receivers 4-6) | 46.25 | 1.3 |

Mixed lymphocyte reaction—umbilicus-derived cells. Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and umbilicus-derived cell lines were mitomycin C-treated and cultured in a mixed lymphocyte reaction with the five individual allogeneic receivers. Reactions were performed in triplicate using two cell culture plates with three receivers per plate (Table 12-4). The average stimulation index ranged from 6.5 (plate 1) to 9 (plate 2) and the allogeneic donor positive controls ranged from 42.75 (plate 1) to 70 (plate 2) (Table 12-5).

TABLE 12-5

Average stimulation index of umbilicus-derived cells and an allogeneic donor in a mixed lymphocyte reaction with five individual allogeneic receivers.
Average Stimulation Index

|  | Recipient | Umbilicus |
|---|---|---|
| Plate 1 (receivers 1-4) | 42.75 | 6.5 |
| Plate 2 (receiver 5) | 70 | 9 |

Antigen presenting cell markers—placenta-derived cells. Histograms of placenta-derived cells analyzed by flow cytometry show negative expression of HLA-DR, DP, DQ, CD80, CD86, and B7-H2, as noted by fluorescence value consistent with the IgG control, indicating that placental-derived cell lines lack the cell surface molecules required to directly stimulate CD4$^+$ T cells.

Immunomodulating markers—placenta-derived cells. Histograms of placenta-derived cells analyzed by flow cytometry show positive expression of PD-L2, as noted by the increased value of fluorescence relative to the IgG control, and negative expression of CD178 and HLA-G, as noted by fluorescence value consistent with the IgG control.

TABLE 12-4

Mixed Lymphocyte Reaction Data- Cell Line A (Umbilicus)
DPM for Proliferation Assay

| Analytical number | Culture System | Replicates 1 | 2 | 3 | Mean | SD | CV |
|---|---|---|---|---|---|---|---|
| | Plate ID: Plate1 | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| | Plate ID: Plate 2 | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| Cell line type A | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

Antigen presenting cell markers—umbilicus-derived cells. Histograms of umbilicus-derived cells analyzed by flow cytometry show negative expression of HLA-DR, DP, DQ, CD80, CD86, and B7-H2, as noted by fluorescence value consistent with the IgG control, indicating that umbilical-derived cell lines lack the cell surface molecules required to directly stimulate CD4+ T cells.

Immunomodulating cell markers—umbilicus-derived cells. Histograms of umbilicus-derived cells analyzed by flow cytometry show positive expression of PD-L2, as noted by the increased value of fluorescence relative to the IgG control, and negative expression of CD178 and HLA-G, as noted by fluorescence value consistent with the IgG control.

Summary. In the mixed lymphocyte reactions conducted with placenta-derived cell lines, the average stimulation index ranged from 1.3 to 3, and that of the allogeneic positive controls ranged from 46.25 to 279. In the mixed lymphocyte reactions conducted with umbilicus-derived cell lines the average stimulation index ranged from 6.5 to 9, and that of the allogeneic positive controls ranged from 42.75 to 70. Placenta- and umbilicus-derived cell lines were negative for the expression of the stimulating proteins HLA-DR, HLA-DP, HLA-DQ, CD80, CD86, and B7-H2, as measured by flow cytometry. Placenta- and umbilicus-derived cell lines were negative for the expression of immuno-modulating proteins HLA-G and CD178 and positive for the expression of PD-L2, as measured by flow cytometry. Allogeneic donor PBMCs contain antigen-presenting cells expressing HLA-DR, DQ, CD8, CD86, and B7-H2, thereby allowing for the stimulation of naïve CD4+ T cells. The absence of antigen-presenting cell surface molecules on placenta- and umbilicus-derived cells required for the direct stimulation of naïve CD4+ T cells and the presence of PD-L2, an immunomodulating protein, may account for the low stimulation index exhibited by these cells in a MLR as compared to allogeneic controls.

EXAMPLE 13

In Vitro Evaluation of Human Postpartum Derived Cells as a Third Party to Suppress an Immunological Response Placenta- and umbilicus-derived cells (PDCs, UDCs) were evaluated in vitro for their ability as a third party to suppress an immunological response between two haplotype mismatched peripheral blood mononuclear cell (PBMC) populations. Recent reports have suggested that various cell types maybe useful for the suppression of an immunological response between graft and donor cell populations (1,2). A mixed lymphocyte reaction was used to investigate the ability of PDCs or UDCs to act as a third party to suppress an immune response between two haplotype mismatched peripheral blood mononuclear cell (PBMC) populations (3).
Materials and Methods:

PBMC Isolation and Culture. PBMC were immediately isolated from whole blood obtained from healthy consenting donors by gradient centrifugation and re-suspended in RPMI 1640 with 10% FBS.

PDC and UDC Culture. Placenta- or umbilicus-derived cells were seeded at 5.0E+03 cells per cm/sq., expanded to approximately 70% confluence in growth media (DMEM-low glucose, 15% FBS, BME, and P/S), and harvested with trypsin. Cells were treated with 500 U/ml IFN-γ during expansion to induce HLA-DR, DP, DQ expression.

Haplotype Mismatch. Stimulator PBMC, responder PBMC, and PDC or UDC were 6 of 6 major histocompatibility mismatches.

Stimulator cells proliferation inhibition. PDC or UDC and stimulator PBMC were treated with 25 μg/ml mitomycin C for 30 minutes at standard conditions to inhibit cell proliferation. Cells were then washed with fresh RPMI 1640.

Mixed Lymphocyte Reaction. Mixed lymphocyte reaction were conducted in round bottom 96 well plates with all cells cultured in RPMI 1640 containing 10% FBS. Mitomycin C treated PDC or UDC were plated in designated wells at 2.5E+04 or 1.25E+04 cells per well. Mitomycin C treated stimulator PBMC and responder PBMC were plated in designated wells each at 1.0E+05 cells per well.

Thymidine Incorporation. After six days of culture 20 μl of a 50 μCi/ml [$^3$H] thymidine solution was added to each well. After seven days of culture cells were evaluated for [$^3$H] thymidine incorporation with a TopCount1 scintillation counter instrument. Label incorporation was expressed as counts per minute (cpm)

Figure 2:
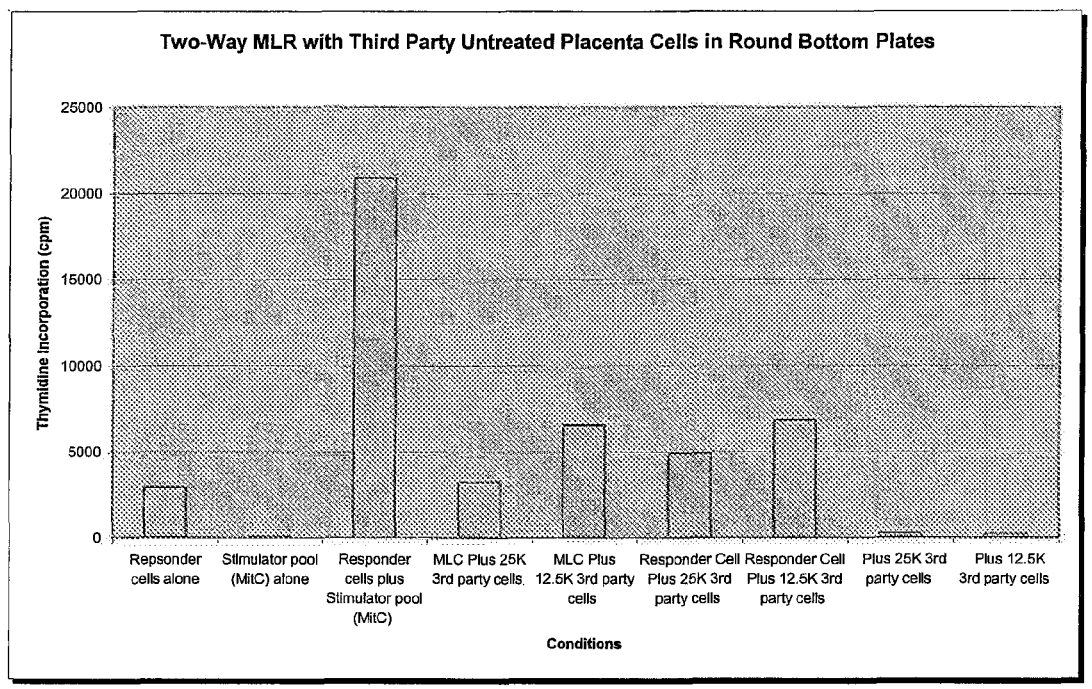
FIG. 2. Bar graph showing results of two-way mixed lymphocyte reaction (MLR) with untreated placenta-derived cells in round-bottom plates.

Results:

Results for placenta-derived cells are shown in tables 13-1, 13-2 and in FIGS. 1 and 2.

TABLE 13-1

IFN-γ treated placenta derived cells

| Test Condition | Treatment | $^3$H incorporation (cpm) |
|---|---|---|
| Proliferation Control | Responder cells alone | 2970 |
| Proliferation Control | Stimulator pool (MitC) alone | 67 |
| One-Way MLR Control | Responder cells plus Stimulator pool (MitC) | 20893 |
| Two-Way MLR with 3rd party | MLC Plus 25,000 3rd party cells | 3459 |
| Two-Way MLR with 3rd party | MLC Plus 12,500 3rd party cells | 10944 |
| One-Way MLR Control | Responder Cell Plus 25,000 3rd party cells | 6714 |
| One-Way MLR Control | Responder Cell Plus 12,500 3rd party cells | 7113 |
| Proliferation Control | 25,000 3rd party cells | 223 |
| Proliferation Control | 12,500 3rd party cells | 411 |

TABLE 13-2

Untreated placenta derived cells

| Test Condition | Treatment | $^3$H incorporation |
|---|---|---|
| Proliferation Control | Responder cells alone | 2970 |
| Proliferation Control | Stimulator pool (MitC) alone | 67 |
| One-Way MLR Control | Responder cells plus Stimulator pool (MitC) | 20893 |
| Two-Way MLR with 3rd party | MLC Plus 25,000 3rd party cells | 3250 |
| Two-Way MLR with 3rd party | MLC Plus 12,500 3rd party cells | 6586 |
| One-Way MLR Control | Responder Cell Plus 25K 3rd party cells | 4915 |
| One-Way MLR Control | Responder Cell Plus 12.5K 3rd party cells | 6887 |
| Proliferation Control | Plus 25,000 3rd party cells | 291 |
| Proliferation Control | Plus 12,500 3rd party cells | 243 |

Figure 3:
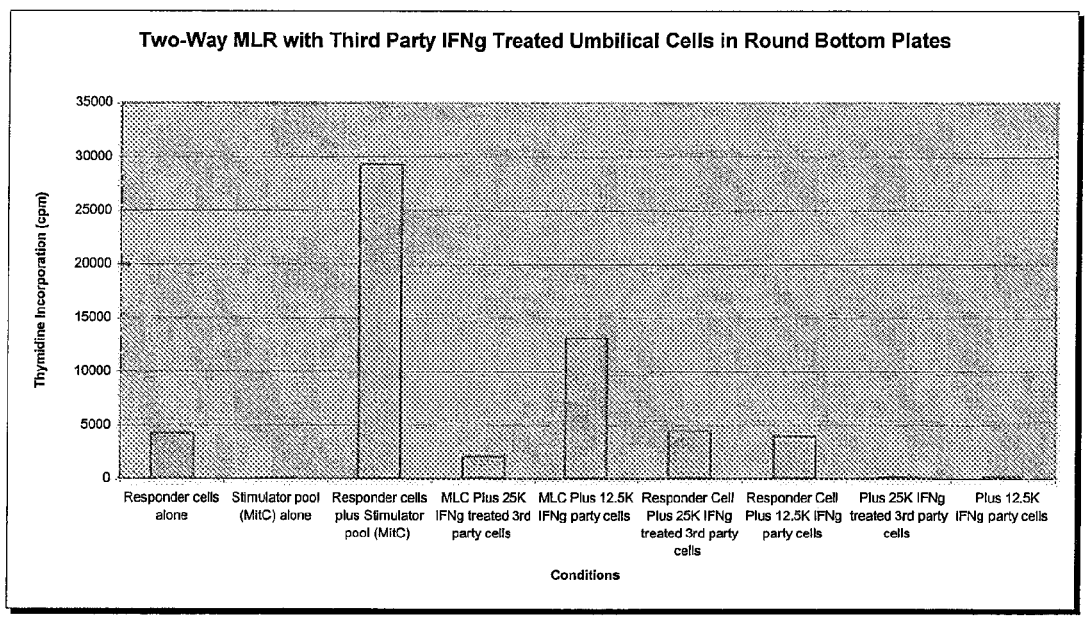
FIG. 3. Bar graph showing results of two-way mixed lymphocyte reaction (MLR) with third party IFNγ-treated umbilicus-derived cells in round-bottom plates.
Figure 4:
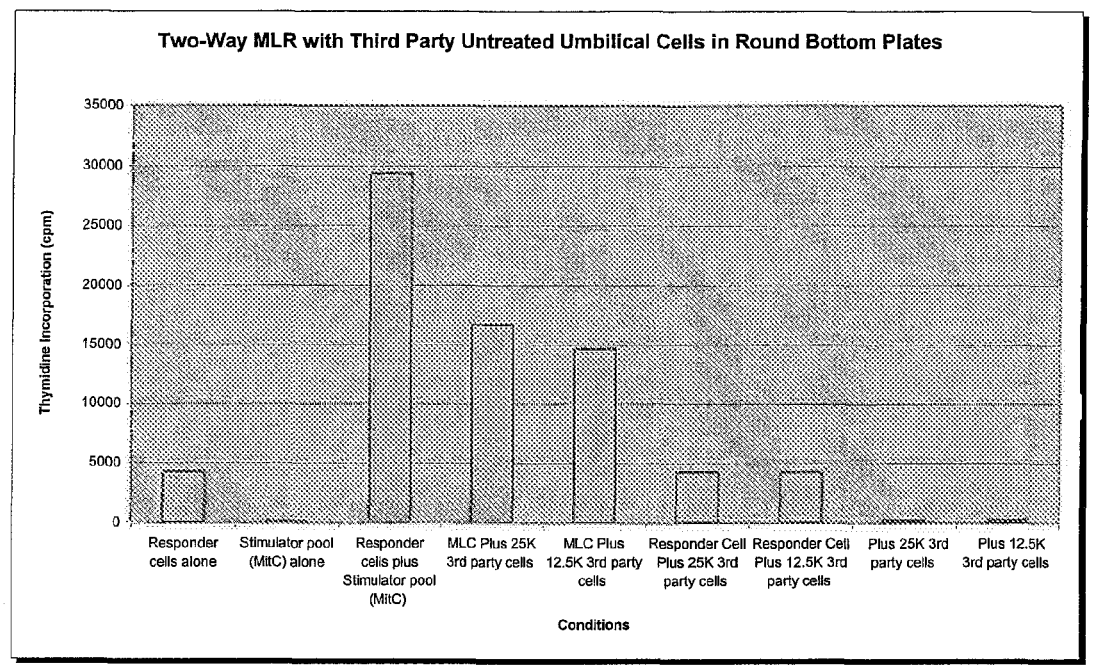
FIG. 4. Bar graph showing results of two-way mixed lymphocyte reaction (MLR) with untreated umbilicus-derived cells in round-bottom plates.

Results for umbilicus-derived cells are shown in tables 13-3, 13-4 and in FIGS. 3 and 4.

TABLE 13-3

IFN-γ treated umbilicus derived cells

| Test Condition | Treatment | 3H Incorporation (cpm) |
|---|---|---|
| Proliferation Control | Responder cells alone | 4275 |
| Proliferation Control | Stimulator pool (MitC) alone | 79 |
| One-Way MLR Control | Responder cells plus Stimulator pool (MitC) | 29362 |
| Two-Way MLR with 3rd party | MLC Plus 25,000 IFNg treated 3rd party cells | 2105 |
| Two-Way MLR with 3rd party | MLC Plus 12,500 IFNg 3rd party cells | 13175 |
| One-Way MLR Control | Responder Cell Plus 25,000 IFNg treated 3rd party cells | 4496 |
| One-Way MLR Control | Responder Cell Plus 12,500 IFNg 3rd party cells | 4019 |
| Proliferation Control | 25,000 IFNg treated 3rd party cells | 172 |
| Proliferation Control | 12,500 IFNg 3rd party cells | 196 |

TABLE 13-4

Untreated umbilicus derived cells

| Test Condition | Treatment | 3H Incorporation (cpm) |
|---|---|---|
| Proliferation Control | Responder cells alone | 4275 |
| Proliferation Control | Stimulator pool (MitC) alone | 79 |
| One-Way MLR Control | Responder cells plus Stimulator pool (MitC) | 29362 |
| Two-Way MLR with 3rd party | MLC Plus 25,000 3rd party cells | 16738 |
| Two-Way MLR with 3rd party | MLC Plus 12,500 3rd party cells | 14709 |
| One-Way MLR Control | Responder Cell Plus 25,000 3rd party cells | 4273 |
| One-Way MLR Control | Responder Cell Plus 12,500 3rd party cells | 4276 |
| Proliferation Control | 25,000 3rd party cells | 235 |
| Proliferation Control | 12,500 3rd party cells | 257 |

As can be seen from the tables and figures, in the one-way MLR, the responder PBMCs showed increased [$^3$H] thymidine incorporation as compared to responder PBMC only and stimulator PBMC only. This suggests proliferation of these cells when co-cultured with mitomycin C treated stimulator PBMCs. This level of responder PBMC proliferation suggests an immunological response of the responder PBMC to the mitomycin C treated stimulator PBMC.

The level of [$^3$H] thymidine incorporation by responder PBMC co-cultured with haplotype-mismatched mitomycin C treated PDC alone was less than the level of [$^3$H] thymidine incorporated by responder PBMC co-cultured with haplotype-mismatched mitomycin C treated stimulator PBMCs. This suggests that PDC elicit a diminished immune response from haplotype-mismatched responder PBMCs in this assay.

The addition of mitomycin C treated PDC (IFN-γ treated or untreated) as a third party in these cultures decreases the level of responder PBMC [$^3$H] labeled thymidine incorporation. This suggests that the third party PDC suppressed the immunological response of the responder PBMC to the mitomycin C treated stimulator cells. This suppression appears to be dose dependent as cell dose was directly related to responder PBMC inhibition.

References for Example 13
1) Bruder S P et. al. U.S. Pat. No. 6,355,239 B1 (2002)
2) Blood. 2005 Feb. 15; 105(4):1815-22
3) Klein, Jan Immunology: The Science of Self-Nonself Discrimination John Wiley & Sons, New York p. 453-8

The present invention is not limited to the embodiments described and exemplified above, but is capable of variation and modification within the scope of the appended claims.

What is claimed:

1. A method for inhibiting an adverse immune response in a transplant recipient in need thereof comprising:
   (i) identifying a transplant recipient that is histocompatibility-mismatched to a transplant donor,
   (ii) Identifying a composition of human umbilical cord tissue cells exhibiting a lower stimulation index of naïve CD4+ T-cells, wherein the identification is by mixed lymphocyte reaction (MLR), wherein the MLR comprises (a) a population of lymphocytes allogenic to the transplant recipient and (b) a composition of human umbilical cord tissue cells allogenic to the transplant recipient, wherein the composition of human umbilical cord tissue cells is a homogeneous population of allogeneic umbilicus-derived cells derived from human umbilical cord tissue free of blood, said cells being capable of self-renewal and expansion in culture, wherein the cells are capable of growth in an atmosphere containing oxygen from about 5% to at least about 20%, and wherein said homogeneous population comprise having the following characteristics:
   (a) potential for at least 40 doublings in culture;
   (b) production of CD 10, CD 13, CD44, CD73, CD90, PDGFr-alpha, PD-L2 and HLA-A,B,C;
   (c) lack of production of CD31, CD34, CD45, CD80, CD86, CD117, CD141, CD 178, B7-H2, HLA-G, and HLA-DR,DP,DQ, as detected by flow cytometry;
   (d) expression of interleukin 8; reticulon 1; and chemokine (C-X-C motif) ligand 3;
   (e) secretion of MCP-1, IL-6, IL-8, GCP-2, HGF, KGF, FGF, HB-EGF, BDNF, TPO, MIP1b, RANTES, I309, MDC, and TIMP1; and
   (f) lack of secretion of TGF-beta2, ANG2, PDGFbb, MIP1a, and VEGF, as detected by ELISA,
   (iii) administering the identified composition of homogenous human umbilical cord tissue cell to the transplant recipient in an amount effective for inhibiting the adverse immune response in the transplant recipient that is histocompatibility-mismatched to the transplant donor,
   wherein the identified composition inhibits the adverse immune response in the transplant recipient that is histocompatibility-mismatched to the transplant donor.

2. The method of claim 1, wherein the adverse immune response is graft versus host disease.

3. The method of claim 1, wherein the adverse immune response is rejection of the transplanted tissue.

4. The method of claim 1 wherein the cell composition is administered by injection or infusion.

5. The method of claim 1, wherein the cell composition is administered by implantation of a device, scaffold or matrix implanted in the transplant recipient.

6. The method of claim 1, wherein the cell composition is administered with at least one other allogeneic cell type.

7. The method of claim 6, wherein the at least one other allogeneic cell type is administered simultaneously with, or before, or after, the umbilicus-derived cells.

8. The method of claim 1, wherein the cell composition is administered with at least one other agent for treating the adverse immune response.

9. The method of claim 8, wherein the at least one other agent is administered simultaneously with, or before, or after, the umbilicus-derived cells.

10. The method of claim 8, wherein the at least one other agent is one or more of an antithrombogenic agent, an anti-inflammatory agent, an immunosuppressive agent, an immunomodulatory agent, or an antiapoptotic agent.

11. A pharmaceutical composition for inhibiting an adverse immune response in a transplant recipient that is histocompatibility-mismatched to the transplant donor, comprising a pharmaceutically acceptable carrier and a composition of human umbilical cord tissue cells free of blood, said cells being capable of self-renewal and expansion in culture, wherein the cells are capable of growth in an atmosphere containing oxygen from about 5% to at least about 20%, and wherein said homogeneous population comprise having the following characteristics:
   (a) potential for at least 40 doublings in culture;
   (b) production of CD 10, CD 13, CD44, CD73, CD90, PDGFr-alpha, PD-L2 and HLA-A,B,C;
   (c) lack of production of CD31, CD34, CD45, CD80, CD86, CD117, CD141, CD 178, B7-H2, HLA-G, and HLA-DR,DP,DQ, as detected by flow cytometry;
   (d) expression of interleukin 8; reticulon 1; and chemokine (C—X—C motif) ligand 3;
   (e) secretion of MCP-1, IL-6, IL-8, GCP-2, HGF, KGF, FGF, HB-EGF, BDNF, TPO, MIP1b, RANTES, I309, MDC, and TIMP1; and
   (f) lack of secretion of TGF-beta2, ANG2, PDGFbb, MIP1a, and VEGF, as detected by ELISA.

12. The pharmaceutical composition of claim 11, wherein the adverse immune response is graft versus host disease.

13. The pharmaceutical composition of claim 11, wherein the adverse immune response is rejection of the transplanted tissue.

14. The pharmaceutical composition of claim 11, formulated for administration by injection or infusion.

15. The pharmaceutical composition of claim 11, formulated for administration by implantation of a device, scaffold or matrix implanted in the transplant recipient.

16. The pharmaceutical composition of claim 11, comprising at least about 50% human umbilical cord tissue cells.

17. The pharmaceutical composition of claim 11, comprising a substantially homogeneous population of human umbilical cord tissue cells.

18. The pharmaceutical composition of claim 11, comprising at least one other cell type.

19. The pharmaceutical composition of claim 11, comprising at least one other agent for treating the adverse immune response.

20. The pharmaceutical composition of claim 19, wherein the at least one other agent is one or more of an antithrombogenic agent, an anti-inflammatory agent, an immunosuppressive agent, an immunomodulatory agent, or an antiapoptotic agent.

21. A method for inhibiting an adverse immune response in a transplant recipient in need thereof comprising
administering an effective amount of a cell composition to a transplant recipient that is histocompatibility-mismatched to a transplant donor,
wherein the cell composition inhibits the adverse immune response in the transplant recipient that is histocompatibility-mismatched to the transplant donor,
wherein the cell composition comprises a pharmaceutically acceptable carrier and a homogeneous population of allogeneic umbilicus-derived cells derived from human umbilical cord tissue free of blood, said cells being capable of self-renewal and expansion in culture, wherein the cells and are capable of growth in an atmosphere containing oxygen from about 5% to at least about 20%, and wherein the cells comprise the following characteristics:
(a) potential for at least 40 doublings in culture;
(b) production of CD 10, CD 13, CD44, CD73, CD90, PDGFr-alpha, PD-L2 and HLA-A,B,C;
(c) lack of production of CD31, CD34, CD45, CD80, CD86, CD117, CD141, CD 178, B7-H2, HLA-G, and HLA-DR,DP,DQ, as detected by flow cytometry;
(d) expression of interleukin 8; reticulon 1; and chemokine (C—X—C motif) ligand 3;
(e) secretion of MCP-1, IL-6, IL-8, GCP-2, HGF, KGF, FGF, HB-EGF, BDNF, TPO, MIP1b, RANTES, I309, MDC, and TIMP1; and
(f) lack of secretion of TGF-beta2, ANG2, PDGFbb, MIP1a, and VEGF, as detected by ELISA.

22. The method of claim 21, wherein the adverse immune response is graft versus host disease.

23. The method of claim 21, wherein the adverse immune response is rejection of the transplanted tissue.

24. The method of claim 21, wherein the cell composition is administered by injection or infusion.

25. The method of claim 21, wherein the cell composition is administered by implantation of a device, scaffold or matrix implanted in the transplant recipient.

26. The method of claim 1, wherein the method comprises co-administration of the cell composition and an immunosuppressive agent.

27. The method of claim 21, wherein the method comprises co-administration of the cell composition and an immunosuppressive agent.

* * * * *